US008618068B2

(12) United States Patent
Perrine et al.

(10) Patent No.: US 8,618,068 B2
(45) Date of Patent: Dec. 31, 2013

(54) METHODS AND LOW DOSE REGIMENS FOR TREATING RED BLOOD CELL DISORDERS

(75) Inventors: Susan P Perrine, Weston, MA (US); Douglas V Faller, Weston, MA (US); Ronald J Berenson, Mercer Island, WA (US)

(73) Assignees: Trustees of Boston University, Boston, MA (US); Hemaquest Pharmaceuticals, Inc., Seattle, WA (US)

( * ) Notice: Subject to any disclaimer, the term of this patent is extended or adjusted under 35 U.S.C. 154(b) by 289 days.

(21) Appl. No.: 12/963,490

(22) Filed: Dec. 8, 2010

(65) Prior Publication Data

US 2011/0251149 A1  Oct. 13, 2011

Related U.S. Application Data

(60) Provisional application No. 61/411,369, filed on Nov. 8, 2010, provisional application No. 61/367,326, filed on Jul. 23, 2010, provisional application No. 61/312,090, filed on Mar. 9, 2010, provisional application No. 61/306,376, filed on Feb. 19, 2010, provisional application No. 61/295,650, filed on Jan. 15, 2010, provisional application No. 61/267,727, filed on Dec. 8, 2009.

(51) Int. Cl.
A61K 31/19 (2006.01)
A61K 31/706 (2006.01)
A61K 31/4406 (2006.01)
A61P 7/06 (2006.01)

(52) U.S. Cl.
USPC .................. 514/43; 514/357; 514/557

(58) Field of Classification Search
USPC ........................... 514/43, 357, 557
See application file for complete search history.

(56) References Cited

U.S. PATENT DOCUMENTS

| | | | |
|---|---|---|---|
| 3,471,513 A | 10/1969 | Chinn et al. |
| 3,904,612 A | 9/1975 | Nagasawa et al. |
| 4,008,323 A | 2/1977 | Cousse et al. |
| 4,011,336 A | 3/1977 | Amann et al. |
| 4,026,896 A | 5/1977 | Harita et al. |
| 4,031,243 A | 6/1977 | Aparicio et al. |
| 4,058,558 A | 11/1977 | Cousse et al. |
| 4,131,617 A | 12/1978 | Esanu |
| 4,176,193 A | 11/1979 | Esanu |
| 4,234,599 A | 11/1980 | Van Scott et al. |
| 4,613,616 A | 9/1986 | Winston et al. |
| 4,671,901 A | 6/1987 | Green |
| 4,699,926 A | 10/1987 | Abraham et al. |
| 4,704,402 A | 11/1987 | Abraham et al. |
| 4,723,958 A | 2/1988 | Pope et al. |
| 4,731,381 A | 3/1988 | Abraham et al. |
| 4,732,914 A | 3/1988 | Morton, Jr. |
| 4,735,967 A | 4/1988 | Neesby |
| 4,747,825 A | 5/1988 | Linkie et al. |
| 4,751,244 A | 6/1988 | Abraham et al. |
| 4,766,116 A | 8/1988 | Tatsuoka et al. |
| 4,820,711 A | 4/1989 | Pearlman |
| 4,822,821 A | 4/1989 | Perine |
| 4,849,426 A | 7/1989 | Pearlman |
| 4,851,229 A | 7/1989 | Magruder et al. |
| 4,853,388 A | 8/1989 | Pearlman |
| 4,880,624 A | 11/1989 | Metcalf et al. |
| 4,894,364 A | 1/1990 | Greer |
| 4,925,873 A | 5/1990 | Friedhoff et al. |
| 4,948,592 A | 8/1990 | Ayer et al. |
| 4,952,560 A | 8/1990 | Kigasawa et al. |
| 4,958,592 A | 9/1990 | Anthony et al. |
| 4,965,251 A | 10/1990 | Stamatoyannopoulos |
| 4,997,815 A | 3/1991 | Perrine et al. |
| 5,023,251 A | 6/1991 | Sattler et al. |
| 5,025,029 A | 6/1991 | Perrine |
| 5,032,507 A | 7/1991 | Yu et al. |
| 5,039,703 A | 8/1991 | Breuer |
| 5,081,124 A | 1/1992 | Hughes |
| 5,100,647 A | 3/1992 | Agus et al. |
| 5,137,734 A | 8/1992 | Spiegeman et al. |
| 5,185,436 A | 2/1993 | Villa et al. |
| 5,199,942 A | 4/1993 | Gillis |
| 5,208,333 A | 5/1993 | Paul et al. |
| 5,216,004 A | 6/1993 | Perrine |

(Continued)

FOREIGN PATENT DOCUMENTS

CA  1209037 A  8/1986
CA  2303268 A1  4/1995

(Continued)

OTHER PUBLICATIONS

U.S. Appl. No. 12/834,720, filed Jul. 12, 2010, Berenson et al.
U.S. Appl. No. 12/836,344, filed Jul. 14, 2010, Faller.
Abbott, et al. Quantitative structure-anticonvulsant activity relationships of valproic acid, related carboxylic acids and tetrazoles. Neuropharmacology. Mar. 1988;27(3):287-94.
Abe, et al. Sodium butyrate induction of milk-related antigens in human MCF-7 breast carcinoma cells. Cancer Research. Oct. 1984;44:4574-4577.
Abraham, et al. Design, synthesis, and testing of potenital antisickling agents. 1. Halogenated Benzyloxy and Phenoxy Acids. J. Med. Chem. 1982;25:1015-17.

(Continued)

*Primary Examiner* — Shaojia Anna Jiang
*Assistant Examiner* — Ganapathy Krishnan
(74) *Attorney, Agent, or Firm* — Ronald I. Eisenstein; Susanna C. Benn; Nixon Peabody LLP

(57) ABSTRACT

Disclosed herein are methods and low dose regimens for increasing fetal hemoglobin levels in patients with red blood cell disorders, such as beta thalassemia, sickle cell disease, other anemias, or blood loss. Fetal and total hemoglobin levels and red blood cell counts are increased by administering 2,2-dimethylbutyrate (DMB) alone or in combination with hydroxyurea, decitabine or an HDAC inhibitor. Treatment can be continued for at least two weeks.

29 Claims, 22 Drawing Sheets

(56) References Cited

U.S. PATENT DOCUMENTS

| | | | |
|---|---|---|---|
| 5,258,367 A | 11/1993 | Bazer et al. |
| 5,270,458 A | 12/1993 | Lemischka |
| 5,366,996 A | 11/1994 | Elford |
| 5,378,716 A | 1/1995 | Hamanaka et al. |
| 5,403,590 A | 4/1995 | Forse |
| 5,403,867 A | 4/1995 | Okumura et al. |
| 5,468,731 A | 11/1995 | Matsuo et al. |
| 5,635,532 A | 6/1997 | Samid |
| 5,654,333 A | 8/1997 | Samid |
| 5,661,179 A | 8/1997 | Samid |
| 5,674,898 A | 10/1997 | Cheng et al. |
| 5,674,912 A | 10/1997 | Martin |
| 5,679,707 A | 10/1997 | Okumura et al. |
| 5,710,178 A | 1/1998 | Samid |
| 5,750,571 A | 5/1998 | Cheng et al. |
| 5,780,451 A | 7/1998 | DeMichele et al. |
| 5,843,994 A | 12/1998 | Samid |
| 5,846,528 A | 12/1998 | Podsakoff et al. |
| 5,852,056 A | 12/1998 | Samid |
| 5,858,365 A | 1/1999 | Faller et al. |
| 5,883,123 A | 3/1999 | Tung et al. |
| 5,912,269 A | 6/1999 | Tung et al. |
| 5,932,545 A | 8/1999 | Henkin et al. |
| 5,939,456 A | 8/1999 | Perrine |
| 5,945,407 A | 8/1999 | Bemis et al. |
| 5,952,314 A | 9/1999 | DeMichele et al. |
| 6,011,000 A | 1/2000 | Perrine et al. |
| 6,030,961 A | 2/2000 | Nudelman et al. |
| 6,043,389 A | 3/2000 | Nudelman et al. |
| 6,197,743 B1 | 3/2001 | Faller |
| 6,231,880 B1 | 5/2001 | Perrine |
| 6,403,647 B1 | 6/2002 | Perrine |
| 6,451,334 B2 | 9/2002 | Perrine |
| 6,677,302 B2 | 1/2004 | Faller |
| 7,192,715 B2 | 3/2007 | Harley et al. |
| 7,265,153 B2 | 9/2007 | Faller et al. |
| 2001/0009922 A1 | 7/2001 | Faller |
| 2001/0027215 A1* | 10/2001 | Perrine ......................... 514/557 |
| 2003/0018069 A1 | 1/2003 | Faller et al. |
| 2003/0077297 A1 | 4/2003 | Chen et al. |
| 2006/0074046 A1 | 4/2006 | Redkar et al. |
| 2007/0232528 A1* | 10/2007 | Franke ............................. 514/9 |
| 2008/0027136 A1 | 1/2008 | Faller et al. |
| 2008/0057086 A1 | 3/2008 | Etter |
| 2008/0175849 A1 | 7/2008 | Smith et al. |
| 2008/0254026 A1 | 10/2008 | Long et al. |
| 2009/0082444 A1 | 3/2009 | Perrine |
| 2009/0130134 A1 | 5/2009 | Pancre et al. |
| 2011/0086869 A1 | 4/2011 | Perrine et al. |
| 2011/0245154 A1 | 10/2011 | Berenson et al. |

FOREIGN PATENT DOCUMENTS

| | | |
|---|---|---|
| CA | 2173976 A1 | 2/2008 |
| EP | 0069659 A1 | 1/1983 |
| EP | 0224599 A1 | 6/1987 |
| EP | 0320726 A2 | 6/1989 |
| EP | 0324574 A2 | 7/1989 |
| EP | 0350287 A2 | 1/1990 |
| EP | 0371789 B1 | 6/1990 |
| EP | 0320726 A3 | 8/1990 |
| EP | 0324574 A3 | 12/1990 |
| EP | 0546261 A2 | 6/1993 |
| EP | 0546261 A3 | 8/1993 |
| EP | 0617966 A1 | 10/1994 |
| GB | 2126082 A | 3/1984 |
| JP | 50-89335 | 7/1975 |
| JP | 61-180740 A | 8/1986 |
| WO | WO 90/11071 A1 | 10/1990 |
| WO | WO 91/01719 A1 | 2/1991 |
| WO | WO 92/03155 A1 | 3/1992 |
| WO | WO 92/04913 A1 | 4/1992 |
| WO | WO 93/07866 A2 | 4/1993 |
| WO | WO 93/07866 A3 | 5/1993 |
| WO | WO 93/18761 A1 | 9/1993 |
| WO | WO 94/04671 A1 | 3/1994 |
| WO | WO 95/10271 A2 | 4/1995 |
| WO | WO 95/11699 A1 | 5/1995 |
| WO | WO 95/10271 A3 | 6/1995 |
| WO | WO 96/02244 A1 | 2/1996 |
| WO | WO 96/27369 A2 | 9/1996 |
| WO | WO 96/27369 A3 | 11/1996 |
| WO | WO 97/04761 A1 | 2/1997 |
| WO | WO 98/04290 A2 | 2/1998 |
| WO | WO 98/04290 A3 | 8/1998 |
| WO | WO 98/40078 A1 | 9/1998 |
| WO | WO 98/56370 A2 | 12/1998 |
| WO | WO 98/56370 A3 | 4/1999 |
| WO | WO-2007-133653 A2 | 11/2007 |
| WO | WO 2007/133653 A2 * | 11/2007 |

OTHER PUBLICATIONS

Abraham, et al. Synthesis of the minor fetal hemoglobin Fic in colonies of erythropoietic precursors isolated from human umbilical cord blood. American Journal of Hematology. 1982;12:207-213.

Al-Khatti, et al. Erythropoietin stimulates F-reticulocyte formation in sickle cell anemia. Trans. Assoc. Am. Physicians. 1988;101:54-61.

Anderson, et al. Molecular cloning of mast cell growth factor, a hematopoietin that is active in both membrane bound and soluble forms. Cell. Oct. 5, 1990;63:235-243.

Andrews, et al. A rapid micropreparation technique for extraction of DNA-binding proteins from limiting numbers of mammalian cells. Nucl. Acids Res. 1991;19:2499-2500.

Andrews, et al. Erythroid transcription factor NF-E2 is a haematopoietic-specific basic-leucine zipper protein. Nature. 1993;362:722-728.

Angastiniotis, et al. Global epidemiology of hemoglobin disorders. Ann N Y Acad Sci—Issue Cooley's Anemia: Seventh Symposium. Feb. 7, 2006;850:251-269. (Published Online).

Antoni, et al. NF-.kappa. B-Dependent and -Independent Pathways of HIV Activation in a Chronically Infected T Cell Line. Virology. 1994;202:684-694.

Archin, et al. Antiretroviral intensification and valproic acid lack sustained effect on residual HIV-1 viremia or resting CD4+ cell infection. PLoS One. Feb. 23, 2010;5(2):e9390 (p. 1-4).

Archin, et al. Expression of latent HIV induced by the potent HDAC inhibitor suberoylanilide hydroxamic acid. AIDS Res Hum Retroviruses. Feb. 2009;25(2):207-12.

Archin, et al. Expression of latent human immunodeficiency type 1 is induced by novel and selective histone deacetylase inhibitors. AIDS. Sep. 10, 2009;23(14):1799-806.

Archin, et al. Valproic acid without intensified antiviral therapy has limited impact on persistent HIV infection of resting CD4+ T cells. AIDS. Jun. 19, 2008;22(10):1131-5.

Armstrong, et al. Criteria for the definition of Epstein-Barr virus association in Hodgkin's disease. Leukemia. 1992;6:869-869.

Atweh, et al. Pharmacological induction of fetal hemoglobin in sickle cell disease and b-Thalassemia. Seminars in Hematology. 2001;38(4):367-373.

Atweh, et al. Sustained induction of fetal hemoglobin by pulsed butyrate therapy in sickle cell disease. Blood. 1999;93(6):1790-1797.

Augeron, et al. Emergence of permanently differentiated cell clones in a human colonic cancer cell line in culture after treatment with sodium butyrate. Cancer Research. Sep. 1984;44:3961-3969.

Barbul, et al. Arginine enhances wound healing and lymphocyte immune responses in humans. Surgery. Aug. 1990;108(2):331-6; discussion 336-7.

Barker, et al. The actions of cyclic AMP, its butyryl derivatives and Na butyrate on the proliferation of malignant trophoblast cells in vitro, Br. J. Cancer. 1977;35:314-321.

Barton, et al. The erythroid protein cGATA-1 Functions with a stage-specific factor to activate transcription of chromatin-assembled b-globin genes. Genes & Development. 1993;7:1796-809.

Bartram, et al. Proliferation of human colonic mucosa as an intermediate biomarker of carcinogenesis: effects of butyrate, deoxycholate, calcium, ammonia, and pH. Cancer Research. Jul. 15, 1993;53:3283-3288.

(56) References Cited

OTHER PUBLICATIONS

Basson, et al. Butyrate-induced enterocyte differentiation and mucosal wound healing. Gastroenterology. 1993; 104(4) supp.:A235.
Belcheva, et al. Up-regulation of delta opioid receptors in neuroblastoma hybrid cells: evidence for differences in the mechanisms of action of sodium butyrate and naltrexone. J Pharmacol Exp Ther. Oct. 1991;259(1):302-9.
Berkovitch, et al. Pharmacokinetics of arginine butyrate in patients with hemoglobinopathy. Environ Tox and Pharm. 1996;2(4):403-405.
Bernards, et al. Physical mapping of the globin gene deletion in hereditary persistence of foetal haemoglobin (HPFH). Nucleic Acids Research. 1980;8(7):1521-1534.
Bingham. Patty's Toxicology. John Wiley and Sons, Incorporated. Jan. 1, 2001;5:707-711.
Birgens, et al. The thalassaemia syndromes. Scand J Clin Lab Invest. 2007; 67(1):11-26.
Blau, et al. Fetal hemoglobin induction with butyric acid: efficacy and toxicity. Blood. Jan. 15, 1993;81(2):529-37.
Bloch. Induced cell differentiation in cancer therapy. Cancer Treatment Reports. 1984;68:199-205.
Bohacek, et al. Identification of novel small-molecule inducers of fetal hemoglobin using pharmacophore and 'PSEUDO' receptor models. Chem Biol and Drug Design. 2006;67(5):318-328.
Bohan, et al. Mutational analysis of sodium butyrate inducible elements in the human immunodeficiency virus type 1 long terminal repeat. Virology. 1989;172:573-583.
Bohan, et al. Sodium butyrate activates human immunodeficiency virus long terminal repeat—directed expression. Biochem and Biophys. Res. Comm. 1987;148(3):899-905.
Bokiri, et al. Swine experiment with a feed containing sodium-n-butyrate. Chemical Abstracts. 1990;112(3):438.
Bonnet, et al. Detection of Epstein-Barr virus in invasive breast cancers. J Nat Cancer Inst. 1999;91(16):1376-1381.
Boosalis, et al. Short-chain fatty acid derivatives stimulate cell proliferation and induce STAT-5 activation. Blood. May 15,2001;97(10):3259-67.
Borgna-Pignatti, et al. Modern treatment of thalassaemia intermedia. Br J Haematol. 2007;138:291-304.
Borgna-Pignatti, et al. Survival and complications in thalassemia. Ann N Y Acad Sci—Issue Cooley's Anemia: Eighth Symposium. Jan. 6, 2006;1054:40-47. (Published Online).
Boulikas. Poly (ADP-ribose) synthesis in blocked and damaged cells and its relation to carcinogenesis. Anticancer Res. 1992;12(3):885-898.
Bourantas, et al. Administration of high dose of recombinant human erythropoietin to patients with β-thalassemia intermedia: a preliminary trial. Eur J Haematol. 1997;58:22-25.
Bourgeade, et al. Effect of sodium butyrate on the antiviral and anticellular action of interferon in normal and MSV-transformed cells. Int J Cancer. Sep. 15, 1979;24(3):314-8.
Bourgeade, et al. Enhancement of interferon anti-tumor action by sodium butyrate. Cancer Res. 1979;39:4720-4723.
Breitman, et al. Combinations of retinoic acid with either sodium butyrate, dimethyl, sulfoxide, or hexamethylene bisacetamide synergistically induce differentiation of the human myeoid leukemia cell line HL60. Cancer Research. 1990;50:6268-6273.
Breuer, et al. Rectal irrigation with short-chain fatty acids for distal ulcerative colitis. Dig. Dis. Sci.1991;36(2):185-187.
Briz, et al. Epstein-Barr virus associated B-cell lymphoma after autologous bone marrow transplantation for T-cell acute lymphoblastic leukaemia. Br J Haematol. 1997;98:485-487.
Brooks, et al. Epstein-Barr virus and lymphomas. Cancer Surv. 1999;33:99-123.
Brousset, et al. Detection of Epstein-Barr virus messenger RNA in Reed-Sternberg cells of Hodgkin's disease by in situ hybridization with biotinylated probes on specially processed modified acetone methyl benzoate xylene (ModAMeX) sections. Blood, 1991;77:1781-1786.

Bugaut, et al. Biological effects of short-chain fatty acids in nonruminant mammals. Amex. Rev. Nutr.1993;13:217-241.
Bunn. Mechanisms of disease—pathogenesis and treatment of sickle cell disease. N Engl J Med. Sep. 11, 1997;337:762-769.
Burkitt. A sarcoma involving the jaws in African children. Br J Surg. 1958;46:218-223.
Burns, et al. Butyrate induces selective transcriptional activation of a hypomethylated embryonic globin gene in adult erythroid cells. Blood. 1988;72(5):1536-1542.
Byrd, et al. Two types of transglutaminase in the PC12 pheochromocytoma cell line. The Journal of Biological Chemistry. Aug. 25, 1987;262(24):11699-11705.
Callery, et al. Identification of metabolites of the cell—differentiating agent hexamethylene bisacetamide in humans. Cancer Res. 1986;46:4900-4903.
Canceill, et al. Stereochimstry of the reduction of b-keto esters, p-keto amides, and b-keto nitriles by hydrides. Bull. Soc. Chim. 1970 Fr. 6:2180-2187. (Abstract only).
Caruso, et al. Regression of established macroscopic liver metastases after in situ transduction of a suicide gene. Proc Natl Acad Sci U S A. Aug. 1, 1993;90(15):7024-8.
Castaneda, et al. Enhancement of growth and survival and alterations in Bcl-family proteins in β-thalassemic erythroid progenitors by novel short-chain fatty acid derivatives. Blood Cells Mol. Dis. 2005;35(2):217-26.
Chang, et al. An analysis of fetal hemoglobin variation in sickle cell disease: the relative contributions of the X-linked factor, beta-globin haplotypes, alpha-globin gene number, gender, and age. Blood. Feb. 15, 1995;85(4):1111-1117.
Chany, et al. Antitumor effect of arginine butyrate in conjunction with corynebacterium and interferon. Int. J. Cancer. 1982;30:489-93.
Chany, et al. Effect of coordinated therapeutic assays using C. Parvum, Interferon and Arginine Butyrate on spontaneous disease and survival of AKR mice. Int. J. Cancer. 1993;32:379-383.
Charache, et al. Treatment of sickle cell anemia with 5-azacytidine results in increased fetal hemoglobin production and is associated with nonrandom hypomethylation of DNA around the gamma-delta-beta-globin gene complex. Proc. Natl. Acad. Sci. USA. 1983;80:4842-4846.
Charache, et al., Hydroxyurea-induced augmentation of fetal hemoglobin production in patients with sickle cell anemia. Blood. 1987;69(1):109-116.
Chen, et al. Tributyrin: a prodrug of butyric acid for potential clinical application in differentiation therapy. Cancer Research. Jul. 1, 1994;54:3494-3499.
Cheng, et al. Functional activation of the cystic fibrosis trafficking mutant .Delta.F508-CFTR by expression. Am. J. Physiol. 1995;268:L615-24.
Chu, et al. In situ detection of Epstein-Barr virus in breast cancer. Cancer Lett. 1998;124:53-57.
Clegg, et al. Abnormal human haemoglobins. Separation and characterization of the alpha and beta chains by chromatography, and the determination of two new variants, hb Chesapeak and hb J (Bangkok). J Mol Biol. Aug. 1966;19(1):91-108.
Coates, et al. Persistence of Epstein-Barr virus in Reed-Sternberg cells throughout the course of Hodgkin's disease. J Pathol. 1991;164:291-291.
Cohen, et al. Thalassemia. Hematology-American Society of Hematology Education Program Book. 2004:14-34.
Collins, et al. Oral sodium phenylbutyrate therapy in homozygous $ thalassemia: a clinical trial. Blood. Jan. 1, 1995;85(1):43-49.
Colombo. Natural history and pathogenesis of hepatitis C virus related hepatocellular carcinoma. Journal of Hepatology. 1999;31:(1):25-30. Suppl.
Constantaoulakis, et al. On the induction of fetal hemogloving by butyrates: in vivo and in vitro studies with sodium butyrate and comparison of combination treatments with 5-AzaC. Blood. Nov. 1, 1989;74(6):1963-1971.
Cook, et al. Effect of sodium butyrate on α-Fetoprotein gene expression in rat hepatoma cells in vitro. Cancer Research. Jul. 1985;45:3215-3219.

(56) References Cited

OTHER PUBLICATIONS

Copeland, et al. Mast cell growth factor maps near the steel locus on mouse chromosome 10 and is deleted in a number of steel alleles. Cell. Oct. 5, 1990;63:175-183.

Cossman, et al. Induction of differentiation in a case of common acute lymphoblastic leukemia. The New England Journal of Medicine. Nov. 11, 1982;307(20):1251-54.

Curtis, et al. Risk of lymphoproliferative disorders after bone marrow transplantation: A multi-institutional study. Blood. 1999;94:2208-2216.

Dakshinamurty, et al. Ternary liquid equilibrium systems ethanol-water-methyl isobutyl carbinol and acetic acid-water-ethyl butyrate. J. Chem. Eng. Data. 1972;17(3):379-383.

Daniel. Pharmacokinetic study of butyric acid administered in vivo as sodium and arginine butyrate salts. Clinica Chimica Acta. 1989;181:255-264.

Dantchev, et al. Behavior of certain pyrimidine compounds of fumeric acid, and of malic acid with regard to the protection of red blood cells of the rabbit intoxicated with phenylhydrazine. Comportement de certain composés pyrimidiques, de l' acidew fumarique et de l' acide maléique â l' égard de las protection des globules rouges du lapin intoxiqut par la phénylhydrazine C.R. Acad. Sci. Hebd. Sceances Acad. Sci. D: Mar. 1967;264(11):1467-1470. (in French with English abstract).

De Bruin, et al. Detection of Epstein-Barr virus nucleic acid sequences and protein in nodal T-cell lymphomas: relation between latent membrane protein I positively and clinical course. Histopathology. 1993;23:509-509.

De Bruin, et al. Presence of Epstein-Barr virus in extranodal T-cell lymphomas: differences in relation to site. Blood. 1994;83(10):1612-1612.

De Vente, et al. Effects of adenosine and adenosine-analogs on adenylate cyclase activity in the rat adipocyte plasma membrane: comparison of the properties of the enzyme with Mn2* and Mg2+ as divalent cations. Molecular and Cellular Biology. 1981;40:65-73.

Dimaio, et al. Directed enzyme pro-drug gene therapy for pancreatic cancer in vivo. Surgery. Aug. 1994;116(2):205-13.

Donaldson, et al. Cytotoxicity of the anticancer agents cisplatin and taxol during cell proliferation and the cell cycle. Int J Cancer. Jun. 15, 1994;57(6):847-55.

Douillard, et al. Phase I trial of interleukin 2 (IL2) and arginine butyrate (ArgB) in metastatic colorectal cancer. Proc. Am. Assn. for Cancer Research. 1998;39:606. (Abstract only).

Dover, et al. Fetal hemoglobin levels in sickle cell disease and normal individuals are partially controlled by an x-linked gene located at Xp22.2. Blood. 1992;80(3):816-824.

Dover, et al. Induction of fetal hemoglobin production in subjects with sickle cell anemia by oral sodium phenylbutyrate. Blood. 1994;84:339-343.

Dover, et al. Ilydroxyurea induction of hemoglobin F production in sickle cell disease: relationship between cytotoxicity and F cell production. Blood. 1986;67:735-38.

Egorin, et al. Phase 1 clinical and pharmacokinetic study of hexamethylene bisacetamide (NSC 95580) administered as a five-day continuous infusion. Cancer. Res. 1987;47:617-623.

El Rassi, et al. Beta-thalassemia intermedia: an overview. Pediat Ann. May 2008;37(5):322-8.

El-Beshlawy, et al. Fetal globin induction in beta-thalassemia. Hemoglobin. 2009;33 Suppl 1:S197-203.

Ellis, et al. Synthetic human β-globin 5'HS2 constructs function as locus control regions only in multicopy transgene concatamers. EMBO Journal. 1993;12:127-134.

El-Nawawy, et al. Organic pesticides. II. (Arylthio) acetic acids, (arylenedithio) diacetic acids, and several of their S-alkylisothiuronium salts. Alexandria J. Agr. Res. 1970;16(2):173-184, (Abstract only).

Endo, et al. Differential induction of adult and fetal globin gene expression in the human CML cell subline KU-812F/33. J. Biochem. 1994;115:540-544.

European office action dated Aug. 11, 2010 for Application No. 6021311.3.

European search report dated Jun. 16, 2005 for Application No. 94930734.2.

European search report dated Jun. 9, 2009 for Application No. 6021311.3.

Evans, et al. A population-based case-control study of EBV and other viral antibodies among persons with Hodgkin's disease and their siblings. Int J Cancer. 1984;34:149-149.

Faller, et al. Arginine butyrate-induced susceptibility to ganciclovir in an Epstein-Barr Virus (EBV) associated lymphona. Am. Soc. of Hematology [Blood]. 1995;86(10)(1):342a.

Faller, et al. Arginine Butyrate-induced susceptibility to ganciclovir in Epstein-Barr virus (EBV)-associated lymphomas. Proceedings of the American Association for Cancer Research. 1996;37:411-412.

Faller, et al. Phase I/II trial of arginne butyrate to induce viral TK gene expression in Epstein-Barr Virus (EBV)-associated lymphomas. Proc. Am. Assn. for Cancer. Research. Mar. 2000;41:544. (Abstract only).

Fathallah, et al. Induction of fetal hemoglobin in the treatment of sickle cell disease. American Society of Hematology. 2006:55-62.

Faucitano, et al. Reaction of gases with irradiated organic solids. I. Preliminary results on propionamide, n-butyramide, and isobutyramide. Ric. Sci. 1967;37(12):1149-1155. (Abstract only).

Fibach, et al. Enhance fetal hemoglobin production by Phenylacetate and 4-Phenylbutyrate in erythroid precursors derived from normal donors and patients with sickle cell anemia and b-Thalassemia. Blood. 1993;82(7):2203-2209.

Flyer, et al. Retrovirus-induced changes in major histocompatibility complex antigen expression influence susceptibility to lysis by cytotoxic T lymphocytes. The Journal of Immunology. Oct. 1985;135(4):2287-92.

Forrester, et al. Molecular analysis of the human β-globin locus activation region. Proc. Natl. Acad. Sci. USA. 1989;86:5439-5443.

Foss, et al. Biomodulatory effects of butyric acid derivatives on leukemia and lymphoma cells. Blood. 1993; 82/10 Suppl. 1:564A. (1993) The American Society of Hematology, 35th Annual Meeting, Dec. 3-7, Abstract only.

Franco, et al. The effect of fetal hemoglobin on the survival characteristics of sickle cells. Blood. Aug. 1, 2006;108(3):1073-1076.

Franke, et al. [Experiences with alpha-aminoisobutyric acid in the treatment of wounds.] Zentralbl Chir. 1954;79(18):769-76.

Fraser, et al. Each hypersensitive site of the human β-globin locus control region confers a different developmental pattern of expression on the globin genes. Genes Dev. 1993;7:106-13.

Fritsch, et al. Characterisation of deletions which affect the expression of fetal globin genes in man. Nature. 1979;279:598-603.

Fucharoen, et al. Clinical and hematologic aspects of hemoglobin E [beta]—thalassemia. Curr Opin Hematol. Mar. 2000;7(2):106-112.

Fucharoen, et al. Hemoglobinopathies in Southeast Asia. Hemoglobin. 1987;11(1):65-88.

Fucharoen, et al. Thalassemia in SouthEast Asia: problems and strategy for prevention and control. Southeast Asian J Trop Med Public Health. Dec. 1992;23(4):647-55.

Fucharoen, et al. α- and β-Thalassemia in Thailand. Ann N Y Acad Sci. Jun. 30, 1998;850:412-4.

Gabbianeri, et al. Granulocyte-macrophage colony-stimulating factor reactivates fetal hemoglobin synthesis in erythroblast clones from normal adults. Blood. Dec. 1989;74(8):2657-67.

Garre, et al. Regulation of acetylcholinesterase expression in the K-562 cell line. Cancer Research. Sep. 1984;44:3749-3751.

Garsetti, et al. Butyric acid-induced differentiation of HL-60 cells increases the expression of a single lysophospholipase. Biochem. J. 1992;288:831-837.

Gaudet, et al. Differential regulation of arylamine and arylalkylamine N-acetyltransferases in human retinoblastoma (Y-79) cells. Neurochem Int. 1993;22(3):271-275.

Gerharz, et al. Modulation of invasive potential in different clonal subpopulations of a rat rhabdomyosarcoma cell line (BA-HAN-1) by differentiation induction. Clin. Exp. Metastasis. 1993;11(1):55-67.

Ghanayem, et al. Structure-activity relationships for the in vitro hematotoxicity of N-alkoxyacetic acids, the toxic metabolites of glycol ethers. Chem.-Biol. Interactions. 1989;70:339-352.

(56) References Cited

OTHER PUBLICATIONS

Gilbert, et al. A phase I dose escalation and bioavailability study of oral sodium phenylbutyrate in patients with refractory solid tumor malignancies. Clin Cancer Res. Aug. 2001;7(8):2292-300.
Ginder, et al. Activation of a chicken embryonic globin gene in adult erythroid cells by 5-Azacytidine and sodium butyrate. Proc. Natl. Acad. Science, USA. Jul. 1984;81:3954-3958.
Gladwin, et al. Pulmonary hypertension as a risk factor for death in patients with sickle cell disease. N Engl J Med. Feb. 26, 2004;350(9):886-895.
Gladwin. Unraveling the hemolytic subphenotype of sickle cell disease. Blood. Nov. 1, 2005;106(9):2925-2926.
Glaser, et al. Epstein-Barr virus-associated Hodgkin's disease: epidemiologic characteristics in international data. Int J Cancer. 1997;70(4):375-382.
Golub, et al. Induction of dormant HIV-1 by sodium butyrate: involvement of the TATA box in the activation of the HIV-1 promoter. AIDS. 1991;5(6):663-668.
Gredmark, et al. Active cytomegalovirus replication in patients with coronary disease. Scand Cardiovasc J. Aug. 2007;41(4):230-4.
Greenspan, et al. Replication of Epstein-Barr virus within the epithelial cells of oral "hairy" leukoplakia, an AIDS-associated lesion. N Engl J Med. 1985;313:1564-1564.
Gross, et al. B cell lymphoproliferative disorders following hematopoietic stem cell transplantation. Risk factors, treatment and outcome. Bone Marrow Transplant. 1999;23:251-258.
Grossi, et al., Effects of monosaccharide esters of butyric acid on the synthesis of hemoglobin T chain and erythroleukemis cell line, Abstract of ASH Annual Meeting, Seattle, WA, Dec. 1-5, 1995.
Grufferman, et al. Hodgkin's disease in siblings. N Engl J Med. 1977;296:248-250.
Guilbaud, et al. Effects of differentiation-inducing agents on maturation of human MCF-7 breast cancer cells. Journal of Cellular Physiology. 1990;145:162-172.
Gum, et al. Effects of sodium butyrate on human colonic adenocarcinoma cells. The Journal of Biological Chemistry. Jan. 25, 1987;262(3):1092-1097.
Hahn, et al. Therapeutic outcome of Epstein-Barr virus positive T/NK cell lymphoma in the upper aerodigestive tract. Yonsei Med J. 2002;43:175-182.
Hanto, et al. Epstein-Barr virus-induced polyclonal and monoclonal B-cell lymphoproliferative diseases occurring after renal transplantation. Ann Surg. 1983;198:356-369.
Harabuchi, et al. Epstein-Barr virus in nasal T-cell lymphomas in patients with lethal midline granuloma. Lancet. 1990;335:128-128.
Harig, et al. Treatment of diversion colitis with short-chain-fatty acid irrigation. N. Engl. J. Med. 1989;320(1):23-28.
Henle, et al. Epstein-Barr virus and human malignancies. Adv Viral Oncol. 1985;5:201-238.
Henle, et al. Relation of Burkitt's tumor-associated herpes-type virus to infectious mononucleosis. Proc Natl Acad Sci USA. 1968;58:94-101.
Herbst, et al. Epstein-Barr virus latent membrane protein expression in Hodgkin and Reed-Sternberg cells. Proc Natl Acad Sci USA. 1991;88:4766-4766.
Ho, et al. Presence of Epstein-Barr virus DNA in nasal lymphomas. Hematol Oncol. 1990;8:271-271.
Hock, et al., Retrovirus-mediated transfer and express of drug resistance genes in human hematopoietic progenitor cells. Nature. Mar. 20, 1986;320:275-277.
Hoessly, et al. Factors responsible for variable reported lineages of HL-60 cells induced to mature with butyric acid. Cancer Research. Jul. 1, 1989;49:3594-97.
Hoey, et al. Molecular cloning and functional analysis of *Drosophila* TAF110 reveal properties expected of coactivators. Cell. 1993;72:247-60.
Hsu, et al. Epstein-Barr virus-associated malignancies: epidemiologic patterns and etiologic implications. Crit Rev Oncol Hematol. 2000;34:27-53.

Huang, et al. The hematopoietic growth factor KL is encoded by the SI locus and is the ligand of the o-kit receptor, the gene product of the W locus. Cell. Oct. 5, 1990;63:225-233.
Huber, et al. In vivo antitumor activity of 5-fluorocytosine on human colorectal carcinoma cells genetically modified to express cytosine deaminase. Cancer Res. Oct. 1, 1993;53(19):4619-26.
Huber, et al. Metabolism of 5-fluorocytosine to 5-fluorouracil in human colorectal tumor cells transduced with the cytosine deaminase gene: significant antitumor effects when only a small percentage of tumor cells express cytosine deaminase. Proc Natl Acad Sci U S A. Aug. 16, 1994;91(17):8302-6.
Hurford, et al. Gene therapy of metastatic cancer by in vivo retroviral gene targeting. Nat Genet. Aug. 1995;10(4):430-5.
Ikuta. Alterations in protein-DNA interactions in the y-globin gene promoter in response to butyrate therapy. Blood. Oct. 15, 1998;92(8);2924-33.
Inati. β-Thalassemia: the Lebanese experience. Clin Lab Haematol. 2006;(28)217-27.
International search report and written opinion dated Dec. 15, 2010 for PCT Application No. US10/50191.
International search report dated Jan. 2, 1995 for PCT Application No. US94/11565.
International search report dated Oct. 12, 2000 for PCT Application No. US1999/03014.
International search report dated Mar. 2, 2010 for PCT Application No. US2009/069035.
International search report dated Sep. 30, 2006 for PCT Application No. US1996/02907.
Jaffe, et al. Classification of cytotoxic T-Cell and natural killer cell lymphomas. Semin Hematol. 2003;40:175-184.
Jane, et al. Hemoglobin switching in man and chicken is mediated by a heteromeric complex between the ubiquitous transcription factor CP2 and a developmentally specific protein. The EMBO Journal. 1995;14(1): 97-105.
Jiang. cMYB is involved in the regulation of fetal hemoglobin production in adults. Blood. Aug. 1, 2006;108(3):1077-83.
Jiwa, et al. Epstein-Barr virus DNA in Reed-Sternberg cells of Hodgkin's disease is frequently associated with CR2 (EBV receptor) expression. Histopathology. 1992;21:51-51.
Johansson, et al. Epstein-Barr Virus (EBV)-associated antibody pattern in malignant lymphoma and leukemia. 1. Hodgkin's disease. Int J Cancer. 1970;5:450-450.
Johnson. L-carnitine for treatment of distal ulcerative colitis. Gastroenterology. Nov. 1992;103(5):1709-10.
Jones, et al. T-cell lymphomas containing Epstein-Barr virus DNA in patients with chronic Epstein-Barr virus infections. N Engl J Med. 1988;318(12):733-733.
Kanavaros, et al. Nasal T-cell lymphoma: a clinicopathologic entity associated with peculiar phenotype and with Epstein-Barr virus. Blood. 1983;81(10):2688-2688.
Karlsson, et al. Developmental regulation of human globin genes. Ann. Rev. Biochem. 1985;54:1071-1108.
Kato. Deconstructing sickle cell disease: reappraisal of the role of hemolysis in the development of clinical subphenotypes. Blood Rev. Jan. 2007;21(1):37-47.
Kattamis. Treatment of thalassemia with hydroxyurea: an indispensable alternative therapy. J Pediatr Hematol Oncol. Nov. 2007;29(11):729-730.
Kawa. Epstein-Barr virus-associated disease in humans. Int J Hematol. 2000;71:108-117.
Keedy, et al. A limited group of class I histone deacetylases acts to repress human immunodeficiency virus type 1 expression. J Virol. May 2009;83(10):4749-56.
Kim, et al. Modification of thermosensitivity of HeLa cells by sodium butyrate, dibutyrl cyclic adenosine 3':5'-monophosphate, and retinoic acid. Cancer Research. Feb. 1984;44:697-702.
Kirk, et al. Arginine stimulates wound healing and immune function in elderly human beings. Surgery. Aug. 1993;114(2):155-9; discussion 160.
Kleer, et al. Detection of Epstein-Barr virus in rapidly growing fibroadenomas of the breast in immunosuppressed hosts. Modern Pathol. 2002;15(7):759-764.

(56) References Cited

OTHER PUBLICATIONS

Koeffler. Induction of differentiation of human acute myelogenous leukemia cells: therapeutic implications. Blood. 1983;62:709-721.
Konstan, et al. Effect of high-dose ibuprofen in patients with cystic fibrosis. New England Journal of Medicine. 1995;332(13):848-854.
Korbjuhn, et al. Frequent latent Epstein-Barr virus infection of neoplastic T cells and bystander B cells in human immunodeficiency virus-negative European peripheral pleomorphic T-cell lymphomas. Blood. 1993;82(1):217-217.
Koren. Response to hydroxyurea therapy in β-thalassemia. Am J Hematol. 2008;83(5):366-70.
Krantis, et al. Augmentation of cysteamine-induced ulceration of rat duodenum by systemically administered g-Aminobutyric Acid (GABA). Digestive Diseases and Sciences. Aug. 1989;34(8m):1211-1216.
Kwong, et al. Natural killer cell lymphoma/leukemia: pathology and treatment. Hematol Oncol. 1997;15:71-79.
Labie, et al. Common haplotype dependency of high Gg-globin gene expression and high Hb F levels in b-thalassemia and sickle cell anemia patients. Proc. Natl. Acad. Sci. USA. Apr. 1985;82:2111-2114.
Landon, et al. Effect of sodium butyrate and other differentiation inducers of poorly differentiated human ovarian adenocarcinoma cell lines. Cancer Research Nov. 1, 1988;48:6161-6165.
Lea, et al. Butyramide and monobutyrin: growth inhibitory and differentiating agents. Anticancer Research. 1993;13:145-149.
Leavitt, et al. Butyric acid suppression of the in vitro neoplastic state of Syrian hamster cells. Nature. Jan. 1978;271(19):262-65.
Leder, et al. Differential of erythroleukemic cells in the presence of inhibitors of DNA synthesis. Science. Jul. 14, 1975;190:893-894.
Lee, et al. The association of Epstein-Barr virus with smooth-muscle tumors occurring after organ transplantation. N Engl J Med. 1995;332:19-25.
Leoncini, et al. Epstein-Barr virus and gastric cancer: data and unanswered questions. Int J Cancer. 1993;53:898-901.
Letvin, et al. Augmentation of fetal-hemoglobin production in anemic monkeys by hydroxyurea. The New England Journal of Medicine. 1984;310(14):869-873.
Ley, et al. 5-Azacytidine increases γ-globin synthesis and reduces the proportion of dense cells in patients with sickle cell anemia. Blood. 1983; 62(2):370-380.
Ley, et al. 5-Azacytidine selectively increases γ-globin synthesis in a patient with β+ thalassemia. The New England Journal of Medicine. 1982;307(24):1469-1475.
Liakopoulou, et al. Induction of fetal hemoglobin by propionic and butyric acid derivatives: correlations between chemical structure and potency of HbF induction. Blood Cells Mol Dis. 2002;29:48-56.
Liakopoulou, et al. Stimulation of fetal hemoglobin production by short chain fatty acids,' Blood. 1995;86(8):3227-3235.
Liakopoulou, et al. Structural features of short chain fatty acid-derived inducers of fetal hemoglobin. Abstract of ASH Annual Meeting, Seattle, WA, Dec. 1-5, 1995.
Lilbert, et al. Common vascular changes in the jugular vein of saline controls in continuous infusion studies in the beagle dog. Toxicol. Pathol. 2004;32:694-700.
Little. Metabolic persistence of fetal hemoglobin. Blood. Apr. 1, 1995;85(7):1712-18.
Lokeshwar, et al. Enhancement of radiation response of prostatic carcinoma by taxol: therapeutic potential for late-stage malignancy. Anticancer Res. Jan.-Feb. 1995;15(1):93-8.
MaGrath, et al. Breast cancer: a new Epstein-Barr virus-associated disease? J Nat Cancer Inst. 1999;91:1349-1350.
Maia, et al. Chronic, active Epstein-Barr virus infection. Curr Opin Hematol. 2000;7:59-63.
Mankidy, et al. Short-chain fatty acids induce g-globin gene expression by displacement of a HDAC3-NCoR repressor complex. Blood. 2006;108(9):3179-3186.
Mares, et al. Evaluation of gas chromatograph packings for the separation of butyric acid from serum-catalyzed hydrolysis of ethyl butyrate. Anal Biochem. Oct. 15, 1978;90(2):824-8.
Matalon, et al. The histone deacetylase inhibitor ITF2357 decreases surface CXCR4 and CCR5 expression on CD4(+) T-cells and monocytes and is superior to valproic acid for latent HIV-1 expression in vitro. J Acquir Immune Defic Syndr. May 1, 2010;54(1):1-9.
Mathias, et al. Ineffective erythropoiesis in β-thalassemia major is due to apoptosis at the polychromatophilic normoblast stage. Exp Hematol. 2000;28:1343-1353.
Maziarz, et al. Distinct effects of interferon-g and MHC class 1 surface antigen levels on resistance of the K562 tumor cell line. Cellular Immunology. 1990;130:329-38.
Maziarz, et al. The regulation of exogenous and endogenous class I MHC genes in a human tumor cell line, K562. Molecular Immunology. 1990;27:135-142.
McCafferty et al. Inhibition of butyric acid-induced colitis in mice by 16, 16-dimethyl prostaglandin E2. Inflammation Research. Mar. 1992;36 Suppl 1:C79-81.
McCafferty, et al. Short chain fatty acid-induced colitis in mice. Int. J. Tissue React. 1989;11(4):165-168.
McClain, et al. Association of Epstein-Barr virus with leiomyosarcomas in young people with AIDS. N Engl J Med. 1995;332:12-18.
McDonagh, et al. The Upstream Region of the Human γ-globin Gene Promoter. J. Biol. Chem. 1991;266:11965-74.
Medeiros, et al. Localization of Epstein-Barr viral genomes in angiocentric immunoproliferative lesions. Am J Surg Pathol. 1992;16:439-439.
Meijer, et al. Epstein-Barr virus and human T-cell lymphomas. Seminars in Cancer Biology. Aug. 1996;7(4):191-196.
Migliaccio, et al. Influence of recombinant hematopoietins and of fetal bovine serum on the globin synthetic pattern of human BFUe. Blood. 1990;76:1150-1157.
Miller, et al. Antibodies to butyrate-inducible antigens of Kaposi's Sarcoma-associated herpesvirus to patient with HIV-1 infection. The New England J. of Med. 1996;334(20):1292-1297.
Miller, et al. Clinical pharmacology of sodium butyrate in patients with acute leukemia. Eur J Cancer Clin Oncol. 1987;23(9):1283-1287.
Miller, et al. Influence of steel factor on hemoglobin synthesis in sickle cell disease. Blood. 1992;79:1861-1868.
Miller, et al. Toxicity of methoxyacetic acid in rats. Fundamental and Applied Toxicology. 1982; 2:158-160.
Modell, et al. Epidemiology of haemoglobin disorders in Europe: an overview. Scand J Clin Lab. 2007;67:39-70.
Moi, et al. Synergistic enhancement of globin gene expression by activator protein-1-like proteins. Proc. Natl. Acad. Sci. USA. 1990;87:9000-9004.
Morita, et al. Effect of sodium butyrate on alkaline phosphatase in HRT-18, a human rectal cancer cell line. Cancer Research. Nov. 1982;42:4540-4545.
Mueller, et al. Hodgkin's disease and Epstein-Barr virus. Altered antibody pattern before diagnosis. N Engl J Med. 1989;320:689-689.
Mueller, et al. In vivo footprinting of a muscle specific enhancer by ligation mediated PCR. Science. 1989;246:780-786.
Nagai, et al. Studies on the synogistic action and anti-ulcerous activity of cortisone-GABOB. Arzneim-Forsch. 1971;21(1):96-97.
Nagel, et al. F reticulocyte response in sickle cell anemia treated with recombinant human erythropoietin: a double-blind study. Blood. 1993;1:9-14.
Nagel, et al. Structural bases of the inhibitory effects of hemoglobin F and hemoglobin A2 on the polymerization of hemoglobin S. Biochemistry. 1979;76(2):670-72.
Naguib, et al. Effects of N,N-dimethylformanide and sodium butyrate on enzymes of pyrimidine metabolism in cultured human tumor cells. Leukemia Research. 1987;11(10):855-861.
Nathan. Regulation of fetal hemoglobin synthesis ini the hemoglobinopathics. Annals New York Academy of Sciences, Fifth Cooley's Symposium. 1985;445:177-187.
Newman, et al. Sodium n-butyrate enhancement of prostaglandin D2 antitumor efficacy. Biochemical Pharmacology. 1985;34(20):3771-3774.

(56) References Cited

OTHER PUBLICATIONS

Newman, et al., Induction of the insulin receptor and other differentiation markers by sodium butyrate in the Burkitt lymphoma cell, Raji. Biochemical and Biophysical Research Communications. May 30, 1989;161(1):101-106.
Ney, et al. Tandem AP-1-binding sites within the human β-globin dominant control region function as an inducible enhancer in erythroid cells. Genes Dev. 1990;4:993-1006.
Niedobitek, et al. Epstein-Barr virus gene expression in Hodgkin's disease. Blood. 1991;78:1628-1630.
Niedobitek. The role of Epstein-Barr virus in the pathogenesis of Hodgkin's disease. Ann Oncol. 1996;7:S11-S17.
Nienhuis, et al. Pharmacological manipulation of fetal hemoglobin synthesis in patients with severe β-Thalassemia. Ann N Y Acad Sci. vol. 445, Fifth Cooley's Anemia Symposium, Jun. 21, 1985:198-211.
Nisli, et al. Recombinant Human erythropoietin trial in thalassemia intermedia. J Trop Pediatr. 1996;42:330-34.
Noguchi, et al. Inhibition of sickle hemoglobin gelation by amino acids and related compounds. Biochemistry. 1978;17(25):5455-5459.
Noguchi, et al. Levels of fetal hemoglobin necessary for treatment of sickle cell disease. N Engl J Med. Jan. 14, 1988;96-99.
Novogrodsky, et al. Effect of polar organic componds on leukemic cells. Cancer. Jan. 1, 1983;51:9-14.
Nudel, et al. Different effects of chemical inducers on expression of β globin genes in Murine erythroleukemia cells. Proc. Natl. Acad. Sci. USA. Mar. 1977;74(3):1100-1104.
Nudelman, et al. Novel anticancer prodrugs of butyric acid. 2. J Med Chem. Feb. 21, 1992;35(4):687-94.
Oldfield, et al. Gene therapy for the treatment of brain tumors using intra-tumoral transduction with the thymidine kinase gene and intravenous ganciclovir. Hum Gene Ther. Feb. 1993;4(1):39-69.
Oliva, et al. Histone hyperacetylation can induce unfolding of the nucleosome core particle. Nuc. Acids Res: 1990;18:2739-2747.
O'Malley, et al. Adenovirus-mediated gene therapy for human head and neck squamous cell cancer in a nude mouse model. Cancer Res. Mar. 1, 1995;55(5):1080-5.
Ormandy, et al. Coordinate regulation of oestrogen and prolactin receptor expression by sodium butyrate in human breast cancer cells. Biochemical and Biophysical Research Communications. Jan. 31, 1992;182(2):740-745.
Osato, et al. Epstein-Barr virus and gastric carcinoma. Semin Cancer Biol. 1996;7:175-182.
Pace, et al. Short-chain fatty acid derivatives induce fetal globin expression and erythropoiesis in vivo. Blood. Dec. 15, 2002;100(13):4640-8.
Pagano. Epstein-Barr virus: the first human tumor virus and its role in cancer. Proc Assoc Am Physicians. 1999;111:573-580.
Parise, et al. Liquid chromatography-mass spectrometric assay for quantitation of the short-chain fatty acid, 2,2-dimethylbutyrate (NSC 741804), in rat plasma. J Chromatogr B Analyt Technol Biomed Life Sci. Feb. 1, 2008;862(1-2):168-74.
Partington, et al. Human globin gene transcription in injected xenopus cocytes: enhancement by enhancement by sodium butyrate. Embo J. Dec. 1, 1984;3(12):2787-92.
Patel, et al. Transcriptional activation potential of normal and tumor-associated myb isoforms does not correlate with their ability to block GCSE—induced terminal differentiation, of murine myeloid precursor cells. Oncogene. 1996;13:1197-1208.
Perez, et al. Bryostatin-1 Synergizes with Histone Deacetylase Inhibitors to Reactivate HIV-1 from Latency. Curr HIV Res. Sep. 1, 2010;8(6):418-29.
Perrine, et al. A phase 1,2 trial of arginine butyrate and ganciclovir in patients with Epstein-Barr virus-associated lymphoid malignancies. Blood. 2007;109(6):2571-2578.
Perrine, et al. A short-term trial of butyrate to stimulate fetal-globin-gene expression in the β-globin disorders. N. Engl. J. Med. 1993;328:81-86.
Perrine, et al. An Interleukin 2/Sodium Butyrate combination as immunotherapy for rat colon cancer peritoneal carcinomatosis. Gasteroenterology. 1994;107:1697-1708.
Perrine, et al. Benign sickle-cell anaemia. Lancet. Dec. 2, 1972:1163-67.
Perrine, et al. Butryic acid analogues augment γ globin gene expression in neonatal erthroid progenitors. Biochemical and Biophysical Research Communication. 1987;148:694-700.
Perrine, et al. Butyrate derivatives, new agents for stimulating fetal globin production in the β-globin disorders. The American Journal of Pediatric Hematology/Oncology. 1994;16(1):67-71.
Perrine, et al. Butyrate infusions in the ovine fetus delay the biologic clock for globin gene switching. Proc. Natl. Acad. Sci. USA. 1988;85:8540-8542.
Perrine, et al. Butyrate-induced reactivation of the fetal globin genes: a molecular treatment for the beta-hemoglobinopathies. Experientia. Feb. 15, 1993;49(2):133-7.
Perrine, et al. HQK-1001 has additive HbF-inducing activity in combination with hydroxyurea & decitabine. Slides presented at ASH Annual Meeting and Exposition. Dec. 2009.
Perrine, et al. Induction of fetal globin in b-thalassemia: cellular obstacles and molecular progress. Ann N.Y. Acad. Sci. 2005;1054:257-265.
Perrine, et al. Isobutyramide, an orally bioavailable butyrate analogue, stimulates fetal globin gene expression in vitro and in vivo. British Journal of Hematology. 1994:555-561.
Perrine, et al. Natural history of sickle cell anemia in Saudi Arabs. Ann Intern Med. 1978;88(1):1-6.
Perrine, et al. Phase 1 clinical testing of HQK-1001, a novel oral fetal globin gene inducer. Abstract from ASH Annual Meeting and Exposition. Dec. 2008.
Perrine, et al. Phase 1 clinical testing of HQK-1001, a novel oral fetal globin stimulant. Slides presented at ASH Annual Meeting and Exposition. Dec. 2008.
Perrine, et al. RH-Activin increases erythroid progenitor growth and Hb F in childhood red cell failure syndromes and hemoglobinopathies. Blood. 1989;74(7), Suppl. 1: Abstract p. 114a.
Perrine, et al. Sodium butyrate enhances fetal globin gene expression in erythroid progenitors of patients with Hb SS and beta thalassaemia. Blood. 1989;74:454-459.
Perrine. Fetal globin induction—can it cure beta thalassemia? Hematology. 2005:38-44.
Planchon, et al. Differential effects of butyrate derivatives on human breast cancer cells grown as organotypic nodules in vitro and as xenografts in vivo. In Vivo. Nov.-Dec. 1992;6(6):605-10.
Planchon, et al. Morphology and intermediate filament composition of human mammary epithelial cells treated with stable butyrate derivative. Anticancer Res. Nov.-Dec. 1992;12(6B):2315-20.
Planchon, et al. New stable butyrate derivatives alter proliferation and differentiation in human mammary cells. Int J Cancer. May 30, 1991;48(3):443-9.
Platt, et al. Mortality in sickle cell disease—life expectancy and risk factors for earlydeath. N. Engl. J. Med. 1994;330:1639-1644.
Platt, et al. Pain in sickle cell disease. N Engl J Med. Jul. 4, 1991;325(1):11-16.
Pootrakul, et al. A correlation of erythrokinetics, ineffective erythropoiesis, and erythrod precursor apoptosis in Thai patients with thalassemia. Blood. Oct. 1, 2000;96(7):2606-12.
Pouillart, et al. Enhancement by stable butyrate derivatives of antitumor and antiviral actions of interferon. Int. J. Cancer. 1992;51:596-601.
Powars, et al. Is there a threshold level of fetal hemoglobin that ameliorates morbidity in sickle cell anemia? Blood. Apr. 1984;63(4):921-926.
Prasad. Butyric acid a small fatty acid with diverse biological functions. Life Sciences. 1980;27:1351-1358.
Prochownik, et al. Deregulated expression of o-myc by murine erythroleukemia cells prevents differentiation. Nature. Aug. 28, 1986;322:848-50.
Rachmilewitz, et al. The role of recombinant human erythropoietin in the treatment of thalassemia. Ann N Y Acad Sci. vol. 850 Issue Cooley's Anemia: Seventh Symposium. Feb. 7, 2006:129-138. (Published Online).

(56) References Cited

OTHER PUBLICATIONS

Reiss, et al. Induction of tumor cell differentiation as a therapeutic approach: preclinical models for hematopoietic and solid neoplasms. Cancer Treatment Reports. Jan. 1986;70(1):201-218.
Rephaeli, et al. Anti-lekemic effect of butyrate in-vitro and in-vivo and the development of a potent butyrate prodrug. Blood. 1990;76:115a.
Reynolds. The Extra Pharmacopoeia, 29th edition, 1989:1359.
Rickinson, et al. Epstein-Barr virus. In Fields Virology, vol. 2, 3rd Ed., B. N. Fields, D. M. Knipe, and P. M. Howley, eds. Lippincott-Raven, Philadelphia. 1996:2397-2446.
Rius, et al. The induction of vimentin gene expression by sodium butyrate in human promonocytic leukemia U937 cells. Experimental Cell Research. 1990;188:129-134.
Rodgers, et al. Augmentation by erythropoietin of the fetal-hemoglobin response to hydroxyurea in sickle cell disease. The New England Journal of Medicine. 1993;328(2):73-80.
Roediger, et al. Selective reduction of fatty acid oxidation in colonocytes: correlation with ulcerative colitis. Lipids. 1990;25(10):646-652.
Rowe, et al. Colonic short-chain fatty acids: fuel from the lumen? Gastroenterology. Jul. 1992;103(1):336-8.
Rowinsky, et al. Prolonged infusion of hexamethylene bisacetamide: a phase I and pharmacological study. Cancer Res. 1987;47:5788-5795.
Rubenstein, et al. A pilot clinical trial of oral sodium 4-phenylbutyrate (Buphenyl) in DELTAF508-homozygous cystic fibrosis patients: Partial restoration of nasal epithelial CFTR function. American Journal of Respiratory and Critical Care Medicine. Feb. 1998;157(2):484-490.
Rubenstein, et al. In vitro pharmacologic restoration of CFTR-mediated chloride transport with sodium 4-phenylbutyrate in cystic fibrosis epithelial cells containing delta F508-CFTR. J Clin Invest. Nov. 15, 1997;100(10):2457-2465.
Rund, et al. B-Thalassemia. N Engl J Med. Sep. 15, 2005;353(11):1135-46.
Sachs. Cell differentiation and bypassing of genetic defects in the suppression of malignancy. Cancer Research. 1987;47:1981-1986.
Sadaie, et al. Induction of developmentally programmed cell death and activation of HIV by sodium butyrate. Virology. 1994;202:513-518.
Safaya, et al. Augmentation of g-globin gene promoter activity by carboxylic acids and components of the human β-glovin locus control region. Blood. Dec. 1, 1994;84(II):3929-3925.
Scheppach, et al. Effect of butyrate enemas on the colonic mucosa in distal ulcerative colitis. Gastroenterology. Jul. 1992;103(1):51-6.
Scherr, et al. School contact among persons with Hodgkin's disease. Am J. Epidemiol. 1984;120:29-29.
Seifter, et al. An outlier theory of cancer curability—tumor cell differentiation as a therapeutic goal. The American Journal of Medicine. Oct. 1987;83:757-60.
Sher, et al. Rapid healing of chronic leg ulcers during arginine butyrate therapy in patients with sickle cell disease and thalassemia. Blood. Oct. 1, 1994;84(7):2378-80.
Shibata, et al. Epstein-Barr virus-associated non-Hodgkin's lymphoma in patients infected with the human immunodeficiency virus. Blood. 1993;91:2101-2109.
Singer, et al. Fetal haemoglobin augmentation in E/β0 thalassaemia: clinical and haematological outcome. Br J Haematol. 2005;131:378-88.
Slamon, et al. Expression of cellular oncogenes in human malignancies. Science. 1984;224:256-262.
Speck, et al. Infection of breast epithelial cells with Epstein-Barr virus via cell-to-cell contact. J Nat Cancer Inst. 2000;92:1849-1851.
Sripichai, et al. A scoring system for the classification of β-thalassemia/Hb E disease severity. Am J Hematol. Jun. 2008;83(6):482-4.
Stamatoyannopolous, et al. Fetal hemoglobin induction by acetate, a product of butyrate catabolism. Blood. Nov. 1, 1994;84(9):3198-204.
Stamatoyannopolous, et al. The regulation of hemoglobin switching. The Johns Hopkins University Press. 1990:425-426.
Steinberg, et al. Effect of hydroxyurea on mortality and morbidity in adult sickle cell anemia. JAMA. Apr. 2, 2003;289(13):1645-51.
Steinberg, et al. Fetal hemoglobin in sickle cell anemia: determinants of response to hxdroxyurea. Blood. Feb. 1, 1997;89(3):1078-1088.
Steinberg, et al. Pharmacologic modulation of fetal hemoglobin. Medicine. 2001;80(5):328-44.
Steinberg. Predicting clinical severity in sickle cell anaemia. British Journal of Haematology. 2005;129(4):465-81.
Su, et al. Aggressive peripheral T-cell lymphomas containing Epstein-Barr viral DNA: A clinicopathologic and molecular analysis. Blood. 1991;77:799-808.
Sutherland, et al. Induction of the expression of HLA class I antigens on K562 by interferons and sodium butyrate. Human Immunology. 1985;12:65-73.
Swinnen. Overview of posttransplant B-cell lymphoproliferative disorders. Semin Oncol. 1999;26:21-25.
Takahashi, et al. Differentiation of cultured friend leukemia cells induced by short-chain fatty acids. Gann. Oct. 1975;66:577-580.
Tang, et al. Memory of butyrate induction by the moloney murine sarcoma virus enhancer-promoter element. Biochem and Biophys Res. Comm. 1992;189(1):141-147.
Testa. Apoptotic mechanisms in the control of erythropoiesis. Leukemia. 2004;18:1176-99.
The Merck Index of Chemicals and Drugs, 7th edition, 1960:434.
Torrealba-De Ron, et al. Perturbations in the erythroid marrow progenitor cell pools may play a role in the augmentation of HbF by 5-azacytidine. Blood. 1984;63(1):201-210.
Toussirot, et al. Epstein-Barr virus in autoimmune diseases. Best Practice & Research Clinical Rheumatology. 2008;22(5):883-896.
Tsao, et al. Differential effects of sodium butyrate, dimethyl sulfoxide, and retinoic acid on membrane-associated antigen, enzymes, and glycoproteins of human rectal adehocarcinoma cells. Cancer Research. Mar. 1982;42:1052-1058.
Tuan, et al. Different 3' end points of deletions causing δβ-thalassemia and hereditary persistence of fetal hemoglobin: Implications for the control of γ-globin gene expression in man. Proc. Natl. Acad. Sci. USA. 1983;80:6937-6941.
Ulrich. Function of normal and mutated gamma-globin gene promoters in electroporated K562 erythroleukemia cells. Blood. 1990;75:990-99.
Vichinsky, et al. Changes in the epidemiology of thalassemia in north america: a new minority disease. Pediatrics. Dec. 2005;116(6):e818-e25.
Vichinsky. Changing patterns of thalassemia worldwide. Annals of the N.Y. Academy of Science. 2005;1054:18-24.
Vichinsky. Hemoglobin E Syndromes. Hematology/the Education Program of the American Society of Hematology. 2007:79-83.
Vile, et al. Systemic gene therapy of murine melanoma using tissue specific expression of the HSVtk gene involves an immune component. Cancer Res. Dec. 1, 1994;54(23):6228-34.
Volkov, et al. Cinnamic acid in analytical chemistry. X Determination of scandium as cinnamate and its separation from the rare earth elements and yttrium. Zh. Anal. Khim 1967;22(3):340-345. (Abstract only).
Walsh, et al. Combination of drug and gene delivery by gelatin nanospheres for the treatment of cystic fibrosis. Proceedings of the International Symposium on Controlled Release of Bioactive Materials, U.S., Deerfield, IL, controlled Release Soc., vol. Symp, 24, Jun. 15, 1997:75-76.
Wasseman, et al. Different effects of sodium butyrate and dimethylsulfoxide on gamma-glutamyl transpeptidase and allcaline phosphatase activities in MCF-7 breast cancer cells. Expl. Cell Biol. 1987;55:189-193.
Watkins, et al. Choleretic effect of structural analogs of valproic acid in the rat. Res Commun Chem Pathol Pharmacol. Mar. 1983;39(3):355-66.
Watson, et al. Butyrate acid in the treatment of cancer. The Lancet. 1933:746-748.
Weatherall, et al. A model for the persistence or reactivation of fetal haemoglobin production. The Lancet. Sep. 25, 1976;308(7987):660-63.
Weiss, et al. Detection of Epstein-Barr virus in Reed-Sternberg cells of Hodgkin's disease. N Engl J Med. 1989;320(8):502-502.

(56) References Cited

OTHER PUBLICATIONS

Weiss, et al. Epstein-Barr viral DNA in tissues of Hodgkin's disease. Am J Pathol. 1987;129:86-86.

Weiss, et al. Epstein-Barr virus and Hodgkin's disease. A correlative in situ hybridization and polymerase chain reaction study. Am J Pathol. 1991;139:1259-1259.

Williams, et al. Identification of a Ligand for the o-kit Proto-Oncogene. Cell. Oct. 5, 1990;63:167-174.

Winichagoon, et al. β-Thalassemia in Thailand. Annals of the New York Academy of Sciences. 1990;612:31-42.

Wittstruck, et al. A nuclear magnetic resonance study of transmission of electronic effects. Ethylbenzenes, dihydrocinnamic acids, and cis- and trans-cinnamic acids. J. Am Chem. Soc. 1967;89(15):3803-3809. (Abstract only).

Wood, et al. Hb F Synthesis in Sickle Cell Anaemia: a Comparison of Saudi Arab Cases with those of African Origin. British Journal of Haematology. 1980;45:431-445.

Wu, et al. Detection of EBV gene expression in Reed-Sternberg cells of Hodgkin's disease. Int J Cancer. 1990;46:801-801.

Yeivin, et al. Sodium butyrate selectively induces transcription of promoters adjacent to the MoMSV viral enhancer. Gene. Jul. 15, 1992;116(2):159-64.

Young, et al. Phase I trial and clinical pharmacological evaluation of hexamethylene bisacetamide administration by ten-day continuous intravenous infusion at twenty-eight-day intervals. Cancer Res. 1988;48:7304-7309.

Zeitlin, et al. Evidence of CFTR function in cystic fibrosis after systemic administration of 4-phenylbutyrate. Mol Ther. Jul. 2002;6(1):119-26.

Zhang, et al. Effect of (E)-5-(2-bromovinyl)-2'-deoxyuridine on several parameters of Epstein-Barr virus infection. J Gen Virol. Jan. 1984;65 (Pt 1):37-46.

Zituik, et al. The Silencing of .gamma.-Globin Gene Exin a .beta.-Globin Locus Yac can be Arrested by a .alpha.-Aminobutyric Acid. Abstract of ASH Annual Meeting, Seattle, Washington, Dec. 1-5, 1995.

Zsebo, et al. Identification, purification and biological characterization of hematopoietic stem cell factor from buffalo rat liver-conditioned medium. Cell. Oct. 5, 1990;63:195-201.

Zsebo, et al. Stem cell factor is encoded at the si locus of the mouse and is the ligand for the o-kit tyrosine kinase receptor. Cell. Oct. 5, 1990;63:213-224.

zur Hausen, et al., EBV DNA in biopsies of Burkitt tumours and anaplastic carcinomas of the nasopharynx. Nature. 1970;228(5276):1056-1058.

PCT/US10/59584 Search Report and Written Opinion mailed Feb. 11, 2011.

EP 10184726 Search Report mailed Jan. 20, 2011.

"Guidance for Industry. Estimating the Maximum Safe Starting Dose in Initial Clinical Trials for Therapeutics in Adult Healthy Volunteers," U.S. Department of Health and Human Services—FDA, Jul. 2005, XP002691340, Retrieved from the Internet: URL:http://www.fda.gov/downloads/Drugs/GuidanceComplianceRegulatoryInformation/Guidances/UCM078932.pdf.

Extended European Search Report dated Feb. 15, 2013 for Application No. 10836658.4.

\* cited by examiner

METHODS AND LOW DOSE REGIMENS FOR TREATING RED BLOOD CELL DISORDERS

CROSS-REFERENCE TO RELATED APPLICATIONS

This application claims priority under 35 U.S.C. 119(e) of U.S. Provisional Patent Application Ser. No. 61/411,369, filed Nov. 8, 2010; of U.S. Provisional Patent Application Ser. No. 61/367,326, filed Jul. 23, 2010; of U.S. Provisional Patent Application Ser. No. 61/312,090 filed Mar. 9, 2010; of U.S. Provisional Patent Application Ser. No. 61/306,376 filed Feb. 19, 2010; of U.S. Provisional Patent Application Ser. No. 61/295,650 filed Jan. 15, 2010; and of U.S. Provisional Patent Application Ser. No. 61/267,727 filed Dec. 8, 2009; the contents of which are incorporated herein by reference in their entirety.

STATEMENT AS TO FEDERALLY SPONSORED RESEARCH

Certain inventions described herein were made with the support of the United States government under grant DK-52962 by the National Institutes of Health.

BACKGROUND OF THE INVENTION

Anemia, a red blood cell disorder, can be grossly defined as a reduction in the ability of blood to transport oxygen. Although red blood cell disorders may be caused by certain drugs and immune system disorders, the majority are caused by genetic defects in the expression of hemoglobin. Disorders of hemoglobin synthesis include deficiencies of globin synthesis such as thalassemia syndromes and structural abnormalities of globin such as sickle cell syndromes and syndromes associated with unstable hemoglobins.

Fetal globin (also known as gamma globin) normally combines with alpha globin chains prenatally to form fetal hemoglobin (HbF). Fetal globin is replaced by beta globin after birth, which then combines with alpha globin to form adult hemoglobin A. Fetal globin performs the same function as beta globin, and can combine with the alpha chains to generate a healthy form of hemoglobin thereby reducing high concentrations of unmatched alpha globin chains.

The various types of beta thalassemias are syndromes resulting from mutations, which produce a deficiency of beta globin chains. In beta thalassemia, the unmatched alpha globin chains aggregate inside red blood cells (RBCs) and their progenitors, causing the premature destruction of RBCs and RBC progenitors, which results in anemia, transfusion-dependence, iron overload, organ failure, and early death.

In sickle cell disease (SCD), one amino acid substitution in the beta globin chain results in the generation of sickling hemoglobin (HbS), which allows polymerization with repeated cycles of deoxygenation. Polymerization results in "sickling" of RBCs. The sickled RBCs undergo hemolysis, while adhesive sickled RBCs occlude the microcirculation, provoking widespread tissue ischemia and organ infarction. The natural history of SCD is marked by painful crises, acute chest syndrome, and eventual potentially life-threatening sequelae, including renal insufficiency, retinitis, osteonecrosis, osteomyelitis, aplastic crises, functional asplenism, stroke, priapism, and severe pulmonary hypertension.

The disclosure herein provides novel methods and compositions for raising fetal hemoglobin in a patient with a blood disorder, including beta thalassemias and sickle cell disease.

SUMMARY OF THE INVENTION

Provided herein are methods for increasing the percentage of fetal hemoglobin in the blood of a subject, comprising administering to said subject: a) 2,2-dimethylbutyrate (DMB) as the free acid, a pharmaceutically acceptable salt, or ester thereof, and b) one or more agents selected from the group consisting of hydroxyurea, decitabine, and an HDAC inhibitor, wherein after the administration the percentage of fetal hemoglobin in the blood of the subject increases. In some embodiments, the percentage of fetal hemoglobin in the blood of a subject increases after one week of administering as compared to baseline. In other embodiments, the percentage of fetal hemoglobin in the blood of a subject increases after two weeks of administering as compared to baseline. In certain embodiments, the percentage of fetal hemoglobin in the blood of a subject increases after four weeks of administering as compared to baseline. In some embodiments, the percentage of fetal hemoglobin in the blood of a subject increases after one day of administering as compared to baseline. In certain embodiments, the percentage of fetal hemoglobin in the blood of a subject increases after 3 days of administering as compared to baseline.

In some embodiments of the methods for increasing the percentage of fetal hemoglobin, the subject has been diagnosed with a blood disorder or anemia. In certain embodiments, the blood disorder is a sickle cell syndrome. In some embodiments, the blood disorder is a beta thalassemia syndrome.

In some embodiments, the 2,2-dimethylbutyrate is administered as sodium 2,2-dimethylbutyrate. In certain embodiments, DMB is administered orally. In some embodiments, the HDAC inhibitor is MS-275. In certain embodiments, the administration of the one or more agents is orally. In some embodiments, the administration of the DMB and the one or more agents is orally. In certain embodiments, the DMB and the one or more agents are administered in a combined oral dosage form.

In some embodiments, the total daily dose of DMB does not exceed 100 mg/kg, does not exceed 90 mg/kg, does not exceed 80 mg/kg, does not exceed 70 mg/kg, does not exceed 60 mg/kg, does not exceed 50 mg/kg, does not exceed 40 mg/kg, does not exceed 35 mg/kg, does not exceed 30 mg/kg, does not exceed 25 mg/kg, does not exceed 20 mg/kg, does not exceed 15 mg/kg, does not exceed 10 mg/kg, or does not exceed 5 mg/kg. In certain embodiments, the total daily dose of DMB is between 10 and 60 mg/kg, between 20 and 70 mg/kg, between 30 and 80 mg/kg, between 40 and 90 mg/kg, or between 50 and 100 mg/kg In certain embodiments, the dose of hydroxyurea does not exceed 35 mg/kg/day. In some embodiments, the dose of hydroxyurea is less than 35 mg/kg/day, less than 30 mg/kg/day, less than 25 mg/kg/day, less than 20 mg/kg/day, less than 15 mg/kg/day, less than 10 mg/kg/day, or less than 5 mg/kg/day. In certain embodiments, the dose of hydroxyurea is less than 90% of the maximum tolerated dose. In other embodiments, the dose of hydroxyurea is less than 80%, less than 70%, less than 60%, less than 50%, less than 40%, less than 30%, less than 20%, less than 10% of the maximum tolerated dose.

In some embodiments, the dose of decitabine does not exceed 15 mg/m$^2$. In certain embodiments, the dose of decitabine is less than about 15 mg/m$^2$, less than about 10 mg/m$^2$, less than about 5 mg/m$^2$, less than about 3 mg/m$^2$, less than about 2 mg/m$^2$, or less than about 1 mg/m$^2$. In other embodiments, decitabine is administered orally at a dose of not more than about 240 mg, not more than about 180 mg, not more than about 120 mg, not more than about 60 mg, or not more than about 30 mg.

In certain embodiments, the dose of MS-275 does not exceed 6 mg/m² administered weekly. In some embodiments, the dose of MS-275 is less than about 6 mg/m², less than about 5 mg/m², less than about 4 mg/m², less than about 3 mg/m², less than about 2 mg/m², or less than about 1 mg/m² administered weekly. In certain embodiments, MS-275 is administered daily.

In certain embodiments, the plasma concentration of DMB does not exceed a concentration of 90 μg/mL of DMB. In other embodiments, the plasma concentration does not exceed a concentration of 120 μg/mL of DMB. In certain embodiments, the plasma concentration of DMB does not exceed a concentration of 150 μg/mL. In some embodiments, the plasma concentration of DMB does not exceed a concentration of 200 μg/mL. In certain embodiments, the plasma concentration of DMB does not exceed a concentration of 250 μg/mL. In some embodiments, the plasma concentration of DMB is between 20 μg/mL and 90 μg/mL, or between 25 μg/mL and 120 μg/mL, between 30 μg/mL and 150 μg/mL, or between 30 μg/mL and 250 μg/mL. In certain embodiments, the maximum plasma concentration of DMB is less than 350 μg/mL, less than 250 μg/mL, less than 200 μg/mL, less than 150 μg/mL, less than 140 μg/mL, less than 130 μg/mL, less than 120 μg/mL, less than 110 μg/mL, less than 100 μg/mL, less than 90 μg/mL, less than 80 μg/mL, less than 70 μg/mL, less than 60 μg/mL, less than 50 μg/mL, less than 40 μg/mL, less than 30 μg/mL, or less than 20 μg/mL.

In certain embodiments, the amount of fetal globin in the blood of the subject increases. In some embodiments, the number of F-cells in the blood of the subject increases. In certain embodiments, the number of F-reticulocytes in the blood of the subject increases. In some embodiments, the amount of fetal hemoglobin in the blood of the subject increases. In certain embodiments, the amount of total hemoglobin in the blood of the subject increases. In some embodiments, the percentage of reticulocytes in the blood of the subject increases. In certain embodiments, the number of reticulocytes in the blood of the subject increases. In some embodiments, hematocrit increases. In certain embodiments, red blood cell production increases.

In some embodiments, the administration of DMB is by pulsed administration. In certain embodiments, the pulsed administration comprises administering DMB for about 8 weeks, followed by not administering DMB for about 4 weeks. In some embodiments, the pulsed administration comprises administering DMB for about 6 weeks, followed by not administering DMB for about 2 weeks. In certain embodiments, the pulsed administration comprises administering DMB for about 4 weeks, followed by not administering DMB for about 2 weeks. In some embodiments, the pulsed administration comprises administering DMB for about 2 weeks, followed by not administering DMB for about 2 weeks. In some embodiments, pulsed administration comprises pulses of administering DMB for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In certain embodiments, pulsed administration comprises intervals of not administering DMB of about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In some embodiments, administration is continuous. In certain embodiments, administration is for the lifetime of the subject.

In some embodiments, the subject is a mammal. In certain embodiments, the mammal is an animal. In some embodiments, the animal is a horse. In certain embodiments, the mammal is a human. In some embodiments, the human is a child. In certain embodiments, the human is under the age of 18. In some embodiments, the human is under the age of 10. In some embodiments, the human is under the age of 2.

Also provided herein are methods for increasing the percentage of fetal hemoglobin in the blood of a subject comprising administering to said subject DMB as the free acid, a pharmaceutically acceptable salt, or ester thereof, wherein the total daily dose of DMB is not more than 40 mg/kg, and wherein after the administration the percentage of fetal hemoglobin in the blood of the subject increases. In certain embodiments, the subject has been diagnosed with a beta thalassemia. In some embodiments, the total daily dose of DMB does not exceed 40 mg/kg, does not exceed 35 mg/kg, does not exceed 30 mg/kg, does not exceed 25 mg/kg, does not exceed 20 mg/kg, does not exceed 15 mg/kg, does not exceed 10 mg/kg, or does not exceed 5 mg/kg. In certain embodiments, the total daily dose of DMB is between 5 and 25 mg/kg, between 10 and 30 mg/kg, between 20 and 40 mg/kg, between 5 and 20 mg/kg, between 10 and 25 mg/kg, between 15 and 30 mg/kg, between 20 and 35 mg/kg, or between 25 and 40 mg/kg. In some embodiments, the total daily dose of DMB is less than about 40 mg/kg, less than about 35 mg/kg, less than about 30 mg/kg, less than about 25 mg/kg, less than about 20 mg/kg, less than about 15 mg/kg, or less than about 10 mg/kg.

In certain embodiments, the plasma concentration of DMB does not exceed a concentration of 90 μg/mL of DMB. In other embodiments, the plasma concentration does not exceed a concentration of 120 μg/mL of DMB. In certain embodiments, the plasma concentration of DMB does not exceed a concentration of 150 μg/mL. In some embodiments, the plasma concentration of DMB is between 20 μg/mL and 90 μg/mL, or between 25 μg/mL and 120 μg/mL, or between 30 μg/mL and 150 μg/mL. In certain embodiments, the maximum plasma concentration of DMB is less than 150 μg/mL, less than 140 μg/mL, less than 130 μg/mL, less than 120 μg/mL, less than 110 μg/mL, less than 100 μg/mL, less than 90 μg/mL, less than 80 μg/mL, less than 70 μg/mL, less than 60 μg/mL, less than 50 μg/mL, less than 40 μg/mL, less than 30 μg/mL, or less than 20 μg/mL. In some embodiments, the plasma concentration of DMB is between 50 and 100 mg/mL, between 40 and 90 mg/mL, between 30 and 80 mg/mL, between 25 and 90 μg/mL, or between 20 and 100 μg/mL. In certain embodiments, the AUC is less than 2500 h*mg/mL, less than 2000 h*mg/mL, less than 1500 h*μg/mL, less than 1000 h*μg/mL, or less than 500 h*μg/mL.

In some embodiments, the percentage of fetal hemoglobin in the blood of a subject increases after one week of administering as compared to baseline. In other embodiments, the percentage of fetal hemoglobin in the blood of a subject increases after two weeks of administering as compared to baseline. In certain embodiments, the percentage of fetal hemoglobin in the blood of a subject increases after four weeks of administering as compared to baseline. In some embodiments, the percentage of fetal hemoglobin in the blood of a subject increases after one day of administering as compared to baseline. In certain embodiments, the percentage of fetal hemoglobin in the blood of a subject increases after 3 days of administering as compared to baseline.

In some embodiments, the methods for increasing the percentage of fetal hemoglobin further comprise administering to the subject hydroxyurea, decitabine, an HDAC inhibitor, or a combination thereof. In certain embodiments, the HDAC inhibitor is MS-275.

In some embodiments, the 2,2-dimethylbutyrate is administered as sodium 2,2-dimethylbutyrate. In certain embodiments, the administration of the DMB is by oral administration.

In certain embodiments, the amount of fetal globin in the blood of the subject increases. In some embodiments, the number of F-cells in the blood of the subject increases. In certain embodiments, the number of F-reticulocytes in the blood of the subject increases. In some embodiments, the amount of fetal hemoglobin in the blood of the subject increases. In certain embodiments, the amount of total hemoglobin in the blood of the subject increases. In some embodiments, the percentage of reticulocytes in the blood of the subject increases. In certain embodiments, the number of reticulocytes in the blood of the subject increases. In some embodiments, hematocrit increases. In certain embodiments, red blood cell production increases.

In some embodiments, the administration of DMB is by pulsed administration. In certain embodiments, the pulsed administration comprises administering DMB for about 8 weeks, followed by not administering DMB for about 4 weeks. In some embodiments, the pulsed administration comprises administering DMB for about 6 weeks, followed by not administering DMB for about 2 weeks. In certain embodiments, the pulsed administration comprises administering DMB for about 4 weeks, followed by not administering DMB for about 2 weeks. In some embodiments, the pulsed administration comprises administering DMB for about 2 weeks, followed by not administering DMB for about 2 weeks. In some embodiments, pulsed administration comprises pulses of administering DMB for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In certain embodiments, pulsed administration comprises intervals of not administering DMB of about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In some embodiments, administration is continuous. In certain embodiments, administration is for the lifetime of the subject.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
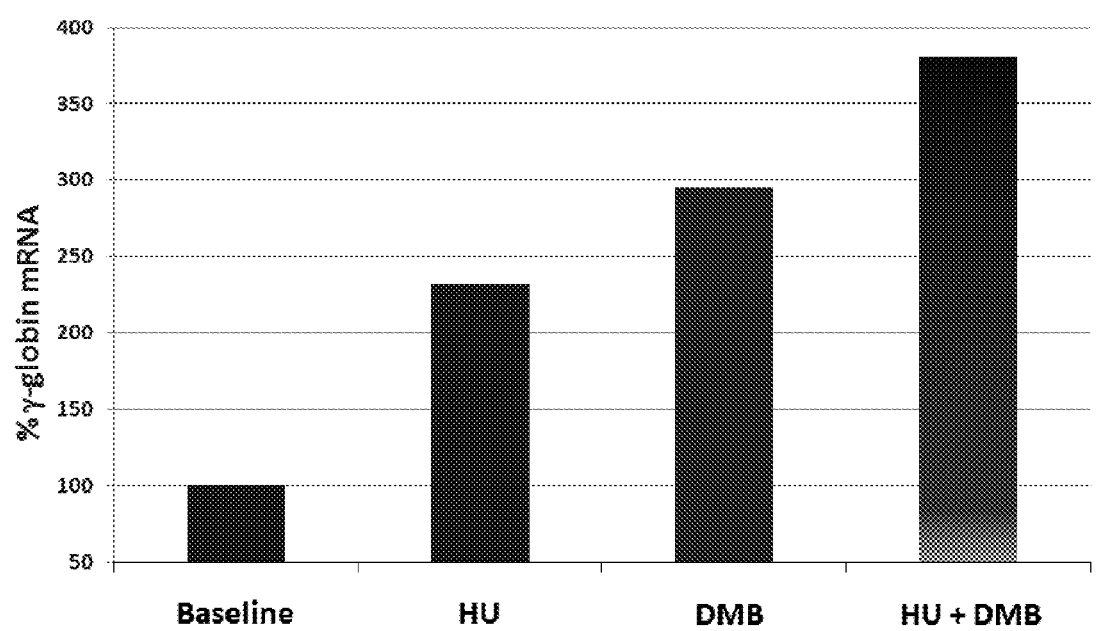
FIG. 1 is a graphic representation of fetal globin (γ-globin) mRNA in baboons treated with hydroxyurea (HU) and 2,2-dimethylbutyrate (DMB).

Normal adult hemoglobin (HbA) is made up of two alpha globin chains and two beta globin chains ($\alpha_2\beta_2$). Hemoglobinopathies, such as beta thalassemias and sickle cell disease (SCD), result from changes in the amino acid sequence or quantity and function of adult hemoglobin. Fetal globin (also known as gamma globin) normally combines with alpha globin chains prenatally to form fetal hemoglobin (HbF).

The sequential expression of the globin genes results in production of specific types of hemoglobins at different stages of development. At 12 weeks of gestation, a transition from embryonic to fetal hemoglobin ($\alpha_2\gamma_2$) occurs, and at 28 weeks of gestation, increasing amounts of beta-globin and of adult hemoglobin A (HbA, $\alpha_2\beta_2$) are produced. Alpha-like globin protein must equal beta-like globin proteins for intact hemoglobin tetramers to form.

Anemias

The major function of red blood cells is to transport oxygen to tissues of the body. Minor functions include the transportation of nutrients, intercellular messages, and cytokines, and the absorption of cellular metabolites. Anemia, or a loss of red blood cells or red blood cell capacity, can be grossly defined as a reduction in the ability of blood to transport oxygen. Anemia can be measured by determining a patient's red blood cell mass or hematocrit (Hct). Hematocrit values are indirect, but fairly accurate measures of the total hemoglobin concentration of a blood sample. Anemia, as measured by a reduced Hct, may be chronic or acute. Acute anemia may be caused by trauma or surgery. Gastrointestinal tract lesions or gynecologic disturbances cause generally rather chronic blood loss. Chronic anemia may be caused by extrinsic red blood cell abnormalities, intrinsic abnormalities or impaired production of red blood cells. Extrinsic or extra-corpuscular abnormalities include antibody-mediated disorders such as transfusion reactions and erythroblastosis, mechanical trauma to red cells such as micro-angiopathic hemolytic anemias, thrombotic thrombocytopenic purpura and disseminated intravascular coagulation. In addition, infections by parasites such as *Plasmodium*, chemical injuries from, for example, lead poisoning, radiation therapy, bone marrow/stem cell transplants, and sequestration in the mononuclear system such as by hypersplenism can result in red blood cell disorders and deficiencies.

Impaired red blood cell production can occur by disturbing the proliferation and differentiation of the stem cells or committed cells. Some of the more common diseases of red cell production include aplastic anemia, hypoplastic anemia, pure red cell aplasia, and anemia associated with renal failure or endocrine disorders. Disturbances of the proliferation and differentiation of erythroblasts include defects in DNA synthesis such as impaired utilization of vitamin B 12 or folic acid and the megaloblastic anemias, defects in heme or globin synthesis, and anemias of unknown origins such as sideroblastic anemia, anemia associated with chronic infections such as malaria, trypanosomiasis, HIV, hepatitis virus or other viruses, anemia associated with chronic inflammation (e.g. rheumatoid arthritis), and myelophthisic anemias caused by marrow deficiencies.

Intrinsic abnormalities include both hereditary and acquired disorders. Acquired disorders are those which have been induced through, for example, a membrane defect such as paroxysmal nocturnal hemoglobinuria. Hereditary disorders include disorders of membrane cytoskeleton such as spherocytosis and elliptocytosis, disorders of lipid synthesis such as an abnormally increased lecithin content of the cellular membrane, red cell enzyme deficiencies such as deficiencies of pyruvate kinase, hexokinase, glutathione synthetase and glucose-6-phosphate dehydrogenase. Although red blood cell disorders may be caused by certain drugs and immune system disorders, the majority are caused by genetic defects in the expression of hemoglobin. Disorders of hemoglobin synthesis include deficiencies of globin synthesis such as thalassemia syndromes and structural abnormalities of globin such as sickle cell syndromes and syndromes associated with unstable hemoglobins.

Beta Thalassemias

Thalassemia syndromes result from deficiencies in either alpha-globin ($\alpha$-thalassemia) or beta-like globin ($\beta$-thalassemia) chains. The diseases become apparent when the deficient globin is required during development. $\alpha$-Thalassemia is symptomatic during gestation, as $\alpha$-globin is required for fetal hemoglobin (HbF, $\alpha_2\gamma_2$). As $\beta$-globin is not required in large amounts before birth, $\beta$-thalassemia is asymptomatic until around 6 months after birth. Mutations that cause prolonged production of fetal $\gamma$-globin chains may present later, at 2 to 4 years of age.

The major pathologic process in thalassemia is the imbalance of alpha and non-alpha globin chain accumulation. The unaffected chains, produced in normal amounts, precipitate during erythropoiesis. In $\beta$-thalassemia, the precipitated $\alpha$-globin chains are particularly toxic, damaging cell membranes and causing rapid cell death (apoptosis). Red blood cell life-span is further shortened by removal of abnormal cells in the reticuloendothelial system. Erythropoietin levels increase, causing erythroid hyperplasia. Hypersplenism causes more severe anemia.

Beta globin is made by two genes, one on each chromosome 11. The beta thalassemia syndromes are caused by more than 175 molecular mutations affecting the beta globin gene complex. Each beta globin gene comprises three exons which encode about 146 amino acids, two introns, and a 5'-untranslated region containing the promoter sequences. Biosynthesis of beta globin begins with transcription of the entire gene followed with RNA processing of the message, removal of the introns by splicing, poly A addition, capping and post-transcriptional modifications. The mature mRNA molecule is exported from the nucleus and translated into beta globin. Defects in each of these functions have been found associated with specific thalassemias. Identified mutations include single-nucleotide deletions, insertions and substitutions, frame shift mutations, deletions of entire segments of coding or controlling regions, improper termination signals, aberrant splicing signals, and multiple mutations.

$\beta^0$-Thalassemias are characterized by a complete absence of any beta globin chains. $\beta^+$-Thalassemias are characterized by detectable presence of a reduced amount of beta chains. There are three principal categories of beta thalassemias: thalassemia major, thalassemia intermedia, and thalassemia minor.

Thalassemia syndromes are graded according to severity of the anemia. Thalassemia major, in which severe anemia manifests during infancy, is caused by inheritance of two severely impaired beta-globin alleles. Such homozygous or doubly heterozygous conditions have milder manifestations when there is an increase in fetal globin chain production, or when the co-inheritance of alpha thalassemia decreases the net imbalance of alpha-globin to beta-globin. Thalassemia trait (inheritance of a single defective allele) is characterized by mild hypochromic, microcytic anemia and does not require treatment. Thalassemia intermedia (TI) causes moderate anemia with total hemoglobin levels of 6.0 to 10.0 grams per dL. These patients require occasional transfusions with infections, but do not require regular transfusions during childhood, although many deteriorate later in life, and develop similar complications as in thalassemia major.

The beta thalassemia trait can also combine with variant hemoglobins to produce other related blood disorders. Hemoglobin E trait is one of the most common abnormal hemoglobins. In some instances, a person carries the beta thalassemia trait and the hemoglobin E trait, which leads to HbE beta thalassemia, a moderately severe anemia that has similar symptoms to beta thalassemia intermedia but on occasion may be as severe as thalassemia major. It is usually found in people of Southeast Asian ancestry, such as Cambodians, Vietnamese, and Thai.

In certain instances, a person carries the beta thalassemia trait and the hemoglobin S trait (the abnormal hemoglobin found in people with sickle cell disease), which leads to HbS beta thalassemia. The severity of this condition varies according to the amount of normal beta globin produced by the beta globin gene. When no beta globin is produced by the beta globin gene, the condition is almost identical to sickle cell disease. When some beta globin is produced by the beta globin gene, the condition is less severe. Hemoglobin S trait is commonly found in people of African or Mediterranean ancestry, such as Africans, Italians, Greeks, Turks, and in people from the Caribbean.

In β-thalassemia major, red blood cell (RBC) transfusion is the mainstay of supportive therapy. Transfusions should maintain a hemoglobin level ideally above 10.5 to 11 g/dL (range 10.5 to 13 g/dL). Transfusions can transmit infections, including hepatitis viruses, HIV, CMV, and other pathogens. Further complications from transfusion therapy arise when iron deposition causes dysfunction in the heart, liver, and endocrine organs. Glucose intolerance with insulin-dependent diabetes mellitus, primary hypothyroidism, hypoparathyroidism, delayed puberty, amenorrhea, and osteopenia, are common; arrhythmias are often precipitated by cardiac hemosiderosis and hypocalcemia secondary to hypoparathyroidism. Growth retardation may respond to Growth Hormone before 13 years of age. Hepatic iron and hepatitis C lead to fibrosis and cirrhosis. Cardiac dysfunction is detectable early by cardiovascular magnetic resonance and T2*measurements <20 ms and reduced ejection fractions, and presents with fatigue, arrhythmias, or pericarditis, advancing to congestive heart failure, the major cause of death in transfused patients (60%), followed by infections (13%), and liver disease, including hepatocellular carcinoma (6%). Pulmonary hypertension develops in untransfused intermedia patients with hemolysis; a TR jet velocity >2 is associated with 25% mortality.

Osteopenia occurs in approximately 55% of thalassemia major and intermedia patients. In certain instances, it is severe and causes fractures, and even occurs in transfused patients in early childhood. In some instances, affected patients are maintained on elemental calcium (1500 mg per day) and vitamin D (400 IU per day). In certain instances, osteoporosis is treated with bisphosphonates.

Patients should be monitored for marrow expansion, facial deformity, splenomegaly, growth retardation, endocrinopathies, and osteopenia. Pulmonary hypertension is a recently recognized risk, related to chronic hemolysis in untransfused patients. Tricuspid regurgitation (TR jet of >2) is associated with a 25% mortality, for which transfusions should be instituted. Patients with β$^+$ thalassemia and baseline erythropoietin levels <130 mU/mL, require erythropoietin and a fetal globin stimulant.

The hyperplastic marrow in thalassemia intermedia stimulates intestinal iron absorption and eventually iron overload and endocrine deficiencies occur as in thalassemia major, although more slowly, and cardiomyopathy does not develop in untransfused patients. Avoidance of iron-rich meats and regular consumption of tea can reduce iron absorption. Osteopenia occurs in 55% of major and intermedia patients. Hypercoagulability and thromboembolic events occur particularly in splenectomized patients, related to thrombocytosis and hepatic dysfunction. Folic acid and antioxidant supplements should be used. Spinal cord compression syndromes from thoracic or vertebral paraspinal bone marrow masses should be suspected with acute or increasing weakness, numbness, and diminished reflexes in the lower extremities, a medical emergency.

In some instances, tests to determine the genotypes of beta thalassemia in a patient include, but are not limited to, hemoglobin electrophoresis, globin chain electrophoresis, molecular mutation analysis, family studies, and quantitative trait loci (QTL) analysis.

In certain instances, disruption of the beta globin gene complex results in decreased synthetic ratios of non-alpha to alpha globin chains, precipitation of excess unbalanced alpha globin chains, and programmed cell death of erythroblasts early in their development. Affected patients do not become anemic until the fetal (gamma) globin genes are developmentally silenced. Patients with persistent high levels of fetal globin typically have less severe anemia, milder clinical syndromes, and are often transfusion-independent. The beta thalassemias are thus one of a few clinical conditions in which a gene that is transiently expressed during fetal life can functionally replace a mutant gene normally expressed later in development. Reactivation of fetal (gamma) globin expression is appealing as a therapeutic approach to the beta thalassemias, because the fetal globin genes are universally present and appropriately contextually integrated in the beta globin locus in hematopoietic stem cells in virtually all humans.

Sickle Cell Disease

In sickle cell disease (SCD), one amino acid substitution in the beta globin chain results in the generation of hemoglobin S (HbS). Upon deoxygenation, HbS molecules undergo aggregation and polymerization ultimately leading to a morphological distortion of the red cells, which acquire a sickle or holly-leaf shape. Sickling has two major consequences, a chronic hemolytic anemia and an occlusion of small blood vessels that results in ischemic damage to tissues. Further, when exposed to low oxygen tensions, polymerization converts blood-containing HbS from a free flowing liquid to a viscous gel. Consequently, in certain instances, the degree of pathology associated with sickle cell disease is correlated with the relative amount of HbS in the patient's system. HbS polymerization is also significantly affected by the hemoglobin concentration in the cell. The higher the HbS concentration, the greater is the chance for contact between two or more HbS molecules. In some instances, dehydration increases hemoglobin concentration and greatly facilitates sickling.

To some extent, sickling is a reversible phenomenon. With increased oxygen tensions, sickled cells depolymerize. This process of polymerization-depolymerization is very damaging to red cell membranes and eventually leads to irreversibly sickled cells (ISC), which retain their abnormal shape even when fully oxygenated. The average ISC survives for about 20 days in the body, as compared to the normal 120 day life span.

Individuals with HbS syndromes have frequent infections, chronic hemolysis with a striking reticulocytosis and hyperbilirubinemia. The course of the disease is typically punctuated with a variety of painful crises called vaso-occlusive crises. These crises represent episodes of hypoxic injury and infarction in the organs, abdomen, chest, extremities, or joints. Leg ulcers are an additional manifestation of vaso-occlusive tendency of this disease. Central nervous system involvement is common producing seizures and even strokes. Aplastic crises, also common, represent a temporary cessation of bone marrow activity and, in certain instances, are triggered by infections, folic acid deficiency, or both. Crises are episodic and reversible, but may be fatal. Damage from crisis episodes tends to be cumulative and even in those individuals with milder forms of sickle cell disease life spans can be greatly reduced. Absent alternative intervention, patients typically die before the age of 30.

Individuals with severe SCD develop no symptoms until about five to six months after birth. In these infants, fetal hemoglobin (HbF) does not interact with HbS and can modulate the effects of HbS, as long as sufficient quantities of HbF are present. HbF levels above 20% are generally considered to be sufficient to eliminate symptoms associated with sickle cell disease.

Blood Disorders

Sickle cell disease and thalassemias can be characterized as "blood disorders" and are caused by abnormalities in the globin genes. Blood disorders include disorders that can be treated, prevented, or otherwise ameliorated by the administration of a compound or composition of the invention. A blood disorder is any disorder of the blood and blood-forming organs. The term blood disorder includes nutritional anemias (e.g., iron deficiency anemia, sideropenic dysphasia, Plummer-Vinson syndrome, vitamin B12 deficiency anemia, vitamin B12 deficiency anemia due to intrinsic factor, pernicious anemia, folate deficiency anemia, and other nutritional anemias), myelodysplastic syndrome, bone marrow failure or anemia resulting from chemotherapy, radiation or other agents or therapies, hemolytic anemias (e.g., anemia due to enzyme disorders, anemia due to phosphate dehydrogenase (G6PD) deficiency, favism, anemia due to disorders of glutathione metabolism, anemia due to disorders of glycolytic enzymes, anemias due to disorders of nucleotide metabolism and anemias due to unspecified enzyme disorder), thalassemia, α-thalassemia, β-thalassemia (for example, hemoglobin E beta thalassemia), δβ-thalassemia, thalassemia trait, hereditary persistence of fetal hemoglobin (HPFP), and other thalassemias, sickle cell disorders (sickle cell anemia with crisis, sickle cell anemia without crisis, double heterozygous sickling disorders, sickle cell trait and other sickle cell disorders), hereditary hemolytic anemias (hereditary spherocytosis, hereditary elliptocytosis, other hemaglobinopathies and other specified hereditary hemolytic anemias, such as stomatocyclosis), acquired hemolytic anemia (e.g., drug-induced autoimmune hemolytic anemia, other autoimmune hemolytic anemias, such as warm autoimmune hemolytic anemia, drug-induced non-autoimmune hemolytic anemia, hemolytic-uremic syndrome, and other non-autoimmune hemolytic anemias, such as microangiopathic hemolytic anemia); aplastic anemias (e.g., acquired pure red cell aplasia (erythoblastopenia), other aplastic anemias, such as constitutional aplastic anemia and fanconi anemia, acute posthemorrhagic anemic, and anemias in chronic diseases), coagulation defects (e.g., disseminated intravascular coagulation (difibrination syndrome)), hereditary factor VIII deficiency (hemophilia A), hereditary factor IX deficiency (Christmas disease), and other coagulation defects such as Von Willebrand's disease, hereditary factor Xi deficiency (hemophilia C), purpura (e.g., qualitative platelet defects and Glanzmann's disease), neutropenia, agranulocytosis, functional disorders of polymorphonuclear neutrophils, other disorders of white blood cells (e.g., eosinophilia, leukocytosis, lymophocytosis, lymphopenia, monocytosis, and plasmacyclosis), diseases of the spleen, methemoglobinemia, other diseases of blood and blood forming organs (e.g., familial erythrocytosis, secondary polycythemia, essential thrombocytosis and basophilia), thrombocytopenia, infectious anemia, hypoproliferative or hypoplastic anemias, hemoglobin C, D and E disease, hemoglobin lepore disease, and HbH and HbS diseases, anemias due to blood loss, radiation therapy or chemotherapy, or thrombocytopenias and neutropenias due to radiation therapy or chemotherapy, sideroblastic anemias, myelophthisic anemias, antibody-mediated anemias, and certain diseases involving lymphoreticular tissue and reticulohistiocytic system (e.g., Langerhans' cell hystiocytosis, eosinophilic granuloma, Hand-Schuller-Christian disease, hemophagocytic lymphohistiocytosis, and infection-associated hemophagocytic syndrome).

Treatment Options

The average U.S. survival of patients with beta thalassemia and SCD is approximately 26 years and 40 years of age, respectively.

In beta thalassemia intermedia (TI) and SCD, most affected individuals can sustain activities of daily living when provided with appropriate supportive care, such as transfusions at times of illness (e.g. infection) or pregnancy. Transfusions are required more frequently over time, as the conditions progress to more severe, later stage disease. Many patients develop iron overload as a complication of multiple transfusions and other transfusion-related complications such as those described above. Frequent transfusions in areas of the world with suboptimal blood product screening also place such patients at risk for potential blood-borne pathogens. Cirrhosis from hepatitis C is common in patients in many parts of the world. With transfusion therapy, many patients become alloimmunized, which increases the risk of hypersensitivity reactions and transfusion requirements due to progressively reduced RBC survival.

The Role of Fetal Hemoglobin

Genotypic variations in healthy individuals have been identified wherein adult beta globin is not formed, but severe complications are avoided. In certain instances, these patients express fetal globin in amounts sufficient to substitute for the missing beta globin chains. In some instances, this hereditary persistence of fetal hemoglobin involves one or both of the fetal globin genes. In certain instances, consistent production of fetal globin accomplishes the necessary functions of abnormal or missing beta globin chains.

The level of fetal hemoglobin (HbF) expression is one of the most important modifiers of disease expression for patients with SCD. The percentage of HbF (% HbF) influences both laboratory values and clinical features of children and adults with SCD. In one instance, 30% HbF in every red blood cell is a highly effective inhibitor of clinical sickling, while 15% to 22% HbF in 60% to 70% of cells is beneficial to Saudi Arabian and Indian patients. In further instances, elevated % HbF has been significantly associated with fewer painful vaso-occlusive events, fewer episodes of acute chest syndrome, and reduced early mortality. Increased HbF levels correlate with reduction in organ damage and improved patient survival.

Higher production of HbF parallels higher hemoglobin levels in beta thalassemia patients, similar to findings in sickle cell disease. In certain instances, patients with beta thalassemia treated with hydroxyurea had an increase in HbF levels and an apparent decrease in crisis frequencies. For instance, the two major hemoglobin components in patients with HbE beta thalassemia disease are HbE and HbF, the levels of HbF varying from 30% to 70%. In some instances, there is a good correlation of hemoglobin levels with the amount of HbF production in certain groups of patients with HbE beta thalassemia disease. Increased HbF production associated with an improvement in the alpha/non-alpha globin production can be achieved using hydroxyurea. In some instances, the temporal relationship between the increase in % HbF (and the reciprocal decrease in % HbE) and the increase in total hemoglobin is consistent with improved erythropoiesis. For example, in a study almost all HbE beta thalassemia patients treated with hydroxyurea responded with an increase in HbF levels and a reciprocal decline in % HbE, reticulocytosis was decreased, and there was a slight but statistically significant increase in hemoglobin levels and an improved balance in alpha/non-alpha globin chain ratios.

In certain instances, reactivating fetal globin to approximately 60-70% of α-globin chain synthesis ameliorates anemia in beta thalassemia enough to eliminate transfusion requirements. Chemotherapeutic agents (hydroxyurea and 5-azacytidine or decitabine), short chain fatty acid derivatives (SCFADs), and rhu-erythropoietin (EPO) are being evaluated in clinical trials, with highest hematologic responses observed in patients with baseline (untransfused) HbF levels >50% and erythropoietin levels >130 mU/mL. In some instances, combinations of these agents are required to eliminate regular transfusion requirements in severe β-thalassemia patients. Non-mutagenic, non-cytotoxic agents are preferable over chemotherapy for life-long treatment. Sodium phenylbutyrate (Buphenyl) and arginine butyrate have increased total hemoglobin by 1-4 g/dL above baseline in untransfused patients, but require large numbers of tablets or IV infusion, respectively. Patients with $\beta^+$ thalassemia and baseline EPO levels <80 mU/ml have responded best to combined therapy with butyrate and EPO. The long-acting EPO preparation, darbepoietin, increases hemoglobin in some. These therapies require supplementation with oral iron to be effective, even in the presence of elevated ferritin levels, as stored iron may not be available for erythropoiesis, and several months of treatment are often required. New oral short chain fatty acid derivatives under evaluation appear more tolerable Hydroxyurea A variety of small molecules have been shown to affect fetal hemoglobin or fetal globin expression. For example, hydroxyurea (HU) was found to stimulate globin expression (Letvin, N. L., et al. 1984 *N. Engl. J. Med.* 310:869-73). Stimulation, however, did not appear to be very specific to fetal globin (Charache, S., et al. 1987 *Blood* 69:109-16).

Hydroxyurea, the first and only FDA-approved drug used to treat the underlying pathology of SCD, acts by increasing fetal globin levels. However, hydroxyurea is only used in a small proportion of patients for several reasons. It does not increase fetal globin in many SCD patients, and clinical benefit is observed in only 40-50% of patients. Furthermore, hydroxyurea is a mutagenic cancer chemotherapy associated with potential carcinogenicity and teratogenicity.

Treatment of patients with hydroxyurea may be complicated by severe, sometimes life-threatening, adverse effects. Hydroxyurea is mutagenic and clastogenic, and causes cellular transformation to a tumorigenic phenotype. Hydroxyurea is thus unequivocally genotoxic and a presumed trans-species carcinogen, which implies a carcinogenic risk to humans. In patients receiving long-term hydroxyurea for myeloproliferative disorders, such as polycythemia vera and thrombocythemia, secondary leukemias have been reported.

Hydroxyurea is not only a cytotoxic and myelosuppressive agent. In addition, hydroxyurea has a narrow therapeutic index and effective treatment with hydroxyurea requires a careful dose escalation up to the maximum tolerated dose (MTD) or a stated maximum dose. The initial dose of hydroxyurea is 15 mg/kg/day as a single dose. The patient's blood count must be monitored very two weeks. If blood counts are in an acceptable range, the dose may be increased by 5 mg/kg/day every 12 weeks until a maximum tolerated dose (the highest dose that does not produce toxic blood counts over 24 consecutive weeks), or 35 mg/kg/day, is reached. If blood counts are between the acceptable range and toxic range, the dose is not increased. If blood counts are considered toxic, hydroxyurea should be discontinued until hematologic recovery. Treatment may then be resumed after reducing the dose by 2.5 mg/kg/day from the dose associated with hematologic toxicity. Hydroxyurea may then be titrated up or down, every 12 weeks in 2.5 mg/kg/day increments, until the patient is at a stable dose that does not result in hematologic toxicity for 24 weeks. Any dosage on which a patient develops hematologic toxicity twice should not be tried again.

In addition to hydroxyurea, other cancer agents such as 5-azacytidine and 5-aza-2'-deoxycytidine have also demonstrated efficacy in small SCD clinical trials, but the toxicity and mutagenicity of these drugs have limited their clinical development and broad application. For beta thalassemia, bone marrow (or stem cell) transplantation is the only effective therapy, but is feasible in only a small number of patients with well-matched donors and significant financial resources or health insurance.

Exogenous administration of erythropoiesis stimulating agents (ESAs) such as erythropoietin (EPO) and darbepoietin has been shown to increase RBC counts and total Hgb levels in beta thalassemia patients, but does not correct the globin chain imbalance.

2,2-Dimethylbutvrate (DMB)

2,2-Dimethylbutyrate (DMB), is a novel compound within a class of agents known as short-chain fatty acids (SCFAs) and short chain fatty acid derivatives (SCFADs). DMB is one of several SCFAs that augment expression of the fetal globin gene promoter and thereby increases fetal globin synthesis. 2,2-Dimethylbutyrate (DMB) refers to the free acid, a pharmaceutically acceptable salt, or ester of 2,2-dimethylbutyric acid (e.g., sodium 2,2-dimethylbutyrate).

Arginine butyrate (AB) was a prior generation SCFA used successfully in small studies with beta thalassemia patients to stimulate fetal globin expression and increased total hemoglobin (Hgb) levels. Several patients enrolled in AB studies became transfusion-independent with prolonged home therapy for up to 7 years. Another SCFA, sodium phenylbutyrate (SPB), increased total hemoglobin levels by 2 g/dL above baseline in 50% of untransfused beta thalassemia patients. However, both AB and SPB are histone deacetylase (HDAC) inhibitors that inhibit cell growth and suppress erythropoiesis, which is counterproductive to correcting the patient's anemia.

In open-label pilot clinical studies conducted in beta thalassemia, SCFAs that were evaluated prior to DMB, such as phenylbutyrate and arginine butyrate (AB), increased fetal globin synthesis and total hemoglobin levels sufficiently to enable some previously transfusion-dependent patients to become transfusion-independent. However, these early SCFA therapeutics were rapidly metabolized and required large doses and/or prolonged intravenous (IV) infusions for benefit. In addition, continuous therapy with these compounds suppressed erythropoiesis, an effect that reduced the net benefit from fetal globin expression and could be ameliorated when medication was administered intermittently. Both sodium phenylbutyrate (SPB) and AB have increased HbF and total hemoglobin (Hgb) levels in patients with SCD. The target product profile of a therapeutic agent for patients with beta thalassemia or SCD is an orally administered medication that stimulates both fetal-globin gene expression and augments erythropoiesis.

DMB is a third generation SCFA that is orally bio-available and has a longer half-life than AB or SPB. In addition, DMB does not appear to suppress erythropoiesis at concentrations associated with biologic activity, but instead stimulates cell proliferation and inhibits apoptosis of cultured erythroid progenitors from thalassemic patients. In additional instances, DMB stimulates erythroid cell proliferation and survival, and increases total hemoglobin levels in phlebotomized anemic baboons. DMB is not an HDAC inhibitor, but, in certain instances, stimulates erythropoiesis through prolonging phosphorylation of the transcription factor, STAT-5, while still inducing expression of the fetal globin gene promoter. DMB is an oral, promoter-targeted fetal globin gene stimulant, which also prolongs erythroid survival and proliferation, and it has demonstrated favorable pharmacokinetic (PK) and safety profiles in normal volunteers in Phase 1 clinical trials.

DMB induces fetal globin expression in laboratory studies of reporter gene assays, erythroid cell lines, and in erythroid progenitors cultured from thalassemia patients. In vivo studies carried out in transgenic mice and anemic baboons also demonstrate increased fetal globin levels and increased RBC production as assayed by reticulocytes, total hemoglobin (Hgb), and hematocrit (Hct).

In some embodiments, as a therapeutic for SCD and beta thalassemia, DMB induces fetal globin synthesis to replace the mutant or missing beta globin chains, respectively. In beta thalassemia, the fetal globin chains can combine with the alpha chains to reduce the high concentrations of unmatched alpha globin chains. In SCD, fetal globin inhibits polymerization of HbS, which reduces RBC sickling, thereby reducing ischemic events and hemolytic anemia.

Preclinical and Clinical Studies with DMB

Twenty-six weeks of daily administration of high doses of DMB to Sprague Dawley rats, performed using daily oral doses up to 500 mg/kg/day [human equivalent dose (HED)=81 mg/kg/day] showed that DMB was well-tolerated, with only reversible increases in liver function tests in a few females. A 26-week study in Beagle dogs, performed using daily oral doses of DMB of up to 300 mg/kg/day (HED=167 mg/kg), resulted in only slight lags in weight gain compared to control animals that were not associated with changes in feeding or activity, and DMB was otherwise well-tolerated. These doses in dogs and rats achieve cumulative drug concentrations that are 1.2 and 2.9 times the 20 mg/kg dose in human subjects, after allometric scaling (Table 7 and Table 8).

In laboratory studies, DMB has been shown to stimulate erythroid cell proliferation through the STAT-5 signaling pathway, the same pathway activated by erythropoietin stimulating agents. In addition, DMB reduces premature death of thalassemic erythroid progenitors by prolonging expression of Bcl-xL, an anti-apoptotic protein complex.

To date, DMB has been evaluated in 55 healthy human subjects in 2 clinical trials. In a single dose phase 1 study, subjects were treated with single doses of DMB at dose levels ranging from 2 to 20 mg/kg. This study was completed with no clinically significant adverse events (AEs) noted and revealed that biologically active plasma drug levels (as established in prior in vitro studies performed with whole blood from patients with thalassemia intermedia (TI)) could be achieved with doses at or above 10 mg/kg.

In a multiple-dose phase 1 clinical study in 41 healthy human subjects, repeat daily doses of DMB (5 to 15 mg/kg/day) for 14 consecutive days was well-tolerated and no clinically significant AEs or laboratory abnormalities were observed.

In addition, DMB has been evaluated in 21 patients with thalassemia intermedia at repeat doses of 10 mg/kg, 20 mg/kg, 30 mg/kg, and 40 mg/kg over 8 weeks, and 25 patients with sickle cell disease at repeat doses of 10 mg/kg, 20 mg/kg, and 30 mg/kg over 6 weeks.

Pulsed Administration

In some embodiments, pulsed administration is more effective than continuous treatment because total pulsed doses are often lower than would be expected from continuous administration of the same composition. Each pulse dose can be reduced and the total amount of drug administered over the course of treatment is minimized.

In traditional forms of therapy, repeated administration is designed to maintain a desired level of an active ingredient in the body. Very often, complications that develop can be attributed to dosage levels that, to be effective, are near toxic or otherwise harmful to normal cells. In contrast, with pulse therapy, in vivo levels of drug drop below that level required for effective continuous treatment. Therefore, pulsing is not simply the administration of a sufficiently large bolus such that there will be therapeutically sufficient drug available for a long period of time. Pulsed administration can substantially reduce the amount of the composition administered to the patient per dose or per total treatment regimen with an increased effectiveness. This represents a significant saving in time, effort, and expense and, more importantly, a lower effective dose substantially lessens the number and severity of complications that may be experienced by the patients.

Individual pulses can be delivered to the patient continuously over a period of several hours, such as about 2, 4, 6, 8, 10, 12, 14 or 16 hours, or several days, such as 2, 3, 4, 5, 6, or 7 days, preferably from about 1 hour to about 24 hours and more preferably from about 3 hours to about 9 hours. Alternatively, periodic doses can be administered in a single bolus or a small number of injections of the composition over a short period of time, typically less than 1 or 2 hours. For example, arginine butyrate has been administered over a period of 4 days with infusions for about 8 hours per day or overnight, followed by a period of 7 days of no treatment. This has been shown to be an effective regimen for many thalassemic disorders. Fetal hemoglobin levels rise substantially and there is a significant rise in the number of both adult and fetal hemoglobin expressing cells. In certain instances, a substantial rise in HbF means that there are positive consequences that raise the patient's standard of living such as, for example, increased activity or mobility, fewer side effects, fewer hospital stays or visits to the physician, or fewer transfusions. For instance, HbF levels above 20% are generally considered sufficient to eliminate symptoms associated with sickle cell disease.

The interval between pulses or the interval of no delivery is greater than 24 hours and preferably greater than 48 hours, and can be for even longer such as for 3, 4, 5, 6, 7, 8, 9 or 10 days, two, three or four weeks or even longer. Often, the interval between pulses can be calculated by administering another dose of the composition when the composition or the active component of the composition is no longer detectable in the patient prior to delivery of the next pulse. Intervals can also be calculated from the in vivo half-life of the composition. Intervals may be calculated as greater than the in vivo half-life, or 2, 3, 4, 5 and even 10 times greater the composition half-life. For compositions with fairly rapid half lives, intervals may be 25, 50, 100, 150, 200, 250 300 and even 500 times the half life of the chemical composition. The number of pulses in a single therapeutic regimen may be as little as two, but is typically from about 5 to 10, 10 to 20, 15 to 30 or more. In some embodiments, patients receive drugs for life according to the methods of this invention without the problems and inconveniences associated with current therapies.

In certain embodiments, compositions are administered by most any means, but are preferable delivered to the patient as an injection (e.g. intravenous, subcutaneous, intraarterial), infusion or instillation, and more preferably by oral ingestion.

Method for Increasing % HbF and/or Total Hemoglobin

Provided herein are methods for increasing the percentage of fetal hemoglobin in the blood of a subject, comprising administering to said subject: a) 2,2-dimethylbutyrate (DMB) as the free acid, a pharmaceutically acceptable salt, or ester thereof, and b) one or more agents selected from the group consisting of hydroxyurea, decitabine, and an HDAC inhibitor, wherein after the administration the percentage of fetal hemoglobin in the blood of the subject increases. In some embodiments, the percentage of fetal hemoglobin in the blood of a subject increases after one week of administering as compared to baseline. In other embodiments, the percentage of fetal hemoglobin in the blood of a subject increases after two weeks of administering as compared to baseline. In certain embodiments, the percentage of fetal hemoglobin in the blood of a subject increases after four weeks of administering as compared to baseline. In some embodiments, the percentage of fetal hemoglobin in the blood of a subject increases after one day of administering as compared to baseline. In certain embodiments, the percentage of fetal hemoglobin in the blood of a subject increases after 3 days of administering as compared to baseline.

In some embodiments of the methods for increasing the percentage of fetal hemoglobin, the subject has been diagnosed with a blood disorder or anemia. In certain embodiments, the blood disorder is a sickle cell syndrome. In some embodiments, the blood disorder is a beta thalassemia syndrome.

In some embodiments, 2,2-dimethylbutyrate is administered as sodium 2,2-dimethylbutyrate. 2,2-Dimethylbutyrate includes, but is not limited to, 2,2-dimethylbutyric acid, sodium 2,2-dimethylbutyrate, potassium 2,2-dimethylbutyrate, magnesium 2,2-dimethylbutyrate, calcium 2,2-dimethylbutyrate, arginine 2,2-dimethylbutyrate, lysine 2,2-dimethylbutyrate, choline 2,2-dimethylbutyrate, methyl 2,2-dimethylbutyrate (2,2-dimethylbutyric acid methyl ester), ethyl 2,2-dimethylbutyrate, propyl 2,2-dimethylbutyrate, isopropyl 2,2-dimethylbutyrate, or tert-butyl 2,2-dimethylbutyrate.

In certain embodiments, the DMB is administered orally. In some embodiments, the HDAC inhibitor is MS-275. In certain embodiments, the administration of the one or more agents is orally. In some embodiments, the administration of the DMB and the one or more agents is orally. In certain embodiments, the DMB and the one or more agents are administered in a combined oral dosage form.

In some embodiments, the total daily dose of DMB does not exceed 100 mg/kg, does not exceed 90 mg/kg, does not exceed 80 mg/kg, does not exceed 70 mg/kg, does not exceed 60 mg/kg, does not exceed 50 mg/kg, does not exceed 40 mg/kg, does not exceed 35 mg/kg, does not exceed 30 mg/kg, does not exceed 25 mg/kg, does not exceed 20 mg/kg, does not exceed 15 mg/kg, does not exceed 10 mg/kg, or does not exceed 5 mg/kg. In certain embodiments, the total daily dose of DMB is between 10 and 60 mg/kg, between 20 and 70 mg/kg, between 30 and 80 mg/kg, between 40 and 90 mg/kg, or between 50 and 100 mg/kg. In some embodiments, the total daily dose of DMB is less than about 100 mg/kg, less than about 90 mg/kg, less than about 80 mg/kg, less than about 70 mg/kg, less than about 60 mg/kg, less than about 50 mg/kg, less than about 40 mg/kg, less than about 35 mg/kg, less than about 30 mg/kg, less than about 25 mg/kg, less than about 20 mg/kg, less than about 15 mg/kg, or less than about 10 mg/kg.

In certain embodiments, the dose of hydroxyurea does not exceed 35 mg/kg/day. In some embodiments, the dose of hydroxyurea is less than 35 mg/kg/day, less than 30 mg/kg/day, less than 25 mg/kg/day, less than 20 mg/kg/day, less than 15 mg/kg/day, less than 10 mg/kg/day, or less than 5 mg/kg/day. In certain embodiments, the dose of hydroxyurea is less than 90% of the maximum tolerated dose. In other embodiments, the dose of hydroxyurea is less than 80%, less than 70%, less than 60%, less than 50%, less than 40%, less than 30%, less than 20%, less than 10% of the maximum tolerated dose.

In some embodiments, the dose of decitabine does not exceed 15 mg/m$^2$. In certain embodiments, the dose of decitabine is less than about 15 mg/m$^2$, less than about 10 mg/m$^2$, less than about 5 mg/m$^2$, less than about 3 mg/m$^2$, less than about 2 mg/m$^2$, or less than about 1 mg/m$^2$. In other embodiments, decitabine is administered orally at a dose of not more than about 240 mg, not more than about 180 mg, not more than about 120 mg, not more than about 60 mg, or not more than about 30 mg.

In certain embodiments, the dose of MS-275 does not exceed 6 mg/m$^2$ administered weekly. In some embodiments, the dose of MS-275 is less than about 6 mg/m$^2$, less than about 5 mg/m$^2$, less than about 4 mg/m$^2$, less than about 3 mg/m$^2$, less than about 2 mg/m$^2$, or less than about 1 mg/m$^2$ administered weekly. In certain embodiments, MS-275 is administered daily.

In some embodiments, the total daily dose of DMB is more than 90 mg/kg, is more than 80 mg/kg, more than 70 mg/kg, more than 60 mg/kg, more than 50 mg/kg, more than 40 mg/kg, more than 30 mg/kg, more than 20 mg/kg, or more than 10 mg/kg.

In certain embodiments, the plasma concentration of DMB does not exceed a concentration of 90 μg/mL of DMB. In other embodiments, the plasma concentration does not exceed a concentration of 120 μg/mL of DMB. In certain embodiments, the plasma concentration of DMB does not exceed a concentration of 150 μg/mL. In some embodiments, the plasma concentration of DMB does not exceed a concentration of 200 μg/mL. In certain embodiments, the plasma concentration of DMB does not exceed a concentration of 250 μg/mL. In some embodiments, the plasma concentration of DMB is between 20 μg/mL and 90 μg/mL, or between 25 μg/mL and 120 μg/mL, between 30 μg/mL and 150 μg/mL, or between 30 μg/mL and 250 μg/mL. In certain embodiments, the maximum plasma concentration of DMB is less than 400 μg/mL, less than 350 μg/mL, less than 300 μg/mL, less than 250 μg/mL, less than 200 μg/mL, less than 150 μg/mL, less than 140 μg/mL, less than 130 μg/mL, less than 120 μg/mL, less than 110 μg/mL, less than 100 μg/mL, less than 90 μg/mL, less than 80 μg/mL, less than 70 μg/mL, less than 60 μg/mL, less than 50 μg/mL, less than 40 μg/mL, less than 30 μg/mL, or less than 20 μg/mL.

In some embodiments, the amount of fetal globin in the blood of the subject increases. In some embodiments, the number of F-cells in the blood of the subject increases. In certain embodiments, the number of F-reticulocytes in the blood of the subject increases. In some embodiments, the amount of fetal hemoglobin in the blood of the subject increases. In certain embodiments, the amount of total hemoglobin in the blood of the subject increases. In some embodiments, the percentage of reticulocytes in the blood of the subject increases. In certain embodiments, the number of reticulocytes in the blood of the subject increases. In some embodiments, hematocrit increases. In certain embodiments, red blood cell production increases.

In certain embodiments, the DMB is administered daily. In further embodiments, administration is continuous. In some embodiments, the administration of DMB is by pulsed administration. In certain embodiments, pulsed administration comprises administering DMB pulses for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 12 months. In some embodiments, pulsed administration comprises intervals of not administering DMB of about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In certain embodiments, administration is for the lifetime of the subject.

In some embodiments, the administration of DMB is by pulsed administration. In certain embodiments, the pulsed administration comprises administering DMB for about 8 weeks, followed by not administering DMB for about 4 weeks. In some embodiments, the pulsed administration comprises administering DMB for about 6 weeks, followed by not administering DMB for about 2 weeks. In certain embodiments, the pulsed administration comprises administering DMB for about 4 weeks, followed by not administering DMB for about 2 weeks. In some embodiments, the pulsed administration comprises administering DMB for about 2 weeks, followed by not administering DMB for about 2 weeks. In some embodiments, pulsed administration comprises pulses of administering DMB for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In certain embodiments, pulsed administration comprises intervals of not administering DMB of about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In some embodiments, administration is continuous. In certain embodiments, administration is for the lifetime of the subject.

In some embodiments, the subject is a mammal. In certain embodiments, the mammal is an animal. In some embodiments, the animal is a horse. In certain embodiments, the mammal is a human. In some embodiments, the human is a child. In certain embodiments, the human is under the age of 18. In some embodiments, the human is under the age of 10. In some embodiments, the human is under the age of 2.

Further provided herein are methods for increasing the percentage of fetal hemoglobin in the blood of a subject comprising administering to said subject DMB as the free acid, a pharmaceutically acceptable salt, or ester thereof, wherein after the administration the percentage of fetal hemoglobin in the blood of the subject increases. In some embodiments, the total daily dose of DMB does not exceed 100 mg/kg, does not exceed 90 mg/kg, does not exceed 80 mg/kg, does not exceed 70 mg/kg, does not exceed 60 mg/kg, does not exceed 50 mg/kg, does not exceed 40 mg/kg, does not exceed 35 mg/kg, does not exceed 30 mg/kg, does not exceed 25 mg/kg, does not exceed 20 mg/kg, does not exceed 15 mg/kg, does not exceed 10 mg/kg, or does not exceed 5 mg/kg. In certain embodiments, the total daily dose of DMB is between 10 and 30 mg/kg, between 20 and 40 mg/kg, between 30 and 50 mg/kg, between 40 and 60 mg/kg, or between 5 and 20 mg/kg. In certain embodiments, the total daily dose of DMB is between 10 and 60 mg/kg, between 20 and 70 mg/kg, between 30 and 80 mg/kg, between 40 and 90 mg/kg, or between 50 and 100 mg/kg. In some embodiments, the total daily dose of DMB is less than about 80 mg/kg, less than about 70 mg/kg, less than about 60 mg/kg, less than about 50 mg/kg, less than about 40 mg/kg, less than about 35 mg/kg, less than about 30 mg/kg, less than about 25 mg/kg, less than about 20 mg/kg, less than about 15 mg/kg, or less than about 10 mg/kg.

Also provided herein are methods for increasing the percentage of fetal hemoglobin in the blood of a subject comprising administering to said subject DMB as the free acid, a pharmaceutically acceptable salt, or ester thereof, wherein the total daily dose of DMB is not more than 40 mg/kg, and wherein after the administration the percentage of fetal hemoglobin in the blood of the subject increases. In certain embodiments, the subject has been diagnosed with a beta thalassemia. In some embodiments, the total daily dose of DMB does not exceed 40 mg/kg, does not exceed 35 mg/kg, does not exceed 30 mg/kg, does not exceed 25 mg/kg, does not exceed 20 mg/kg, does not exceed 15 mg/kg, does not exceed 10 mg/kg, does not exceed 5 mg/kg, does not exceed 2 mg/kg, or does not exceed 1 mg/kg. In certain embodiments, the total daily dose of DMB is between 5 and 25 mg/kg, between 10 and 30 mg/kg, between 20 and 40 mg/kg, between 5 and 20 mg/kg, between 10 and 25 mg/kg, between 15 and 30 mg/kg, between 20 and 35 mg/kg, or between 25 and 40 mg/kg. In some embodiments, the total daily dose of DMB is less than about 40 mg/kg, less than about 35 mg/kg, less than about 30 mg/kg, less than about 25 mg/kg, less than about 20 mg/kg, less than about 15 mg/kg, or less than about 10 mg/kg.

In certain embodiments, the plasma concentration of DMB does not exceed a concentration of 90 µg/mL of DMB. In other embodiments, the plasma concentration does not exceed a concentration of 120 µg/mL of DMB. In some embodiments, the maximum plasma concentration of DMB is less than 150 µg/mL, less than 140 µg/mL, less than 130 µg/mL, less than 120 µg/mL, less than 110 µg/mL, less than 100 µg/mL, less than 90 µg/mL, less than 80 µg/mL, less than 70 µg/mL, less than 60 µg/mL, less than 50 µg/mL, less than 40 µg/mL, less than 30 µg/mL, or less than 20 µg/mL. In some embodiments, the plasma concentration of DMB is between 50 and 100 µg/mL, between 40 and 90 µg/mL, between 30 and 80 µg/mL, between 25 and 90 µg/mL, or between 20 and 100 µg/mL. In certain embodiments, the plasma concentration of DMB is between 20 µg/mL and 90 µg/mL, or between 25 µg/mL and 120 µg/mL, or between 30 µg/mL and 150 µg/mL.

In some embodiments, the AUC is less than 2500 h*µg/mL, less than 2000 h*µg/mL, less than 1500 h*µg/mL, less than 1000 h*µg/mL, or less than 500 h*µg/mL.

In some embodiments, the percentage of fetal hemoglobin in the blood of a subject increases after one week of administering as compared to baseline. In other embodiments, the percentage of fetal hemoglobin in the blood of a subject increases after two weeks of administering as compared to baseline. In certain embodiments, the percentage of fetal hemoglobin in the blood of a subject increases after four weeks of administering as compared to baseline. In some embodiments, the percentage of fetal hemoglobin in the blood of a subject increases after one day of administering as compared to baseline. In certain embodiments, the percentage of fetal hemoglobin in the blood of a subject increases after 3 days of administering as compared to baseline.

In some embodiments, the methods for increasing the percentage of fetal hemoglobin further comprise administering to the subject hydroxyurea, decitabine, an HDAC inhibitor, or a combination thereof. In certain embodiments, the HDAC inhibitor is MS-275.

In some embodiments, the 2,2-dimethylbutyrate is administered as sodium 2,2-dimethylbutyrate. In certain embodiments, the administration of the DMB is by oral administration.

In certain embodiments, the amount of fetal globin in the blood of the subject increases. In some embodiments, the number of F-cells in the blood of the subject increases. In certain embodiments, the number of F-reticulocytes in the blood of the subject increases. In some embodiments, the amount of fetal hemoglobin in the blood of the subject increases. In certain embodiments, the amount of total hemoglobin in the blood of the subject increases. In some embodiments, the percentage of reticulocytes in the blood of the subject increases. In certain embodiments, the number of reticulocytes in the blood of the subject increases. In some embodiments, hematocrit increases. In certain embodiments, red blood cell production increases.

In some embodiments, the administration of DMB is by pulsed administration. In certain embodiments, the pulsed administration comprises administering DMB for about 8 weeks, followed by not administering DMB for about 4 weeks. In some embodiments, the pulsed administration comprises administering DMB for about 6 weeks, followed by not administering DMB for about 2 weeks. In certain embodiments, the pulsed administration comprises administering DMB for about 4 weeks, followed by not administering DMB for about 2 weeks. In some embodiments, the pulsed administration comprises administering DMB for about 2 weeks, followed by not administering DMB for about 2 weeks. In some embodiments, pulsed administration comprises pulses of administering DMB for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In certain embodiments, pulsed administration comprises intervals of not administering DMB of about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In some embodiments, administration is continuous. In certain embodiments, administration is for the lifetime of the subject.

Further provided herein are methods for increasing the percentage of fetal hemoglobin in the blood of a subject diagnosed with sickle cell disease, comprising administering to said subject DMB as the free acid, a pharmaceutically acceptable salt, or ester thereof, wherein after the administration the percentage of fetal hemoglobin in the blood of the subject increases. In some embodiments, the total daily dose of DMB does not exceed 100 mg/kg, does not exceed 90 mg/kg, does not exceed 80 mg/kg, does not exceed 70 mg/kg, does not exceed 60 mg/kg, does not exceed 50 mg/kg, does not exceed 40 mg/kg, does not exceed 35 mg/kg, does not exceed 30 mg/kg, does not exceed 25 mg/kg, does not exceed 20 mg/kg, does not exceed 15 mg/kg, or does not exceed 10 mg/kg. In certain embodiments, the total daily dose of DMB is between 10 and 30 mg/kg, between 20 and 40 mg/kg, between 30 and 50 mg/kg, between 40 and 60 mg/kg, between 50 and 70 mg/kg, between 40 and 80 mg/kg, between 50 and 90 mg/kg, between 60 and 100 mg/kg, between 30 and 70 mg/kg, between 20 and 60 mg/kg, between 10 and 50 mg/kg, or between 5 and 20 mg/kg. In some embodiments, the total daily dose of DMB is less than about 100 mg/kg, less than about 90 mg/kg, less than about 80 mg/kg, less than about 70 mg/kg, less than about 60 mg/kg, less than about 50 mg/kg, less than about 40 mg/kg, less than about 35 mg/kg, less than about 30 mg/kg, less than about 25 mg/kg, less than about 20 mg/kg, less than about 15 mg/kg, or less than about 10 mg/kg.

In certain embodiments, the plasma concentration of DMB does not exceed a concentration of 90 µg/mL of DMB. In other embodiments, the plasma concentration does not exceed a concentration of 120 µg/mL of DMB. In certain embodiments, the plasma concentration of DMB does not exceed a concentration of 150 µg/mL. In some embodiments, the plasma concentration of DMB does not exceed a concentration of 200 µg/mL. In certain embodiments, the plasma concentration of DMB does not exceed a concentration of 250 µg/mL. In some embodiments, the plasma concentration of DMB is between 20 µg/mL and 90 µg/mL, or between 25 µg/mL and 120 µg/mL, between 30 µg/mL and 150 µg/mL, or between 30 µg/mL and 250 µg/mL. In certain embodiments, the maximum plasma concentration of DMB is less than 300 µg/mL, less than 250 µg/mL, less than 200 µg/mL, less than 150 µg/mL, less than 140 µg/mL, less than 130 µg/mL, less than 120 µg/mL, less than 110 µg/mL, less than 100 µg/mL, less than 90 µg/mL, less than 80 µg/mL, less than 70 µg/mL, less than 60 µg/mL, less than 50 µg/mL, less than 40 µg/mL, less than 30 µg/mL, or less than 20 µg/mL. In certain embodiments, the AUC is less than 3500 h*µg/mL, less than 2000 h*µg/mL, less than 2500 h*µg/mL, less than 2000 h*µg/mL, less than 1500 h*µg/mL, less than 1000 h*µg/mL, or less than 500 h*µg/mL.

Also provided herein are methods for increasing the percentage of fetal hemoglobin in the blood of a subject, comprising administering to said subject 2,2-dimethylbutyrate (DMB) as the free acid, a pharmaceutically acceptable salt, or ester thereof, wherein the total daily dose of DMB is less than the maximum tolerated dose. Also provided herein are methods for increasing the percentage of fetal hemoglobin in a subject, comprising administering to said subject DMB as the free acid, a pharmaceutically acceptable salt, or ester thereof, wherein the total daily dose of DMB is less than 80% of the maximum tolerated dose, and wherein after the administration the percentage of total hemoglobin in the blood of the subject increases. Further provided herein are methods for increasing total hemoglobin in the blood of a subject, comprising administering to said subject DMB as the free acid, a pharmaceutically acceptable salt, or ester thereof, wherein the total daily dose of DMB is less than the maximum tolerated dose. Also provided herein are methods for increasing in a subject total hemoglobin, hematocrit, red blood cells, or a combination thereof, comprising administering to said subject DMB as the free acid, a pharmaceutically acceptable salt, or ester thereof, wherein the total daily dose of DMB is less than the maximum tolerated dose.

In some embodiments, the methods further comprise administering to said subject hydroxyurea, decitabine, an HDAC inhibitor, or a combination thereof. In certain embodiments, the HDAC inhibitor is MS-275. In some embodiments, the 2,2-dimethylbutyrate is administered as sodium 2,2-dimethylbutyrate. In certain embodiments, the 2,2-dimethylbutyrate is administered orally.

In some embodiments, the total daily dose of DMB is more than 25% and less than 75% of the maximum tolerated dose. In other embodiments, the total daily dose of DMB is less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2%, or less than 1% of the maximum tolerated dose.

In certain embodiments, the total daily dose of DMB is less than 100 mg/kg, less than 90 mg/kg, less than 80 mg/kg, less than 70 mg/kg, less than 60 mg/kg, less than 50 mg/kg, less than 40 mg/kg, less than 35 mg/kg, less than 30 mg/kg, less than 25 mg/kg, less than 20 mg/kg, or less than 10 mg/kg. In some embodiments, the total daily dose is about 100 mg/kg, about 90 mg/kg, about 80 mg/kg, about 70 mg/kg, about 60 mg/kg, about 50 mg/kg, about 40 mg/kg, about 35 mg/kg, about 30 mg/kg, about 25 mg/kg, about 20 mg/kg, about 10 mg/kg, or about 5 mg/kg. In specific embodiments, the total daily dose is less than about 40 mg/kg.

In some embodiments, the plasma concentration does not exceed a concentration of 90 µg/mL of DMB. In certain embodiments, the mean plasma concentration of DMB is less than 150 µg/mL, less than 140 µg/mL, less than 130 µg/mL, less than 120 µg/mL, less than 110 µg/mL, less than 100 µg/mL, less than 90 µg/mL, less than 80 µg/mL, less than 70 µg/mL, less than 60 µg/mL, less than 50 µg/mL, less than 40 µg/mL, less than 30 µg/mL, less than 20 µg/mL, or less than 15 µg/mL.

In certain embodiments, the subject has been diagnosed with a blood disorder. In other embodiments, the subject has been diagnosed with an anemia. In some embodiments, the blood disorder is sickle cell disease. In other embodiments, the blood disorder is a beta thalassemia disorder or syndrome. In certain embodiments, the beta thalassemia disorder or syndrome is beta thalassemia intermedia. In some embodiments, the beta thalassemia is beta thalassemia major. In certain embodiments, the beta thalassemia is beta thalassemia minor (beta thalassemia trait). In some embodiments, the beta thalassemia is HbE beta thalassemia. In certain embodiments, the beta thalassemia is HbS beta thalassemia.

In certain embodiments, the amount of fetal hemoglobin in the blood of the subject increases. In other embodiments, the amount of total hemoglobin in the blood of the subject increases.

In some embodiments, the subject is a mammal. In certain embodiments, the mammal is an animal. In some embodiments, the animal is a horse. In certain embodiments, the mammal is a human. In some embodiments, the human is a child. In certain embodiments, the human is under the age of 18. In some embodiments, the human is under the age of 10. In some embodiments, the human is under the age of 2.

In some embodiments, administering DMB does not suppress erythropoiesis at concentrations associated with biologic activity. In certain embodiments, administering DMB stimulates cell proliferation. In some embodiments, administering DMB inhibits apoptosis of erythroid progenitors. In further embodiments, administering DMB stimulates erythroid cell proliferation and survival. In some embodiments, administering DMB stimulates erythroid cell proliferation. In certain embodiments, administering DMB stimulates erythroid cell survival. In some embodiments, administering DMB stimulates red blood cell production. In certain embodiments, administering DMB leads to a longer survival of sickled blood cells.

In some embodiments, administering DMB stimulates erythropoiesis. In certain embodiments, administering DMB induces expression of the fetal globin gene promoter. In some embodiments, administering DMB increases fetal globin levels. In certain embodiments, administering DMB increases RBC production. In some instances, increased RBC production is assayed by reticulocytes, total hemoglobin (Hgb), and hematocrit (Hct).

In certain embodiments, administering DMB increases the amount of fetal globin in the blood of the subject. In some embodiments, administering DMB increases the amount of fetal hemoglobin in the blood of the subject. In certain embodiments, administering DMB increases the amount of total hemoglobin in the blood of the subject. In some embodiments, administering DMB increases the percentage of reticulocytes in the blood of the subject. In certain embodiments, administering DMB increases the number of reticulocytes in the blood of the subject. In some embodiments, administering DMB increases hematocrit.

In contrast to hydroxyurea, DMB is effective at increasing % HbF at a total daily dose which is below the maximum tolerated dose. In some instances, administering DMB does not necessitate the careful dose titration currently required for treatment with hydroxyurea. Furthermore, in certain instances, DMB is unexpectedly more effective at increasing the percentage of HbF in the blood of subjects with a blood disorder (e.g., beta thalassemia patients) at low daily doses than at higher daily doses which approach the MTD (see Example 12).

In addition, the total daily dose of DMB, which is effective in increasing the percentage of HbF, is significantly lower than the dose required for other SCFAD like arginine butyrate allowing for oral administration of DMB. Increasing the percentage of HbF and treating beta thalassemia by administering arginine butyrate to a patient with beta thalassemia requires total daily doses of 500-750 mg/kg/day, which in most instances have to be infused daily over a 10-16 hour period. In contrast, in some instances, the total daily dose of DMB is only 5-40 mg/kg/day, which in most instances can be administered orally.

Further, in some embodiments, a total daily dose of DMB of only 5-40 mg/kg/day stimulates erythroid cell proliferation and/or survival resulting in increased total hemoglobin levels.

In some embodiments of the methods herein, 2,2-dimethylbutyrate is administered as sodium 2,2-dimethylbutyrate. 2,2-Dimethylbutyrate includes, but is not limited to, 2,2-dimethylbutyric acid, sodium 2,2-dimethylbutyrate, potassium 2,2-dimethylbutyrate, magnesium 2,2-dimethylbutyrate, calcium 2,2-dimethylbutyrate, arginine 2,2-dimethylbutyrate, lysine 2,2-dimethylbutyrate, choline 2,2-dimethylbutyrate, methyl 2,2-dimethylbutyrate (2,2-dimethylbutyric acid methyl ester), ethyl 2,2-dimethylbutyrate, propyl 2,2-dimethylbutyrate, or isopropyl 2,2-dimethylbutyrate.

In certain embodiments of the methods herein, the DMB is administered daily. In further embodiments, administration is continuous. In some embodiments, the administration of DMB is by pulsed administration. In certain embodiments, pulsed administration comprises administering DMB pulses for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In some embodiments, pulsed administration comprises intervals of not administering DMB of about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In certain embodiments, administration is for the lifetime of the subject.

In some embodiments, DMB is administered every other day. In certain embodiments, the pulsed administration comprises administering DMB for about 5 days per week. In some embodiments, the pulsed administration comprises administering DMB for about 5 days, followed by not administering DMB for about 2 days. In certain embodiments, the pulsed administration comprises administering DMB for about 2 weeks, followed by not administering DMB for about 1 week. In some embodiments, the pulsed administration comprises administering DMB for about 2 weeks, followed by not administering DMB for about 2 weeks. In certain embodiments, the pulsed administration comprises administering DMB for about 4 weeks, followed by not administering DMB for about 1 week. In some embodiments, the pulsed administration comprises administering DMB for about 4 weeks, followed by not administering DMB for about 2 weeks. In further embodiments, the pulsed administration comprises administering DMB for about 6 weeks, followed by not administering DMB for about 2 weeks. In certain embodiments, the pulsed administration comprises administering DMB for about 8 weeks, followed by not administering DMB for about 2 weeks. In some embodiments, the pulsed administration comprises administering DMB for about 8 weeks, followed by not administering DMB for about 4 weeks.

In some instances, administering DMB to a subject with one genotype of beta thalassemia is more effective in raising % HbF than administering DMB to a subject with a different genotype of beta thalassemia. Further provided herein are methods comprising diagnosing a beta thalassemia genotype of a patient, determining a treatment plan considering the beta thalassemia genotype, and optionally increasing the percentage of fetal hemoglobin in the blood of the patient, comprising administering to the patient DMB as the free acid, a pharmaceutically acceptable salt, or ester thereof, wherein the total daily dose of DMB is less than the maximum tolerated dose.

Also provided herein is a method of increasing the percentage of fetal hemoglobin in the blood of a subject, comprising administering to said subject an oral formulation of DMB as the free acid, a pharmaceutically acceptable salt, or ester thereof, at a unit dose of up to about 1 mg/kg, about 2 mg/kg, about 5 mg/kg, about 10 mg/kg, about 15, mg/kg, about 20 mg/kg, about 25 mg/kg, about 30 mg/kg, about 35 mg/kg, or about 40 mg/kg.

Further provided herein is a method of increasing the percentage of fetal hemoglobin in the blood of a subject, comprising providing a unit dose in the form of a capsule or tablet comprising about 2000 mg, about 1750 mg, about 1500 mg, about 1250 mg, about 1000 mg, about 900 mg, about 800 mg, about 750 mg, about 700 mg, about 600 mg, about 500 mg, about 400 mg, about 300 mg, about 250 mg, about 200 mg, about 175 mg, about 150 mg, about 125 mg, about 100 mg about 75 mg or about 50 mg of DMB, or a pharmaceutically acceptable salt or ester thereof, and a pharmaceutically acceptable excipient. In some instances, a unit dose is formulated in a gelatin capsule along with one or more excipients, for example, lactose, cellulose, glycolate, and/or magnesium stearate. Milligrams per unit dose can refer to either the free acid form of DMB, or DMB in a salt or ester form.

Also provided herein are methods method for increasing the percentage of fetal hemoglobin in the blood of a human diagnosed with a blood disorder, comprising administering to said subject sodium DMB, wherein the total daily dose of sodium DMB is less than 80 mg/kg per day, and wherein after the administration the percentage of fetal hemoglobin in the blood of the subject increases.

Further provided herein is a method comprising diagnosing a type of beta thalassemia syndrome of a patient, determining a treatment plan considering the type of beta thalassemia syndrome, and optionally increasing the percentage of fetal hemoglobin in the blood of the patient, comprising administering to said patient DMB as the free acid, a pharmaceutically acceptable salt, or ester thereof, wherein the total daily dose of DMB is less than the maximum tolerated dose.

A subject that receives any of the DMB formulations herein may also receive one or more of the following treatments: hydroxyurea, decitabine, folic acid, opioids, analgesics, antibiotics, forms of erythropoietin, or HDAC inhibitors. Therefore, the present invention contemplates a method for treating a subject suffering from a blood disorder by administering to the subject any of the DMB formulations herein in the dose levels and/or dose units described herein as well as one or more other therapeutic agents, such as any of the ones selected from the group consisting of, but not limited to: hydroxyurea, decitabine, folic acid, opioids, analgesics, antibiotics, forms of erythropoietin, and HDAC inhibitors.

The term "subject" as used herein refers to a vertebrate, preferably a mammal, more preferably a primate, still more preferably a human. Mammals include, without limitation, humans, primates, wild animals, feral animals, farm animals, sports animals, and pets. In certain embodiments, the subject is a mammal. In some embodiments, the mammal is an animal. In certain embodiments, the animal is a horse. In specific embodiments, the mammal is a human. In some embodiments, the human is a child. In certain embodiments, the human is under the age of 18. In some embodiments, the human is under the age of 10. In some embodiments, the human is under the age of 2.

The interrelationship of dosages for animals and humans (based on milligrams per meter squared of body surface) is described in Freireich, et al., Cancer Chemother Rep 50: 219 (1966). Body surface area may be approximately determined from height and weight of the patient. See, e.g., Scientific Tables, Geigy Pharmaceuticals, Ardley, N.Y., 1970, 537.

Methods of Treatment

In some instances, responsiveness of the blood disorder to the treatment methods of the invention is measured directly by comparison against conventional drugs (for example, for certain blood disorders, hydroxyurea, HDAC inhibitors, or erythropoietin), or are inferred based on an understanding of disease etiology and progression. For example, there are a number of HbF expression assay systems that are widely accepted in the art as predictive of in vivo effects. Thus, the showing that a treatment method of this invention resulting in the induction of HbF expression in these assays is evidence of the clinical utility of these for treating SCD and/or a thalassemia, i.e., a blood disorder.

In one embodiment of the invention, "treatment" or "treating" refers to an amelioration of SCD and/or a thalassemia, i.e., a blood disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of SCD and/or a thalassemia, i.e., a blood disorder, either physically, e.g., stabilization of a discernible symptom, physiologically, e.g., stabilization of a physical parameter, or both. In yet another embodiment, "treatment" or "treating" refers to delaying the onset of SCD and/or a thalassemia, i.e., a blood disorder, or symptoms thereof.

Compositions administered according to methods of the invention can be assayed in vitro or in vivo, for the desired therapeutic or prophylactic activity, prior to use in humans. In some instances, animal model systems are used to demonstrate the safety and efficacy of compounds of this invention.

Without wishing to be bound by theory, it is believed that carrying out the treatment methods of this invention results in the induction of gene expression, for example, fetal hemoglobin expression and, as a result, in the treatment or prevention of SCD and/or a thalassemia, i.e., a blood disorder. It should be noted, however, that the treatment methods might exert their effect via a secondary or a different activity, such as, without limitation, stimulating hematopoiesis, erythropoiesis, and increasing self-renewal of normal stem cells.

Provided herein are methods for treating a blood disorder in a subject, comprising administering to said subject: a) 2,2-dimethylbutyrate (DMB) as the free acid, a pharmaceutically acceptable salt, or ester thereof, and b) one or more agents selected from the group consisting of hydroxyurea, decitabine, and an HDAC inhibitor. In certain embodiments, after the administration the percentage of fetal hemoglobin in the blood of the subject increases. In some embodiments, the percentage of fetal hemoglobin in the blood of a subject increases after one week of administering as compared to baseline. In other embodiments, the percentage of fetal hemoglobin in the blood of a subject increases after two weeks of administering as compared to baseline. In certain embodiments, the percentage of fetal hemoglobin in the blood of a subject increases after four weeks of administering as compared to baseline. In some embodiments, the percentage of fetal hemoglobin in the blood of a subject increases after one day of administering as compared to baseline. In certain embodiments, the percentage of fetal hemoglobin in the blood of a subject increases after 3 days of administering as compared to baseline.

In some embodiments of the methods for treating a blood disorder in a subject, the blood disorder is an anemia. In certain embodiments, the blood disorder is a sickle cell syndrome. In some embodiments, the blood disorder is a beta thalassemia syndrome.

In some embodiments, the 2,2-dimethylbutyrate is administered as sodium 2,2-dimethylbutyrate. In certain embodiments, the DMB is administered orally. In some embodiments, the HDAC inhibitor is MS-275. In certain embodiments, the administration of the one or more agents is orally. In some embodiments, the administration of the DMB and the one or more agents is orally. In certain embodiments, the DMB and the one or more agents are administered in a combined oral dosage form.

In some embodiments, the total daily dose of DMB is less than 100 mg/kg, less than 90 mg/kg, less than 80 mg/kg, less than 70 mg/kg, less than 60 mg/kg, less than 50 mg/kg, less than 40 mg/kg, less than 30 mg/kg, less than 20 mg/kg, or less than 10 mg/kg. In certain embodiments, the mean plasma concentration does not exceed a concentration of 90 µg/mL of DMB. In some embodiments, the mean plasma concentration of DMB is less than 300 µg/mL, less than 250 µg/mL, less than 200 µg/mL, less than 150 µg/mL, less than 140 µg/mL, less than 130 µg/mL, less than 120 µg/mL, less than 110 µg/mL, less than 100 µg/mL, less than 90 µg/mL, less than 80 µg/mL, less than 70 µg/mL, less than 60 µg/mL, less than 50 µg/mL, less than 40 µg/mL, less than 30 µg/mL, less than 20 µg/mL, less than 15 µg/mL, less than 10 µg/mL, or less than 5 µg/mL.

In certain embodiments, the amount of fetal globin in the blood of the subject increases. In some embodiments, the number of F-cells in the blood of the subject increases. In certain embodiments, the number of F-reticulocytes in the blood of the subject increases. In some embodiments, the amount of fetal hemoglobin in the blood of the subject increases. In certain embodiments, the amount of total hemoglobin in the blood of the subject increases. In some embodiments, the percentage of reticulocytes in the blood of the subject increases. In certain embodiments, the number of reticulocytes in the blood of the subject increases. In some embodiments, hematocrit increases. In certain embodiments, red blood cell production increases.

In some embodiments, the administration of DMB is by pulsed administration. In certain embodiments, the pulsed administration comprises administering DMB for about 8 weeks, followed by not administering DMB for about 4 weeks. In some embodiments, the pulsed administration comprises administering DMB for about 6 weeks, followed by not administering DMB for about 2 weeks. In certain embodiments, the pulsed administration comprises administering DMB for about 4 weeks, followed by not administering DMB for about 2 weeks. In some embodiments, the pulsed administration comprises administering DMB for about 2 weeks, followed by not administering DMB for about 2 weeks. In some embodiments, pulsed administration comprises pulses of administering DMB for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In certain embodiments, pulsed administration comprises intervals of not administering DMB of about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In some embodiments, administration is continuous. In certain embodiments, administration is for the lifetime of the subject.

In some embodiments, the subject is a mammal. In certain embodiments, the mammal is an animal. In some embodiments, the animal is a horse. In certain embodiments, the mammal is a human. In some embodiments, the human is a child. In certain embodiments, the human is under the age of 18. In some embodiments, the human is under the age of 10. In some embodiments, the human is under the age of 2.

Further provided herein are methods for treating a subject comprising administering to said patient DMB as the free acid, a pharmaceutically acceptable salt, or ester thereof, wherein the total daily dose of DMB is not more than 40 mg/kg. In some embodiments, after the administration the percentage of fetal hemoglobin in the blood of the subject increases. In certain embodiments, the subject has been diagnosed with a beta thalassemia. In some embodiments, the total daily dose of DMB is less than about 40 mg/kg, less than about 35 mg/kg, less than about 30 mg/kg, less than about 25 mg/kg, less than about 20 mg/kg, less than about 15 mg/kg, or less than about 10 mg/kg.

In some embodiments, the percentage of fetal hemoglobin in the blood of a subject increases after one week of administering as compared to baseline. In other embodiments, the percentage of fetal hemoglobin in the blood of a subject increases after two weeks of administering as compared to baseline. In certain embodiments, the percentage of fetal hemoglobin in the blood of a subject increases after four weeks of administering as compared to baseline. In some embodiments, the percentage of fetal hemoglobin in the blood of a subject increases after one day of administering as compared to baseline. In certain embodiments, the percentage of fetal hemoglobin in the blood of a subject increases after 3 days of administering as compared to baseline.

In some embodiments, the methods for treating a subject further comprise administering to the subject hydroxyurea, decitabine, an HDAC inhibitor, or a combination thereof. In certain embodiments, the HDAC inhibitor is MS-275.

In some embodiments, the 2,2-dimethylbutyrate is administered as sodium 2,2-dimethylbutyrate. In certain embodiments, the administration of the DMB is by oral administration.

In certain embodiments, the plasma concentration of DMB does not exceed a concentration of 90 µg/mL of DMB. In other embodiments, the plasma concentration does not exceed a concentration of 120 µg/mL of DMB. In certain embodiments, the plasma concentration of DMB does not exceed a concentration of 150 µg/mL. In some embodiments, the maximum plasma concentration of DMB is less than 300 µg/mL, less than 250 µg/mL, less than 200 µg/mL, less than 180 µg/mL, less than 170 µg/mL, less than 160 µg/mL, less than 150 µg/mL, less than 140 µg/mL, less than 130 µg/mL, less than 120 µg/mL, less than 110 µg/mL, less than 100 µg/mL, less than 90 µg/mL, less than 80 µg/mL, less than 70 µg/mL, less than 60 µg/mL, less than 50 µg/mL, less than 40 µg/mL, less than 30 µg/mL, or less than 20 µg/mL. In certain embodiments, the plasma concentration of DMB does not exceed a concentration of 90 µg/mL of DMB. In other embodiments, the plasma concentration does not exceed a concentration of 120 µg/mL of DMB. In certain embodiments, the plasma concentration of DMB does not exceed a concentration of 150 µg/mL. In some embodiments, the plasma concentration of DMB does not exceed a concentration of 200 µg/mL. In certain embodiments, the plasma concentration of DMB does not exceed a concentration of 250 µg/mL. In some embodiments, the plasma concentration of DMB is between 20 µg/mL and 90 µg/mL, or between 25 µg/mL and 120 µg/mL, between 30 µg/mL and 150 µg/mL, or between 30 µg/mL and 250 µg/mL. In certain embodiments, the AUC is less than 3500 h*µg/mL, less than 3000 h*µg/mL, less than 2500 h*µg/mL, less than 2000 h*µg/mL, less than 1500 h*µg/mL, less than 1000 h*µg/mL, or less than 500 h*µg/mL.

In certain embodiments, the amount of fetal globin in the blood of the subject increases. In some embodiments, the number of F-cells in the blood of the subject increases. In certain embodiments, the number of F-reticulocytes in the blood of the subject increases. In some embodiments, the amount of fetal hemoglobin in the blood of the subject increases. In certain embodiments, the amount of total hemoglobin in the blood of the subject increases. In some embodiments, the percentage of reticulocytes in the blood of the subject increases. In certain embodiments, the number of reticulocytes in the blood of the subject increases. In some embodiments, hematocrit increases. In certain embodiments, red blood cell production increases.

In some embodiments, the administration of DMB is by pulsed administration. In certain embodiments, the pulsed administration comprises administering DMB for about 8 weeks, followed by not administering DMB for about 4 weeks. In some embodiments, the pulsed administration comprises administering DMB for about 6 weeks, followed by not administering DMB for about 2 weeks. In certain embodiments, the pulsed administration comprises administering DMB for about 4 weeks, followed by not administering DMB for about 2 weeks. In some embodiments, the pulsed administration comprises administering DMB for about 2 weeks, followed by not administering DMB for about 2 weeks. In some embodiments, pulsed administration comprises pulses of administering DMB for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In certain embodiments, pulsed administration comprises intervals of not administering DMB of about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In some embodiments, administration is continuous. In certain embodiments, administration is for the lifetime of the subject.

Also provided herein are methods for treating a blood disorder in a subject, comprising administering to said subject 2,2-dimethylbutyrate (DMB) as the free acid, a pharmaceutically acceptable salt, or ester thereof, wherein the total daily dose of 2,2-dimethylbutyrate is less than the maximum tolerated dose. Also provided herein are methods for treating a blood disorder in a subject, comprising administering to said subject DMB as the free acid, a pharmaceutically acceptable salt, or ester thereof, wherein the total daily dose of DMB is less than 80% of the maximum tolerated dose, and wherein after the administration the percentage of total hemoglobin in the blood of the subject increases. In some embodiments, the blood disorder is sickle cell disease. In other embodiments, the blood disorder is beta thalassemia. In some embodiments, the 2,2-dimethylbutyrate is administered as sodium 2,2-dimethylbutyrate. In certain embodiments, the 2,2-dimethylbutyrate is administered orally.

In some embodiments, the methods further comprise administering to said subject hydroxyurea, decitabine, an HDAC inhibitor, or a combination thereof. In certain embodiments, the HDAC inhibitor is MS-275. In some embodiments, the 2,2-dimethylbutyrate is administered as sodium 2,2-dimethylbutyrate. In certain embodiments, the 2,2-dimethylbutyrate is administered orally.

In some embodiments, the subject has been diagnosed with a blood disorder and the blood disorder is an anemia. In some embodiments, the blood disorder is a sickle cell syndrome. In other embodiments, the blood disorder is a beta thalassemia disorder or syndrome. In certain embodiments, the beta thalassemia disorder or syndrome is beta thalassemia intermedia.

In some embodiments, the total daily dose of 2,2-dimethylbutyrate is more than 25% and less than 75% of the maximum tolerated dose. In other embodiments, the total daily dose of 2,2-dimethylbutyrate is less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2%, or less than 1% of the maximum tolerated dose. In certain embodiments, the total daily dose of 2,2-dimethylbutyrate is less than 80 mg/kg, less than 60 mg/kg, less than 40 mg/kg, less than 30 mg/kg, less than 20 mg/kg, or less than 10 mg/kg. In some embodiments, the mean plasma concentration does not exceed a concentration of 90 µg/mL of 2,2-dimethylbutyrate. In certain embodiments, the mean plasma concentration of 2,2-dimethylbutyrate is less than 150 µg/mL, less than 140 µg/mL, less than 130 µg/mL, less than 120 µg/mL, less than 110 µg/mL, less than 100 µg/mL, less than 90 µg/mL, less than 80 µg/mL, less than 70 µg/mL, less than 60 µg/mL, less than 50 µg/mL, less than 40 µg/mL, less than 30 µg/mL, less than 20 µg/mL, less than 15 µg/mL, less than 10 µg/mL, or less than 5 µg/mL.

In certain embodiments, the amount of fetal globin in the blood of a subject increases. In some embodiments, the amount of fetal hemoglobin in the blood of the subject increases. In certain embodiments, the amount of total hemoglobin in the blood of the subject increases. In some embodiments, the percentage of reticulocytes in the blood of the subject increases. In certain embodiments, the number of reticulocytes in the blood of the subject increases. In some embodiments, hematocrit increases. In certain embodiments, red blood cell production increases.

In some embodiments, the administration of 2,2-dimethylbutyrate is by pulsed administration. In certain embodiments, the pulsed administration comprises administering 2,2-dimethylbutyrate for about 8 weeks, followed by not administering 2,2-dimethylbutyrate for about 4 weeks. In some embodiments, the pulsed administration comprises administering 2,2-dimethylbutyrate for about 6 weeks, followed by not administering 2,2-dimethylbutyrate for about 2 weeks. In certain embodiments, the pulsed administration comprises administering 2,2-dimethylbutyrate for about 4 weeks, followed by not administering 2,2-dimethylbutyrate for about 2 weeks. In some embodiments, the pulsed administration comprises administering 2,2-dimethylbutyrate for about 2 weeks, followed by not administering 2,2-dimethylbutyrate for about 2 weeks. In some embodiments, pulsed administration comprises pulses of administering 2,2-dimethylbutyrate for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In certain embodiments, pulsed administration comprises intervals of not administering 2,2-dimethylbutyrate of about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In some embodiments, administration is continuous. In certain embodiments, administration is for the lifetime of the subject.

In some embodiments, the subject is a mammal. In certain embodiments, the mammal is an animal. In some embodiments, the animal is a horse. In certain embodiments, the mammal is a human. In some embodiments, the human is a child. In certain embodiments, the human is under the age of 18. In some embodiments, the human is under the age of 10. In some embodiments, the human is under the age of 2.

A subject that receives any of the 2,2-dimethylbutyrate formulations herein may also receive one or more of the following treatments: hydroxyurea, decitabine, folic acid, opioids, analgesics, antibiotics, forms of erythropoietin. Therefore, the present invention contemplates a method for treating a subject suffering from a blood disorder by administering to the subject any of the 2,2-dimethylbutyrate formulations herein in the dose levels and/or dose units described herein as well as one or more other therapeutic agents, such as any of the ones selected from the group consisting of, but not limited to hydroxyurea, decitabine, folic acid, opioids, analgesics, antibiotics, and forms of erythropoietin.

Also provided herein, is a method of treating a blood disorder in a subject, comprising administering to said subject an oral formulation of DMB as the free acid, a pharmaceutically acceptable salt, or ester thereof, at a unit dose of up to 5 mg/kg, 10 mg/kg, 15, mg/kg, 20 mg/kg, 25 mg/kg, 30 mg/kg, 40 mg/kg. In some embodiments, a patient suffering from a blood disorder is administered an oral formulation of DMB as the free acid, a pharmaceutically acceptable salt, or ester thereof, at a total daily dose of up to 100 mg/kg/day, up to 90 mg/kg/day, up to 80 mg/kg/day, up to 70 mg/kg/day, up to 60 mg/kg/day, up to 50 mg/kg/day, up to 40 mg/kg/day, up to 30 mg/kg/day, up to 20 mg/kg/day, up to 15 mg/kg/day, up to 10 mg/kg/day, or up to 5 mg/kg/day.

Also provided herein is a method of treating a blood disorder in a subject, comprising providing a capsule or tablet comprising about 2000 mg, about 1750 mg, about 1500 mg, about 1250 mg, about 1000 mg, about 900 mg, about 800 mg, about 750 mg, about 700 mg, about 600 mg, about 500 mg, about 400 mg, about 300 mg, about 250 mg, about 200 mg, about 175 mg, about 150 mg, about 125 mg, about 100 mg about 75 mg or about 50 mg of DMB, or a pharmaceutically acceptable salt or ester thereof, and a pharmaceutically acceptable excipient. In some instances, a unit dose is formulated in a gelatin capsule along with one or more excipients, for example, lactose, cellulose, glycolate, and/or magnesium stearate. Milligrams per unit dose can refer to either the free acid form of DMB, or DMB in a salt or ester form.

The methods of the invention can further include the step of monitoring the subject, e.g., for any parameter related to improvement in clinical outcome. The subject can be monitored in one or more of the following periods: prior to beginning of treatment; during the treatment; or after one or more elements of the treatment have been administered. Monitoring can be used to evaluate the need for further treatment with the composition administered according to a method of the invention or for additional treatment with additional agents. Information about the monitoring can be recorded, e.g., in electronic or digital form.

The methods disclosed herein can be used in combination with one or more additional treatment modalities, including, but not limited to, surgery; radiation therapy, and chemotherapy.

Combination Therapy

In certain embodiments, the pharmaceutical composition is administered alone or in combination with other known compositions for treating blood disorders in a subject, e.g., a mammal. In some embodiments, mammals include cats, dogs, pigs, horses, cows, rats, mice, monkeys, chimpanzees, baboons, and humans. In specific embodiments, the mammal is a human. In some embodiments, the human is a child. In certain embodiments, the human is under the age of 18. In some embodiments, the human is under the age of 10. In some embodiments, the human is under the age of 2. In one embodiment, the subject is suffering from a blood disorder. In another embodiment, the subject is at risk of suffering from a blood disorder.

The language "in combination with" a known composition is intended to include simultaneous administration of the composition of the invention and the known composition, administration of the composition of the invention first, followed by the known composition and administration of the known composition first, followed by the composition of the invention. Any of the compositions known in the art for treating blood disorders can be used in the methods of the invention.

Further described herein is the finding that Sodium 2,2-dimethylbutyrate (sodium DMB) exhibits additive and/or synergistic activity with hydroxyurea (HU), decitabine, and/or a histone deacetylase (HDAC) inhibitor. In brief, DMB has been found to induce higher γ-globin expression levels when administered with hydroxyurea (HU), decitabine, or a histone deacetylase (HDAC) inhibitor.

Thus, in one aspect, the invention is directed to a method for increasing fetal hemoglobin in the blood of a subject, comprising administering to the subject a pharmaceutical composition comprising DMB as the free acid, a pharmaceutically acceptable salt, or ester thereof, and hydroxyurea. In another aspect, the invention is directed to a method for increasing fetal hemoglobin in the blood of a subject, comprising administering to the subject a pharmaceutical composition comprising DMB as the free acid, a pharmaceutically acceptable salt, or ester thereof, and decitabine. In still another aspect, the invention is directed to a method for increasing fetal hemoglobin in the blood of a subject, comprising administering to the subject a pharmaceutical composition comprising DMB as the free acid, a pharmaceutically acceptable salt, or ester thereof, and an HDAC inhibitor. In yet another aspect, the invention is directed to a method for increasing fetal hemoglobin in the blood of a subject, comprising administering to the subject a pharmaceutical composition comprising i) DMB as the free acid, a pharmaceutically acceptable salt, or ester thereof, and ii) hydroxyurea, decitabine and/or an HDAC inhibitor. In one embodiment of a method of the invention, the HDAC inhibitor is MS-275.

In a further aspect, the invention is directed to a method for treating a blood disorder in a subject, comprising administering to the subject a pharmaceutical composition comprising DMB as the free acid, a pharmaceutically acceptable salt, or ester thereof, and hydroxyurea. In another aspect, the invention is directed to a method for treating a blood disorder in a subject, comprising administering to the subject a pharmaceutical composition comprising DMB as the free acid, a pharmaceutically acceptable salt, or ester thereof, and decitabine. In still another aspect, the invention is directed to a method for treating a blood disorder in a subject, comprising administering to the subject a pharmaceutical composition comprising DMB as the free acid, a pharmaceutically acceptable salt, or ester thereof, and an HDAC inhibitor. In yet another aspect, the invention is directed to a method for treating a blood disorder in a subject, comprising administering to the subject a pharmaceutical composition comprising i) DMB as the free acid, a pharmaceutically acceptable salt, or ester thereof, and ii) hydroxyurea, decitabine and/or an HDAC inhibitor. In one embodiment of a method of the invention, the HDAC inhibitor is MS-275.

In one embodiment of a method of the invention, the blood disorder is a thalassemia. In another embodiment, the thalassemia is selected from beta thalassemia major, thalassemia intermedia, and hemoglobin E beta thalassemia.

In some embodiments, in addition to the use of DMB for the treatment of blood disorders, concomitant administration of other pharmaceutical and nutraceutical compounds occurs. For example, persons suffering from sickle cell disease are given DMB and hydroxyurea (to decrease occurrence of pain), folic acid supplements (for blood cell production), opioids or analgesics (for pain management), and/or antibiotics (for treating secondary infections). In further embodiments, administration of DMB for the treatment of blood disorders is combined with the administration of natural or synthetic erythropoietin. In certain instances, concomitant treatment with DMB and a second agent occurs at the same time, or on different regimen schedules.

DMB is an orally bio-available compound that is active at well tolerated doses. DMB is not a global HDAC inhibitor, but a modest erythropoietic stimulant that prolongs STAT-5 activation. Furthermore, DMB is well characterized in multiple species, including primates, has a half-life of 9 to 11 hours, and a favorable safety profile in normal volunteers.

In some instances, when hydroxyurea (HU) and DMB were administered to anemic baboons and γ-globin mRNA was assayed, γ-globin mRNA increased with increasing doses of DMB. In baboons treated with sequentially administered HU (3 days/week) γ-globin mRNA increased by 80-120% above baseline, treatment with DMB increased γ-globin mRNA by 290% above baseline, while treatment with the two-agent combination of HU and DMB increased γ-globin mRNA by 360%. A significantly larger increase in γ-globin mRNA was observed when HU and DMB were dosed together as compared to dosing HU or DMB individually (FIG. 1).

Figure 2:
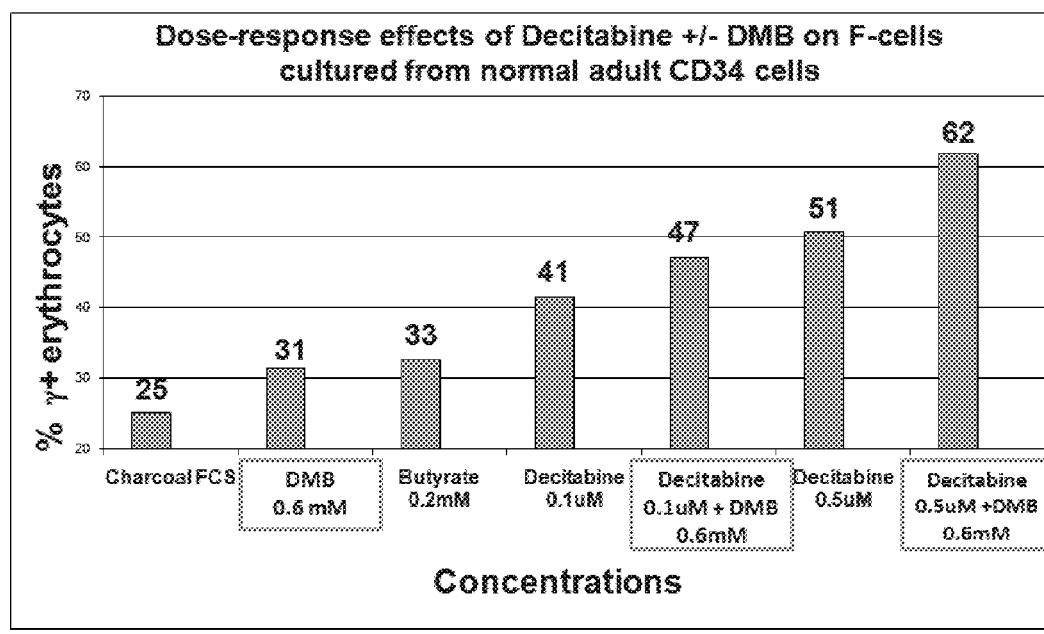
FIG. 2 is a graphic representation of the additive effects of decitabine and DMB on F-cells.

In further instances, HbF inducers were evaluated in combinations in erythroid progenitor cultures and additive effects were observed when DMB was dosed together with decitabine (FIG. 2). In Bfu-e cultures comparing DMB with or without decitabine, F-cells increased above baseline in cultures treated with DMB alone by 32-71%, with decitabine alone by 66-104%, and with the two-agent combination by 147% above F-cell levels in control cultures.

Figure 3:
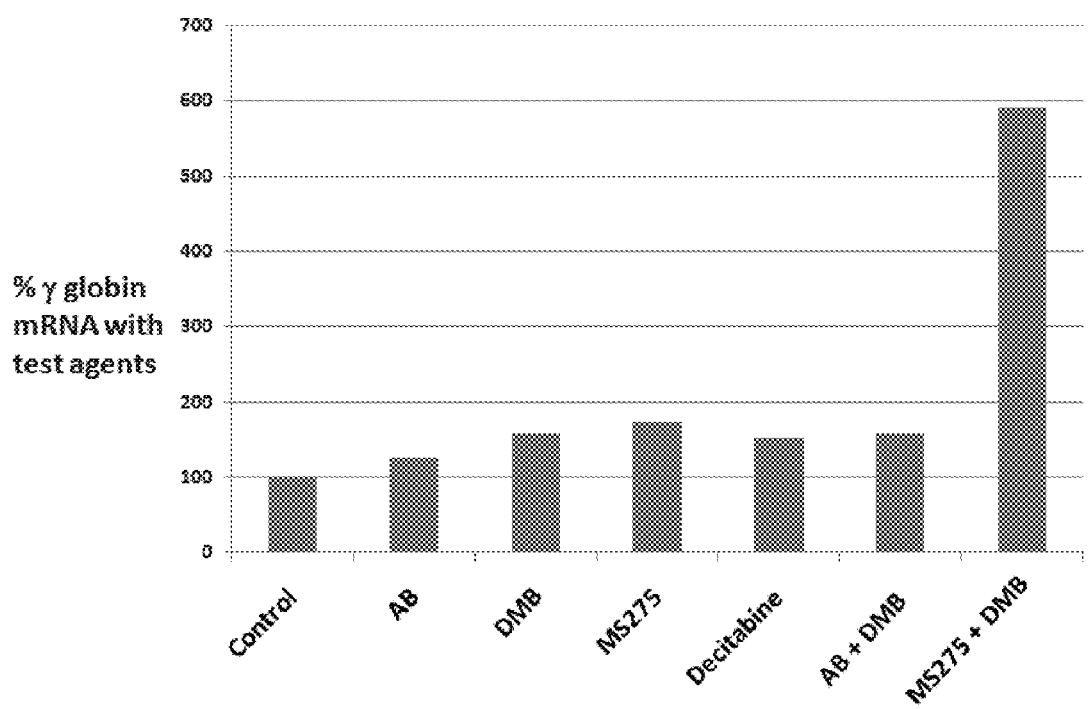
FIG. 3 is a graphic representation of synergistic effects on the induction of y-globin mRNA observed with DMB, arginine butyrate (AB), decitabine and the HDAC inhibitor on the MS275.

In some instances, a significant synergistic effect on the induction of γ-globin mRNA was observed when DMB and an HDAC inhibitor were dosed together. This increase was multiple time larger than with either agent alone (FIG. 3).

In some embodiments, DMB, as a dual-action oral γ-globin inducer that does not inhibit erythroid proliferation, has additive or synergistic activity when combined with HU, decitabine, or an HDAC inhibitor. In certain embodiments, administration of DMB in combination with HU, decitabine, an HDAC inhibitor, or a combination thereof is used in the treatment of a blood disorder. In some embodiments, the blood disorder is sickle cell disease. In other embodiments, the blood disorder is a thalassemia. In certain embodiments, administration of DMB in combination with HU, decitabine, an HDAC inhibitor, or a combination thereof, is used for increasing the percentage of fetal hemoglobin in the blood of a subject. In other embodiments, the combination is used for increasing total hemoglobin, hematocrit, or red blood cells in a subject.

In some embodiments, the methods described herein comprise administering to the subject an effective amount of DMB and an effective amount of one or more other therapeutic agents. In one embodiment of the invention where another therapeutic agent is administered to a subject, the effective amount of the composition comprising DMB administered according to a method of the invention is less than its effective amount would be where the other therapeutic agent is not administered. In another embodiment, the effective amount of the other therapeutic agent is less than its effective amount would be when the composition administered according to a method of the invention is not administered.

In some aspects described herein, the method includes an additional therapeutic modality. In some embodiments, the additional therapeutic modality is an HDAC inhibitor. In certain embodiments, the additional therapeutic modality is decitabine. In further embodiments, the additional therapeutic modality is hydroxyurea.

Decitabine (5-aza-2'-deoxycytidine) is a nucleoside analog drug—a drug that mimics a natural component of DNA. Decitabine and the related compound 5-azacytidine are unique amongst the large family of nucleoside analogue drugs in that it can bind to and deplete DNA methyl-transferase 1 (DNMT1). DNMT1 is an enzyme which plays a critical and central role in the machinery that represses genes. Most cells in the body, including cancer cells or blood disorder cells, such as sickle cells, contain the same complement of genes. The function and specialization of a cell is, therefore, determined by which of these genes are turned-on (activated), and which are turned-off (repressed). Activation refers to the expression of the protein encoded by the gene, while repression of the gene implies that the protein encoded by that gene is expressed at lower levels or not at all. Therefore, altering the levels of DNMT1 within a cell can have powerful effects on the pattern of gene-expression, function and specialization of a cell.

Histone deacetylase inhibitors (HDAC inhibitors), a class of compounds that interfere with the function of histone deacetylase, are contemplated as an additional agent for combination therapy. HDAC inhibitors include, without limitation, hydroxamic acids (for example, Trichostatin A), cyclic tetrapeptides (for example, trapoxin B), depsipeptides (for example, romidepsin), benzamides, electrophilic ketones, aliphatic acid compounds (for example, phenylbutyrate, valproic acid), SAHA/Vorinostat, FK228, Belinostat/PXD101, Panobinostat, MS-275, LAQ824/LBH589, CI994, MGCD0103, nicotinamide, NAD derivatives, dihydrocoumarin, naphthopyranone, and 2-hydroxynaphthaldehydes.

In some embodiments, DMB has additive HbF-inducing activity in combination with hydroxyurea, decitabine, or an HDAC inhibitor. In some instances, multiple agents are required for the correction of beta thalassemia major. In certain embodiments, agents with complementary molecular mechanisms induce higher γ-globin expression levels than single agents alone. Ideally, agents which inhibit cell proliferation are not used together in combination therapy.

With reference to the methods disclosed herein, the term "combination" refers to the use of one or more additional agents or therapies to treat the same patient, wherein the use or action of the agents or therapies overlap in time. The additional agents or therapies can be administered at the same time as the composition administered according to a method of the invention is administered, or sequentially in any order. Sequential administrations are administrations that are given at different times. The time between administration of the one agent and another agent can be minutes, hours, days, or weeks.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description and the examples that follow, one skilled in the art can easily ascertain the essential characteristics of the present invention, and without departing from the spirit and scope thereof, can make various changes and modifications of the invention to adapt it to various usages and conditions. For example, the compounds of the invention may be used as research tools (for example, to isolate new targets for performing drug discovery). The compounds may, for instance, be radiolabelled for imaging tissue or organs or be used to form bioconjugates for affinity assays. These and other uses and embodiments of the compounds and compositions of this invention will be apparent to those of ordinary skill in the art.

A combination therapy can include administering an agent that reduces the side effects of other therapies. A combination therapy can also include administering an agent that reduces the frequency of administration of other therapies. Useful combination therapies will be understood and appreciated by those of skill in the art. Potential advantages of such combination therapies include the ability to use less of each of the individual active ingredients to minimize toxic side effects, synergistic improvements in efficacy, improved ease of administration or use, and/or reduced overall expense of compound preparation or formulation.

Pharmaceutical Compositions

In some embodiments, the pharmaceutical composition administered according to a method of the invention are administered orally in effective dosages, depending upon the weight, body surface area, and condition of the subject being treated. In some instances, variations occur depending upon the species of the subject being treated and its individual response to said medicament, as well as on the type of pharmaceutical formulation chosen and the time period and interval at which such administration is carried out.

In some embodiments, the administration of the pharmaceutical composition according to a method of the invention is carried out in single or multiple doses. For example, the composition can be administered in a wide variety of different dosage forms, i.e., it may be combined with various pharmaceutically acceptable inert carriers in the form of tablets, dragees, capsules, lozenges, troches, hard candies, aqueous suspensions, elixirs, syrups, and the like. Such carriers include solid diluents or fillers, sterile aqueous media and various non-toxic organic solvents, etc. Moreover, oral pharmaceutical compositions can be suitably sweetened and/or flavored.

In certain embodiments, pharmaceutical compositions of the invention are suitable for oral administration. Suitable pharmaceutical compositions for oral administration can be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient. When intended for oral administration in a solid dosage form (i.e., as capsules, tablets, pills and the like), the pharmaceutical compositions of the invention will typically comprise a compound of the present invention as the active ingredient and one or more pharmaceutically-acceptable carriers, such as sodium citrate or dicalcium phosphate. Optionally or alternatively, such solid dosage forms may also comprise: filters or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

If desired, pharmaceutical compositions of the present invention may also be formulated to provide slow or controlled release of the active ingredient using, by way of example, hydroxypropyl methyl cellulose in varying proportions; or other polymer matrices, liposomes and/or microspheres. Sustained release compositions can be formulated including those wherein the active component is derivatized with differentially degradable coatings, e.g., by microencapsulation, multiple coatings, etc.

It will be appreciated that the actual preferred amounts of active compounds used in a given therapy will vary according to the particular compositions formulated. Optimal administration rates for a given protocol of administration can be readily ascertained by those skilled in the art using conventional dosage determination tests conducted with regard to the foregoing guidelines.

It will also be understood that normal, conventionally known precautions will be taken regarding the administration of the compounds of the invention generally to ensure their efficacy under normal use circumstances. Especially when employed for treatment of humans and animals in vivo, the practitioner should take all sensible precautions to avoid conventionally known contradictions and toxic effects.

The composition, shape, and type of dosage forms of the invention will typically vary depending on their use. This aspect of the invention will be readily apparent to those skilled in the art. See, e.g., Remington's Pharmaceutical Sciences (1990) 18th ed., Mack Publishing, Eastern Pa.

In certain embodiments, the pharmaceutical compositions of the invention is packaged in a unit dosage form. The term "unit dosage form" or "unit dose" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like. Unit doses can also be prepared to contain any useful amount of an active ingredient (e.g., sodium DMB). For example, a unit dose can comprise 10 mg, 20 mg, 30 mg, 40 mg, 50 mg, 60 mg, 70 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 210 mg, 220 mg, 225 mg, 230 mg, 240 mg, 250 mg, 260 mg, 270 mg, 275 mg, 280 mg, 290 mg, 300 mg, 310 mg, 320 mg, 325 mg, 330 mg, 340 mg, 350 mg, 360 mg, 370 mg, 375 mg, 380 mg, 390 mg, 400 mg, 410 mg, 420 mg, 425 mg, 430 mg, 440 mg, 450 mg, 460 mg, 470 mg, 475 mg, 480 mg, 490 mg, 500 mg, 510 mg, 520 mg, 525 mg, 530 mg, 540 mg, 550 mg, 560 mg, 570 mg, 575 mg, 580 mg, 590 mg, 600 mg, 625 mg, 650 mg, 675 mg, 700 mg, 750 mg, 800 mg, 850 mg, 900 mg, 950 mg, 1000 mg, 1100 mg, 1200 mg, 1250 mg, 1300 mg, 1400 mg, 1500 mg, 1600 mg, 1700 mg, 1750 mg, 1800 mg, 1900 mg, or 2000 mg of DMB per unit dose. Milligrams per unit dose can refer to either the free acid form of DMB, or DMB in a salt or ester form. In some embodiments, unit doses are packaged in a kit comprising an insert instructing the subject on the appropriate dosage.

Administrations can be repeated on consecutive or non-consecutive days. Thus, daily administrations can be performed for 2, 3, 4, 5, 6, 7, 8, 9, 10, 11, 12, 13, 14, 15, 16, 17, 18, 19, 20, 25, 30, 35, 40, 45, 50, 55, 60, or more consecutive days. For example, administration of 10 mg/kg of DMB is performed twice a day (at a total daily dose of 20 mg/kg) for 14 consecutive days. Alternatively, administration may occur for multiple days, but on non-consecutive days separated by 1, 2, 3, 4, 5, 6, 7, 8, 9, 10 or more days. For example, administration of 15 mg/kg of DMB is performed on every other day following therapy onset. In another instance, administration of DMB is performed for 5 days per week. Such dosing regimens can be tailored to an individual patient, based on any number of clinically relevant parameters including, but not limited to toxicity, tolerance, side effects, effectiveness, etc.

EXAMPLES

Nonclinical studies performed to date reveal that DMB has significant biological activity and an encouraging nonclinical safety profile. The concentration-dependent increases in fetal globin expression, erythropoiesis, and F-cell production (which are readily achievable at 50 to 200 μg/mL of DMB) in human erythroid progenitor cultures suggest that this compound may promote significant therapeutic benefit in patients with hemoglobinopathies.

To date, DMB has been evaluated in 55 healthy human subjects in two phase 1 clinical trials. In addition, DMB has been evaluated in 21 patients with thalassemia intermedia and 25 patients with sickle cell disease in two phase 2 clinical trials. Furthermore, DMB was evaluated in several non-clinical studies for safety and efficacy.

Some properties of DMB and exemplary formulations are shown in Table 1.

TABLE 1

Pharmaceutical properties and formulation

| | |
|---|---|
| Drug Name | Sodium 2,2-dimethylbutyrate (DMB) |
| Chemical Name | Sodium 2,2-dimethylbutyrate |
| Chemical Class | Short-chain carboxylic acid |
| CAS Registry Number | CAS number for the sodium salt 3934-02-9 |
| | CAS number for the carboxylic acid is 595-37-9 |
| Chemical Structure | 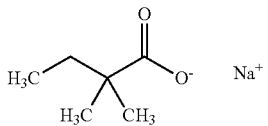 |
| Physical Appearance | 2,2, dimethylbutyric acid, sodium salt White crystalline solid |
| Molecular Formula | $C_6H_{11}NaO_2$ |
| Molecular Weight | 138.07 AU (Sodium 2,2-dimethylbutyrate) |
| | 116.15 AU (2,2-Dimethylbutyric acid) |
| Melting Point | >400° C. |
| Solubility | >500 mg/mL in water |
| Formulations | Capsules |
| Proposed Route of Administration | Oral |
| Storage and Handling | Room temperature |

Example 1

Non-Clinical Pharmacology

Multiple in vitro and in vivo nonclinical studies have been conducted to evaluate the primary pharmacodynamics of DMB. The in vitro studies examined the level of fetal globin induction relative to total globin. In vivo studies examined fetal globin induction as well as stimulation of erythropoiesis and hemoglobin levels, and were conducted in normal mice, transgenic mice containing the beta globin human gene locus and in anemic baboons.

Fetal Globin Expression In Vitro

DMB was compared to arginine butyrate (AB) for its ability to induce γ-globin expression in a double-luciferase reporter assay in murine erythroleukemia (GM979) cells transfected with the pLCR linked to the β- and γ-globin gene promoters linked to a different luciferase gene. The results were compared statistically to controls as shown in Table 2.

TABLE 2

Induction of Luciferase Activity

| Compound | Active Concentration (mM) | γ/(γ + β) globin Expression, Range | Mean Fold Increase |
|---|---|---|---|
| Control, Untreated | 0 | 0.015-0.022 | Baseline |
| Arginine butyrate | 0.5 | 0.029-0.047 | 1.8* |
| DMB | 0.5 | 0.033-0.052 | 2.2* |

*p ≤ 0.01; AB or DMB compared to untreated controls.

Fetal Globin Induction and Erythroid Cell Production in Transgenic Mice

Transgenic mice containing the human β globin gene locus in a yeast artificial chromosome (βYAC) displaying the correct developmental regulation of ε-, γ-, and β-globin genes (with a silenced y-globin gene in the adult stage) were used to study the effects of DMB on γ-globin induction and erythroid cell production. In the μLCR-human A γ-globin transgenic mice, the y-globin mRNA expression relative to murine α-globin mRNA was increased by a mean of 1.8-fold above the baseline after treatment with DMB. In the βYAC transgenic mice at intraperitoneal (IP) doses of 500 mg/kg/day, DMB induced a 2-fold increase in human γ-globin mRNA synthesis relative to that of total non-α-globin. This level of induction was similar to that seen with 1,000 mg/kg/day of butyrate, and the changes were observed from 3 days after treatment initiation and persisted until 3 to 5 days after treatment termination.

When administered at 500 mg/kg/day, DMB treatment increased reticulocyte counts approximately 6.7-fold. Reticulocytosis was observed from day 3 up to day 12 (at the end of sampling).

Fetal Globin Induction and Erythroid Cell Production in Anemic Baboons

Expression of γ-globin and erythroid cell production was evaluated in a primate model in which baboons are phlebotomized on a daily basis to simulate the chronic RBC destruction associated with hemoglobinopathies. In this model, baboons, aged 2 to 3 years, had 2.5 to 7 mL/kg of blood withdrawn daily, and the volume replaced with an identical volume of normal saline. Hemoglobin levels were lowered relative to control levels, but were maintained between 6.5 to 7.5 g/dL, the level necessary for the modulation of globin genes in this animal species. The animals were supplemented with iron dextran and folic acid. The phlebotomy regimen effectively exchanged the animals' total blood volume every 10 to 20 days.

Globin chain protein synthesis was measured in DMB treated animals using $^3$H-leucine-labeled reticulocytes before and 2 and 4 days after treatment. Complete blood counts and reticulocyte counts were monitored 3 times per week and plasma concentrations of the test article was determined. DMB was administered intravenously (IV, daily) or orally via nasogastric gavage under light anesthesia (on 3 alternating days per week for up to 6 weeks), on a dose-escalation schedule with starting doses of 500 to 800 mg/kg. If γ globin induction was observed, lower doses (40-200 mg/kg) were tested. Recombinant human erythropoietin (rhu-EPO) was also administered in separate treatment courses to 2 baboons at doses of 300 U/kg three times per week subcutaneously as a positive control for the erythropoietic effects of DMB. Treatments were performed in individual baboons.

Induction of γ globin chain expression was evaluated by measuring γ globin protein synthesis. An increase over the untreated, phlebotomized baseline was observed in each of 3 animals treated with DMB (see Table 3).

TABLE 3

Increase in γ-Globin Chain Protein Synthesis in Anemic Baboons

| | % γ Globin Chain Synthesis | | Increase | |
|---|---|---|---|---|
| DMB Treatment | Baseline | Treatment | % γ Globin Chain Synthesis | Fold |
| Mean of three animals | 3.4 | 10.0 | 6.6 | 2.9 |

In the anemic baboon model, increases in F-reticulocytes were usually observed within 2-3 days of treatment initiation and diminished within 3 to 5 days of treatment cessation.

When administered daily (IV) or on alternate days (orally), DMB treatment resulted in 3.8- to 15-fold increases in F-reticulocytes (see Table 4).

TABLE 4

Induction of F-Reticulocyte Production in Anemic Baboons

| Compound | Dosage | Method of Administration | Mean Fold Increase |
|---|---|---|---|
| DMB | 150 mg/kg/day | IV, 5 days | 5 |
| DMB | 200 mg/kg/day | IV, 5 days/wk | 15 |
| DMB | 500-700 mg/kg/$2^{nd}$ day | Oral | 3.8 |
| DMB | 500 mg/kg/$2^{nd}$ day | Oral, 5 days/wk, 2 wks | 3.8 |

The requirement for large daily phlebotomy as used in this regimen to induce fetal globin induction in baboons, which effectively exchanges the animal's total blood volume every 10 to 20 days, generally does not result in the accumulation of new Hgb. However, increases in RBCs were observed in several baboons after DMB administration. The increases in RBCs were first recognized after phlebotomy volumes were increased to maintain Hgb levels in the 6.5 to 7.5 g/dL range. This erythropoietic effect was evaluated by maintaining a stable daily phlebotomy volume, regardless of increases in Hgb or hematocrit (Hct) levels, and comparing the effects of rhu-EPO and DMB on these parameters.

Example 2

Non-Clinical Safety Pharmacology

Cardiac Repolarization Studies In Vitro and in Beagle Dogs

Cardiovascular safety pharmacology assessments included an in vitro screen to evaluate the effects of DMB on cardiac ion channel and an in vivo evaluation of cardiovascular and hemodynamic effects in Beagle dogs. Electrophysiologic effects were evaluated in laboratory studies utilizing voltage-clamped human embryonic kidney cells transformed by adenovirus cDNA and transfected with cDNA in order to stably express the human ether a-go-go related gene (hERG). The effect on cellular hERG channels was evaluated at DMB concentrations up to 1 mM (138 µg/mL). These findings support the conclusion that DMB has essentially no activity on hERG channel function.

No effects on systemic hemodynamics were observed in a 28-Day Beagle dog study. However, at the highest dose of 500 mg/kg/day, in a finding that was not statistically different from baseline (p>0.05), electrocardiographic (ECG) interval measurements of the QT interval corrected for heart rate (QTc) were prolonged on average by 14% in only female Beagle dogs. A causal association between QTc prolongation and DMB administration is considered unlikely due to the hERG channel study described above, the lack of a dose response effect, and due to its occurrence in only a single gender of the Beagle dogs tested. No biologically significant effects on ECG measurements were noted in the repeat dose 26-Week Beagle dog study described below (Example 5).

Central Nervous System Effects in Sprague Dawley Rats

DMB was administered orally to Sprague-Dawley rats (n=5/sex/group) for 14 consecutive days at doses of 200, 600 and 1,000 mg/kg and the effect of treatment on a functional observational battery (FOB) of behaviors was determined on Day 15. With respect to the FOB measurements, the effect of DMB appeared to be more pronounced in females than males. Both males and females in the 600 and 1,000 mg/kg/day groups were observed to have diminished body tone. However, decreased motor activity, reduced rectal temperature, direct limbic effects such as a deficit in visual tactile placing accuracy, ataxia, dragging of the hindlimbs in the open field, and decreased grip strength and neuromotor-neuromuscular deficits were only documented in the female rats at 600 mg/kg. In the male rats, these effects were present only in the animals treated with 1,000 mg/kg. Following a two-week drug free period, there were no residual FOB effects. As a result of these data, the no-observed adverse effect level (NOAEL) for central nervous system (CNS) effects was determined to be 200 mg/kg/day in female and 600 mg/kg/day in male Sprague Dawley rats.

Example 3

Pharmacokinetics and Metabolism in Baboons

Pharmacokinetics analyses have been conducted with DMB and 2,2-dimethylbutyric acid neutralized with L-arginine in baboons, dogs, and rats. The AUC per dose varied between animals. The median half-life was 2.7 hours (range 1.2 to 7.9). Oral bioavailability over 24 hours was >60%, often >90%, and appeared similar for both DMB and 2,2-dimethylbutyric acid neutralized with L-arginine. Metabolism studies in rats showed that the compound is hydroxylated and glucuronidated; in baboons, only a glucuronidated metabolite was found.

Pharmacokinetic Evaluation of Single Doses to 5 Baboons at Doses from 33.3 mg/kg to 167 mg/kg Free Acid Pharmacokinetic analyses of 2,2-dimethylbutyrate was conducted as either the sodium salt or the L-arginine salt, via the oral or intravenous route, as single doses to 5 baboons at doses of 33.3, 83.3, 100, 125 or 167 mg/kg free acid.

The data collected on DMB in plasma allowed an assessment of pharmacokinetic parameters; however, since collection time points were not performed in some baboons during the terminal elimination phase, these determinations are preliminary. The AUC per dose varied between animals. The area under the plasma concentration time-curve ($AUC_{0-24\,hr}$) following oral administration of DMB at 83.3 or 125 mg/kg free acid (100 and 150 mg/kg with salt) ranged from 1962-9363 µmol·h/L (226-1077 µg·h/L). Clearance ranged from 0.05-0.42 L/kg and estimated volume of distribution at steady state (Vss) was <2 L×h/kg. The median half-life was 2.7 hours (range =1.2-7.9) in 5 baboons. Oral bioavailability of sodium DMB over 24 hours was greater than 60% at estimated therapeutic doses and was similar for both DMB as a sodium salt or DMB neutralized with L-arginine.

Pharmacokinetic Evaluation of a 50 mg/kg IV Dose and 100, 150, and 200 mg/kg Oral Doses in One Female Baboon.

Figure 4:
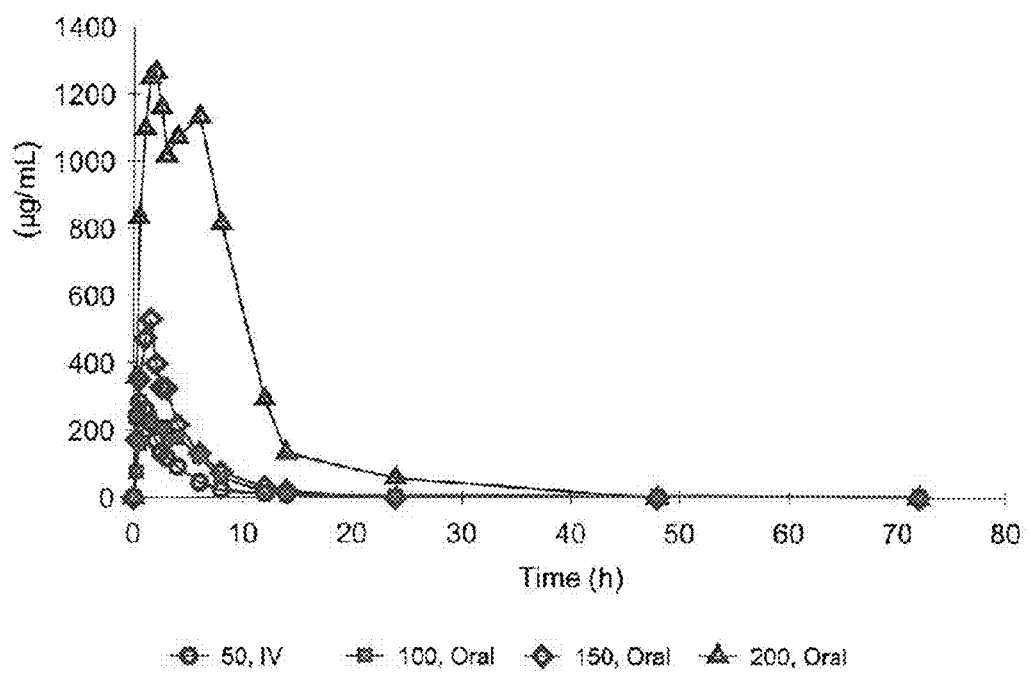
FIG. 4 is a graphic representation of plasma DMB versus time in a baboon following IV and Oral Dosing.

Additionally, the pharmacokinetic profile of DMB was evaluated in a female baboon who received an IV dose of 50 mg/kg and single oral doses of 100, 150 and 200 mg/kg. Following IV administration, DMB concentrations peaked at the end of dose administration and decayed in a log-linear fashion with no obvious appearance of a distribution phase and after oral administration, the concentration reached a peak within 2 hours after dosing and subsequently decayed in a log-linear fashion at all three dose levels. There was a secondary DMB peak which occurred at 6 hours after dosing of the 200 mg/kg oral dose (FIG. 4).

Following oral administration, the maximum concentration ($T_{MAX}$) values were observed at 1.5 to 2.0 hours after dosing, indicating rapid absorption of DMB, and the $C_{MAX}$ values increased somewhat greater than proportional to the administered dose. The estimated half-life values were variable, ranging from 2.89 to 6.92 hours, but did not appear to be dose-dependent. AUC values increased in proportion to dose between 100 and 150 mg/kg but increased over 5-fold as the dose was increased from 150 to 200 mg/kg. Apparent clearance (CL/F) values were similar for the 100 and 150 mg/kg doses but the CL/F for the 200 mg/kg dose was about $\frac{1}{4}^{th}$ that of the lower doses. These results suggest that DMB may display nonlinear pharmacokinetics, possibly by saturation of metabolism at the highest dose level. Vz/F was consistently smaller as the dose was increased. The absolute bioavailability, calculated from the IV and oral data at the 100 mg/kg dose, was high at 71.8% indicating the compound is readily absorbed by the oral route.

Inhibitory Potential on Human Hepatic Microsomal Cytochromes P450.

The inhibitory potential of DMB on the human cytochrome P450 activities involved in the metabolism of phenacetin O-deethylase (CYP1A2), bupropion hydroxylase (CYP2B6), amodiaquine N-deethylase (CYP2C8), diclofenac 4'-hydroxylase (CYP2C9), S-mephenyloin 4'-hydroxylase (CYP2C19), bufuralol 1'-hydroxylase (CYP2D6), testosterone 6β-hydroxylase (CYP3A), and midazolam 1'-hydroxylase (CYP3A) was assessed in vitro using human hepatic microsomes. Microsomes were incubated with isoenzyme-selective substrates at concentrations approximating the $K_m$ value in the absence and presence of DMB (at concentrations ranging from 0.1 to 300 04). The extent of inhibition was assessed by comparing activities from control and DMB-treated microsomes. DMB produced no significant inhibition of these cytochrome P450 activities. Percent activity remaining was high for all cytochrome P450 assays with 80% activity remaining compared with control activities. These data indicate that DMB at concentrations up to 300 μM is not a reversible-type inhibitor of the common human cytochromes P450.

Toxicology

Completed toxicology studies conducted with DMB include a single-dose toxicity study in Sprague-Dawley rats, escalating dose toxicity study in Beagle dogs, a repeat dose study of 14-Day duration in Sprague-Dawley rats and repeat-dose toxicity studies of 28-Day duration in Sprague-Dawley rats and Beagle dogs, and 26-Week studies in Sprague-Dawley rats and Beagle dogs. The 28-Day and 26-Week studies did not have a reversal group. Reproductive toxicity studies include two dose-range finding studies, one in Sprague-Dawley rats, the other in New Zealand white rabbits. DMB was administered once a day (QD) orally via gavage; doses are expressed as the sodium salt. In addition, an array of genotoxicity studies were conducted with DMB. A list of studies, including GLP status, is presented in Table 5 and Table 9. A list of dosages tested in longer-term treatment regimens and human equivalent dosages is provided in Table 6.

TABLE 5

DMB Toxicology Studies

| Study Type (GLP Status) | Route | Species/Strain | Dose Levels |
|---|---|---|---|
| Single Dose Toxicity Studies | | | |
| Dose Range-Finding Toxicity (non-GLP) | Oral gavage QD | Rat/Sprague-Dawley | 0, 100, 500 and 1,000 mg/kg/day |

TABLE 5-continued

DMB Toxicology Studies

| Study Type (GLP Status) | Route | Species/Strain | Dose Levels |
|---|---|---|---|
| Repeat-Dose Toxicity Studies | | | |
| 2-Week (15-day) repeat dose toxicity study with a two week drug free period (GLP) | Oral gavage QD | Rat/Sprague-Dawley | 0, 200, 600 and 1,000 mg/kg/day |
| 28-Day toxicity (GLP except for bioanalysis of DMB concentration in plasma) | Oral gavage QD | Rat/Sprague-Dawley | 0, 100, 500, 1,000 and 2,000/ 1,500[a] mg/kg/day |
| 26-Week repeat dose toxicity study (GLP) | Oral gavage QD | Rat/Sprague-Dawley | 0, 50, 100, and 500 mg/kg/day |
| 2-week escalating dose/MTD Toxicity (GLP) | Oral gavage QD | Dog/Beagle | 250-1,000 mg/kg and 500 mg/kg/day |
| 28-Day repeat dose toxicity study (GLP) | Oral gavage QD | Dog/Beagle | 0, 50, 150, and 500 mg/kg/day |
| 26-repeat dose toxicity study (GLP) | Oral Capsule QD | Dog/Beagle | 0, 50, 150, and 300 mg/kg/day |
| Reproductive Toxicity | | | |
| A Dose Range-Finding Study of the Effects of DMB on Embryo/Fetal Development in Rats (GLP) | Oral gavage QD | Rat/Sprague-Dawley | 0, 50, 150, 500 and 1,000 mg/kg/day |
| A Dose Range-Finding Study of the Effects of DMB on Embryo/Fetal Development in Rabbits (GLP) | Oral gavage QD | Rabbit/New Zealand White | 0, 50, 150, 300 and 600 mg/kg/day |

[a]High dose of 2,000 mg/kg/day lowered to 1,500 mg/kg/day on Day 5.
Abbreviations:
QD = once daily

TABLE 6

Dosage equivalents from Repeat Dose Studies

| Repeat Dose length and test subjects | Dose (mg/kg/d) | Dose[a] (mg/m²) | Human Equiv. Dose (mg/kg/day) |
|---|---|---|---|
| 14-Day Repeat Dose Rat Study (Sprague Dawley) | 200 | 1,200 | 32 |
| | 600 | 3.600 | 97 |
| | 1,000 | 6,000 | 162 |
| 28-Day Repeat Dose Rat Study (Sprague Dawley) | 100 | 600 | 16 |
| | 500 | 3,000 | 81 |
| | 1,000 | 6,000 | 162 |
| | 2,000/1,500 | 12,000/9,000 | 324/243 |
| 14-Day Dose Escalating and maximum tolerated dose dog study (Beagles) | 250 | 5,000 | 135 |
| | 500 | 10,000 | 270 |
| 28-Day Repeat Dose Dog Study (Beagles) | 150 | 3,000 | 81 |
| | 500 | 10,000 | 270 |

TABLE 6-continued

Dosage equivalents from Repeat Dose Studies

| Repeat Dose length and test subjects | Dose (mg/kg/d) | Dose[a] (mg/m²) | Human Equiv. Dose (mg/kg/day) |
|---|---|---|---|
| 26-Week Repeat Dose Rat Study (Sprague-Dawley) | 100 | 600 | 16 |
| | 500 | 3000 | 81 |
| 26-Week Repeat Dose Dog Study (Beagles) | 50 | 1000 | 27 |
| | 300 | 6000 | 162 |

[a]Body surface area doses (mg/m²) were derived by multiplying administered doses (mg/kg) ×6 for rats, ×20 for dogs, and ×37 for humans.

Example 4 and 5

26-Week Repeat Dose Studies in Sprague Dawley Rats and Beagle Dogs

The 26-Week studies in Sprague Dawley rats and Beagle dogs have been completed, with no adverse effects reported. The group of Beagle dogs treated with 300 mg/kg/day did have a slightly slower weight gain than control animals, though this was not considered an adverse finding. Clinical pathology findings included increases in RBC parameters and indices and select serum chemistries but were unremarkable except for slight elevations in alkaline phosphatase levels in Sprague Dawley rats at the highest dose level (500 mg/kg/day only). Histopathological assessment of tissues showed only mild biliary hyperplasia at the highest dose level (500 mg/kg) in Sprague Dawley rats. Beagle dogs showed no laboratory or pathological abnormalities at any dose level up to 300 mg/kg/day.

There were no test article-associated mortalities or clinical observations attributed to daily oral administration for 26 weeks of DMB in Sprague Dawley rats. Erythroid parameters (e.g., red blood cell count, hemoglobin (Hgb) and hematocrit (Hct)) and indices (e.g., mean corpuscular volume (MCV), mean corpuscular hemoglobin and mean corpuscular hemoglobin concentration (MCHC)), select serum chemistries (e.g., potassium concentration and alkaline phosphatase activity) and mean absolute and relative select organ weight (e.g., liver, heart and kidney) were observed in male and female Sprague Dawley rats treated at the 500 mg/kg/day dose level. Activated partial thromboplastin time (APTT) was significantly shorter in the 500 mg/kg/day male Sprague Dawley rats at the interim and terminal timepoints. Minimal bile duct hyperplasia was also observed in the 500 mg/kg/day Sprague Dawley rats in both males and females. There were no abnormal macroscopic or microscopic observations associated with the elevated kidney or brain weights. These treatment-related findings were not considered adverse. The NOAEL for DMB administered to Sprague-Dawley rats for a minimum of 181 days was considered to be 500 mg/kg/day, whereas the NOEL for female Sprague-Dawley rats was 100 mg/kg/day.

Following daily administration for 26 weeks of DMB to Beagle dogs, there were no important treatment-related clinical observations. Based on the results of this study, the NOEL for DMB in male and female Beagle dogs was 50 mg/kg/day; and the NOAEL for DMB in male and female Beagle dogs was at least 300 mg/kg/day, the highest dose administered over the 26-Week treatment period.

Central Nervous System Effects

The no-observed adverse effect level (NOAEL) for central nervous system (CNS) effects was determined to be 200 mg/kg/day in female rats and 600 mg/kg/day in male Sprague Dawley rats. In the 26-Week studies, Sprague Dawley rats and Beagle dogs showed no abnormalities in the central nervous system at dose levels up to 500 mg/kg and 300 mg/kg, respectively.

Hepatic Effects

In the 28-Day Sprague Dawley rat study, statistically significant, test article-related increases in mean absolute and relative liver weights were present in males at 1,000 mg/kg/day and in females at 1,000 mg/kg/day. Slight increases in serum enzymes included: alanine aminotransferase (ALT) in males at 1,000 mg/kg/day and in females at 2,000/1,500 mg/kg/day and aspartate aminotransferase (AST) in males at 1,000 mg/kg/day. There were no histologic correlates with these findings. In the 26-Week Sprague Dawley rat study, there were slight elevations in alkaline phosphatase levels and mild biliary hyperplasia, observed at the highest dose level (500 mg/kg/day) only, with associated increases in mean absolute and relative liver weights in females at this dose level. These changes in organ weight were not associated with abnormal pathology and not considered adverse. Beagle dogs showed no abnormalities at any dose levels up to 300 mg/kg/day following 26 weeks of once-daily dose administration.

Kidney Effects

In the 28-Day Sprague Dawley rat study, statistically significant, test article-related increases in mean absolute and relative kidney weights were seen in males at 500 and 1,000 mg/kg/day and in females at 1,000 mg/kg/day. Kidney weight was not increased in the single surviving 2,000/1,500 mg/kg/day male. No histological correlates were seen for these changes. Similar changes were noted in the two-week study, which reversed following cessation of treatment. In the 26-Week Sprague Dawley rat study, test article-related increases in mean absolute and relative kidney weights were seen in male and female Sprague Dawley rats at 500 mg/kg/day, and male Sprague Dawley rats at 100 mg/kg/day. There were no test article-related histomorphologic alterations consistent with the increase in absolute or relative kidney weights at either dose level. No abnormalities in laboratory studies or histology were observed in the 26-Week (6 month) study in Beagle dogs at any dose levels.

Pathology Changes.

Several clinical pathology changes occurred in the 28-Day Sprague Dawley rat study. At 2,000/1,500 mg/kg/day, decreased RBC, lymphocyte, and leukocyte counts were noted and considered suggestive of stress or immunosuppression. At ≥1,000 mg/kg/day, decreases in Hgb, Hct, MCV, and MCHC, were observed. Decreases in Hgb, Hct, and MCV were also seen in 500 mg/kg/day females. Activated partial thromboplastin time was decreased in males at ≥1,000 mg/kg/day and females at 2,000/1,500 mg/kg/day and prothrombin time was increased in males of both groups. Increases in blood urea nitrogen, albumin, albumin/globulin ratio, and inorganic phosphorus and decreases in cholesterol and globulin were seen at ≥1,000 mg/kg/day. These serum chemistry changes were associated with the decreases seen in body weights and food consumption in these groups. In addition, slight increases in serum enzymes included: ALT in males at ≥1,000 mg/kg/day and in females at 2,000/1,500 mg/kg/day and AST in males at ≥1,000 mg/kg/day. No abnormalities other than mild biliary hyperplasia in Sprague Dawley rats treated at the highest dose level (500 mg/kg/day) were observed in Sprague Dawley rats or Beagle dogs in the 26-Week (6 month) studies.

Example 6

Toxicokinetics

Overall, exposure to DMB increased with increasing dose in both Sprague Dawley rats and Beagle dogs. Beagle dogs showed some gender difference in exposure, with females having higher and longer-lasting plasma levels of DMB. The data from these studies shown in FIG. 5 suggest that predictive toxicological effects occur only when serum levels exceed 500 mg/mL.

Toxicokinetics in Sprague Dawley Rats.

Figure 6:
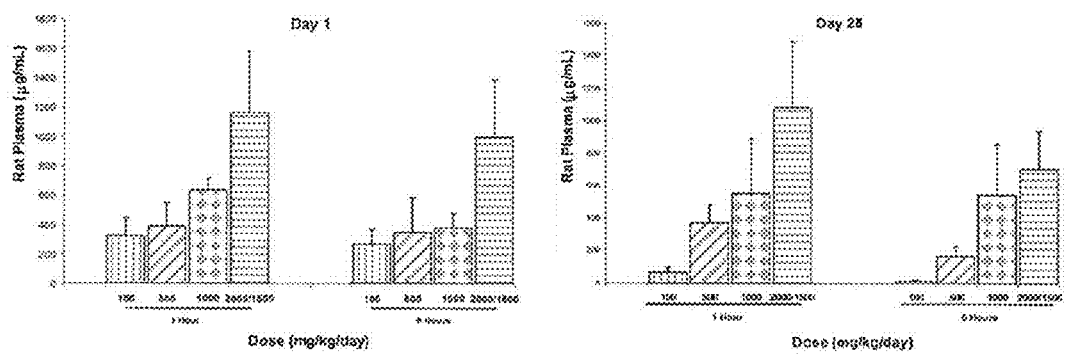
FIG. 6 is a graphic representation of the relationship of DMB plasma levels in Sprague Dawley rats to dose and duration in repeat dose toxicity studies.

DMB was administered to Sprague Dawley rats daily for 4 weeks at doses ranging from 100 to 2,000/1,500 mg/kg/day via oral gavage. Plasma levels were measured at 1 and 6 hours post-dose on Days 1 and 28. Means and standard deviations for these values are shown in FIG. 6. Gender-related differences were not observed. DMB concentrations increased with increasing dose on both Day 1 and Day 28.

DMB was administered to Sprague Dawley rats daily for 26 weeks at doses of 50, 100 and 500 mg/kg/day via oral gavage. Plasma levels of DMB were measured at 1 to 24 hours post-dose on Days 1 and 181. Peak plasma concentrations were noted at 1 hour postdose on Day 0, and at 1 to 4 hours postdose on Day 181. Systemic exposure increased with increasing dose level and was greater than dose-proportional on Day 0 and Day 181. The peak and extent of systemic exposure of Sprague Dawley rats to DMB were similar in males and females. Systemic exposure values on Day 181 ranged from 137% to 218% of the values at Day 0 indicating an accumulation of DMB during this time period.

Toxicokinetics in Beagle Dogs.

Figure 5:
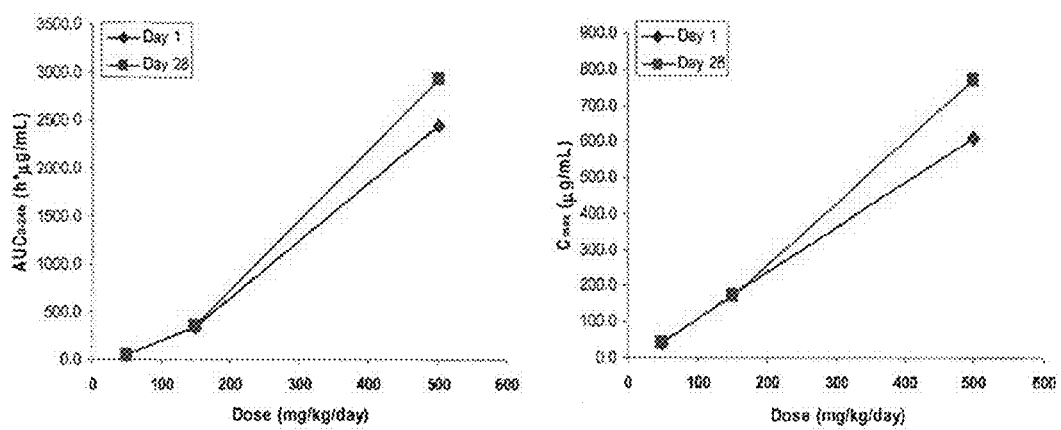
FIG. 5 is a graphic representation of the relationship of DMB exposure in Beagle dogs (AUC and $C_{max}$) to dose in repeat dose toxicity studies.

DMB was administered to Beagle dogs daily for 4 weeks at doses of 50, 150 and 500 mg/kg/day vial oral gavage. Plasma levels were measured using a validated assay at 0.5 to 24 hours post-dose on Days 1 and 28 (FIG. 5). Plasma levels appeared to increase with increasing dose but did not change with repeated dosing. No significant gender differences in exposure were seen.

DMB was administered orally by capsule to Beagle dogs for 26 weeks at dose levels of 0, 50, 150 and 300 mg/kg/day. Plasma levels were measured at 1 to 24 hours post-dose on Days 1 and 181. Peak plasma concentrations were measured at 1 to 4 hour postdose on Day 0, and at 1 to 8 hours postdose during Week 26. Systemic exposure increased with increasing dose level and was greater than dose-proportional on Day 0 and Week 26. For a 6-fold increase in dose level from 50 to 300 mg/kg/day, there was a 12.85-fold increase in exposure values for males and a 10.31-fold increase for females on Day 0. On Week 26, there was an 8.35-fold increase in exposure values for males and a 7.58-fold increase for females. The peak and extent of systemic exposure of Beagle dogs to DMB were similar in males and females. Systemic exposure values at Week 26 were 138 to 153% of the values at Day 0 for 50 mg/kg, 130% for 150 mg/kg, and 100 to 102% 300 mg/kg dose levels, indicating an accumulation of DMB during this time period for the 50 and 150 mg/kg dose levels and no accumulation at the 300 mg/kg dose level.

Comparison of Exposure in 26-Week Non-Clinical Studies with Human Dose Levels Chosen for Phase I Trials.

Toxicokinetic information from the 26-week rat (Table 7) and 26-week dog toxicity studies (Table 8) are compared to systemic exposure (AUC) levels determined in a clinical study.

TABLE 7

Exposure Tables for 26-Week Sprague Dawley Rat Studies and Human Doses

| | | Human Dose Levels/$AUC_{0-\infty}$ values | | | |
|---|---|---|---|---|---|
| | | 2 mg/kg | 5 mg/kg | 10 mg/kg | 20 mg/kg |
| Sprague Dawley Rat Dose Levels[1] | $AUC_{0-\infty}$ (μg * h/mL) | 38 ± 23 | 320 ± 40 | 538 ± 125 | 1190 ± 243 |
| 50 mg/kg | 125 | 3.2X | 0.4X | 0.2X | 0.1X |
| 100 mg/kg | 278 | 7.3X | 0.9X | 0.5X | 0.2X |
| 500 mg/kg (NOAEL) | 3439 | 91X | 10.7X | 6.4X | 2.9X |

[1]Mean for both male and female rats at each dose level

TABLE 8

Exposure Tables for 26-Week Beagle Dog Studies and Human Doses

| | | Human Dose Levels/$AUC_{0-\infty}$ values | | | |
|---|---|---|---|---|---|
| | | 2 mg/kg | 5 mg/kg | 10 mg/kg | 20 mg/kg |
| Beagle Dog Dose Levels[1] | $AUC_{0-\infty}$ (μg * h/mL) | 38 ± 23 | 320 ± 40 | 538 ± 125 | 1190 ± 243 |
| 50 mg/kg | 127 | 3.3X | 0.4X | 0.2X | 0.1X |
| 150 mg/kg | 473 | 12.4X | 1.5X | 0.9X | 0.4X |
| 300 mg/kg (NOAEL) | 1466 | 38.6X | 4.6X | 2.7X | 1.2X |

[1]Mean for both male and female Beagle dogs at each dose level

The NOAEL, or "no observable adverse effect level" represents treatment related effects that were seen during the study but not considered adverse due to low severity, lack of biological significance, reversibility, or lack of a clear dose response. The NOAEL doses in dogs and rats represent drug concentrations that are 1.2 and 2.9 times the 20 mg/kg dose evaluated in human subjects after allometric scaling.

Example 7

Reproductive Toxicity

A dose range finding developmental toxicity study has been completed in both Sprague Dawley rats and New Zealand White rabbits to determine appropriate dosage levels of DMB for a definitive embryo/fetal developmental toxicity study in these species.

Reproductive Toxicity in Sprague Dawley Rats.

DMB was administered orally by gavage to 4 groups of 8 bred female Sprague Dawley rats once daily from gestation Days 6 through 17, at dosage levels of 50, 150, 500 and 1000 mg/kg/day. A concurrent control group composed of 8 females received the vehicle (deionized water) on a comparable regimen. On gestation Day 20, a laparohysterectomy was performed on each surviving female. There was no evidence of maternal toxicity in the 50 and 150 mg/kg/day groups. Dosages of 500 mg/kg/day were considered unacceptable for a definitive embryo/fetal developmental toxicity study in based on maternal toxicity (moribundity, clinical signs, reduced mean body weight gains or body weights losses and decreased food consumption) and embryo/fetal toxicity, including postimplantation loss and/or lower fetal weights. Increased postimplantation loss was noted at 150 mg/kg/day with a corresponding lower proportion of viable fetuses per litter. No maternal or fetal effects were observed at the 50 mg/kg/day dosage level.

Reproductive Toxicity in New Zealand White Rabbits.

DMB was administered orally by gavage to 4 groups of 8 time-mated female New Zealand White rabbits once daily from gestation Days 7 through 20 at dosage levels of 50, 150, 300 and 600 mg/kg/day. A concurrent control group composed of 8 time-mated females received only the vehicle on a comparable regimen. No remarkable maternal macroscopic findings were noted at any dosage level. All findings at necropsy occurred sporadically in single females, with similar frequencies in the control group and/or in a non dose-related manner and were considered incidental and unrelated to administration of DMB. Mean fetal weight in the 600 mg/kg/day group was 8.6% lower than the control group. Fetal weights in the 50, 150 and 300 mg/kg/day groups and fetal survival and external morphology at all dosage levels were unaffected by test article administration. Dosages of 600 mg/kg/day were considered unacceptable for a definitive embryo/fetal development study based on maternal toxicity (moribundity/abortion, mean maternal body weight losses and corresponding reduced mean food consumption) and embryo/fetal toxicity (reduced fetal weights). Reduced mean maternal body weight gains and corresponding reduced mean food consumption were noted at 300 mg/kg/day. There were no maternal or fetal test article-related effects observed at the 50 and 150 mg/kg/day dosage levels.

Example 8

Genotoxicity

A significantly increased number of micronucleated cells after DMB exposure was documented only with male Sprague Dawley rats given 1,000 mg/kg of DMB for 14 days. This effect was not observed in female Sprague Dawley rats, and the number of micronucleated cells noted was within the historical untreated control values, and well below the numbers seen with historical positive controls such as cyclophosphamide. Further analyses demonstrated that this activity occurred only in the presence of plasma levels of DMB exceeding 500 µg/mL, a level several fold higher than the levels that are expected with the doses being tested in ongoing and planned clinical trials. Based on the weight of evidence that includes negative results in the bacterial mutagenicity (Ames assay) and chromosomal aberrations in human peripheral lymphocytes, and results in the micronucleus that indicate a weak response that is of questionable biological significance, DMB demonstrates limited potential to cause genotoxicity.

DMB dosages used for genotoxicity studies are shown in Table 9 and detailed findings follow below.

TABLE 9

DMB Genotoxicity Studies
Genotoxicity

| | | | |
|---|---|---|---|
| Ames Assay (GLP) | In vitro | Bacteria/*E. coli* (1 strain) and *S. typhimurium* (4 strains) | 100, 333, 1,000, 3,330 and 5,000 µg/plate (with and without S9) |

TABLE 9-continued

DMB Genotoxicity Studies
Genotoxicity

| | | | |
|---|---|---|---|
| Chromosomal aberration (GLP) | In vitro | Human Peripheral Blood Lymphocytes | 3 hours without S9: 2,450, 3,500 and 5,000 µg/mL. 3 hours with S9: 2,450, 3,500 and 5,000 µg/mL. 22 hours without S9: 288, 412 and 588 µg/mL. |
| Rat Micronucleus Assay (GLP) | In vivo | Rat/Sprague-Dawley | 0, 200, 600, 1,000 mg/kg/day: 14 days |

In Vitro Genetic Toxicity Tests

The standard battery of in vitro genetic toxicity tests were conducted with DMB. These tests were conducted with positive and vehicle controls, with and without metabolic activation, as appropriate, and in accordance with accepted guidelines.

For the Ames (reverse bacterial mutagenicity test), the tester strains used in the mutagenicity assay were *S. typhimurium* tester strains TA98, TA100, TA1535, and TA1537 and *E. coli* tester strain WP2uvrA. The assay was conducted in both the presence and absence of S9 mix along with concurrent vehicle and positive controls using three plates per dose. The doses tested in the mutagenicity assays in both the presence and absence of S9 mix were 100, 333, 1000, 3330, and 5000 mg/plate. No increase in mutation counts was seen at any concentration and no cytotoxicity was observed, as indicated by normal background lawn growth.

DMB was examined for the potential to induce chromosome aberrations in human peripheral lymphocytes in the presence and absence of an exogenous metabolic activation system (S9 mix). In the 3-hour cultures (without or with activation), the highest three concentrations (2450, 3500, and 5000 µg/mL) were analyzed for chromosome aberrations. In the 22-hour treatment, 288, 412 and 588 µg/ML were analyzed for chromosome aberrations. There were no test article-related increases in the number of structural aberrations per cell, the percent of cells with structural aberrations, or the percent of cells with greater than one structural aberration, when compared to vehicle-treated cultures.

No test article-related increase in numerical aberrations (polyploidy or endoreduplication) was observed in any of the cultures. The aberrations in control cultures were within historical ranges. DMB was therefore considered negative for inducing structural or numerical chromosome aberrations in human peripheral lymphocytes with and without metabolic activation.

In Vivo Genetic Toxicity Tests

The potential for DMB to induce formation of micronuclei in vivo was evaluated as part of the initial 14-Day toxicity repeat dose toxicity study in rats administered doses of 0, 200, 600 and 1,000 mg/kg/day for 14 days. A statistically significant increase in the frequency of micronucleated erythrocytes (PCEs) compared to controls was observed in male rats, but the effect was noted only in the highest dose group, overlapped with results observed in the female vehicle controls, and was not as high as observed in historical studies with positive control (cyclophosphamide). This effect was confirmed in the regression trend test ($p<0.05$). This result was not observed in any of the female groups or in the two male groups given lower daily doses of DMB. There was no effect on the percent PCEs in either male or female rats at any dose level.

Although the increase (mean—3.3±0.16 MN PCEs/1,000 PCEs) is statistically significant, it is considered to lack biological significance as a predictor of chromosomal damage or mutagenicity for the following reasons: 1) both in vitro tests (Ames and chromosome aberration assay) showed negative genotoxic potential; 2) the increase was observed in only males exposed to the highest dose: (1,000 mg/kg/day); 3) the increase is within the range of historical negative control values: (0 to 3.5 MN PCEs/1,000 PCEs, mean±SD–1.0±0.9 MN); 4) The increase is close to the female vehicle control value (3.0±11.2 MN PCEs/1,000 PCEs); 5) the increase is far below the range of historical positive control (cyclophosphamide) values: (9 to 27 MN PCEs/1,000 PCEs, mean±SD—19.2±15.5 MN PCEs/1,000 PCEs), and; 6) females appeared to be severely affected by test article induced toxicity, yet showed no effect on micronucleated PCEs.

Example 9

Immunotoxicology

The immunotoxicological potential of DMB has been evaluated by a weight-of-evidence analysis of the data generated in the repeat dose Sprague Dawley rat and Beagle dog studies. In both studies, there were no effects of treatment on WBC levels or lymph node histopathology, which are predictive of potential immunotoxicity. The lack of effect of DMB on these measures suggest that the drug has a low potential for toxicity to the immune system.

Clinical Studies

The selection of the starting dose for the healthy human subject clinical studies was based on the data obtained from the 28-Day repeat dose toxicology studies. Based on these data, the NOAEL in the most sensitive gender/species (the female Sprague Dawley rat) was 200 mg/kg/day, which is equivalent to a human dose (HED) of 32 mg/kg. The conservative starting dose chosen for the first-in-human studies (2 mg/kg/day) were less than $1/15^{th}$ of the HED, which is consistent with current regulatory guidance.

To date, DMB has been evaluated in 55 healthy human subjects in 2 clinical trials. In the first study, 24 subjects were treated with single doses of DMB at dose levels ranging from 2 to 20 mg/kg. This study was completed with no significant AEs noted and revealed that biologically active plasma drug levels (as established in prior in vitro studies performed with whole blood from patients with T1) could be achieved with doses at or above 10 mg/kg. Additional findings from this study are described below. In a second study, a total of 41 healthy human subjects have been treated for 14 consecutive days of DMB (n=31) at dose levels of 5, 10 and 15 mg/kg or placebo (n=10). All subjects have completed dosing with safety, clinical and laboratory data available from all subjects. No SAEs and no significant treatment related AEs have been observed, as described in more detail below.

In addition, DMB has been evaluated in 21 patients with thalassemia intermedia at repeat doses of 10 mg/kg, 20 mg/kg, 30 mg/kg, and 40 mg/kg over 8 weeks, and 25 patients with sickle cell disease at repeat doses of 10 mg/kg, 20 mg/kg, and 30 mg/kg over 6 weeks.

Example 10

Phase 1 Single Dose Clinical Study

The first clinical study was a phase 1, double-blind, placebo-controlled, single dose study of the tolerability, safety and pharmacokinetics of DMB in 32 healthy volunteers. Healthy, fasting adult volunteers received single oral doses of DMB or placebo capsules at one of four dose levels (2 mg/kg, 5 mg/kg, 10 mg/kg and 20 mg/kg). Six subjects received study drug (24 subjects total) and 2 subjects received placebo at each dose level. The 8 placebo subjects received a capsule containing only the excipients from the capsules containing the active agent. Subjects at the 20 mg/kg also received a second dose of study drug after a defined meal, one week following the fasting dose.

Safety Observations

Physical examinations, vital signs and neurologic examinations were normal throughout the study. No signs or symptoms of clinical significance were observed. One subject developed transient mild hypotension after dosing, which was clinically asymptomatic, and the Principal Investigator considered this finding to be of no clinical significance. Postural changes in blood pressure and pulse were not evaluated. There were 3 electrocardiogram abnormalities among patients treated with active study medication and 3 among the placebo subjects, all of which were considered to be of no clinical significance. All laboratory studies, including chemistries, coagulation studies, hematology studies and urinalyses were either normal or of no clinical significance except for one subject in whom a urinary tract infection was diagnosed but not disclosed prior to study test article administration. Table 10 below lists all of the AEs observed, presented by cohort. The data are reported for each cohort including the N of subjects that received placebo or study drug. All events were assessed as mild by the Principal Investigator. The reported AEs are shown by Cohort following Table 10. The only AEs considered possibly or probably related to study medication included upper abdominal pain, which occurred in one subject in the 2 mg/kg treatment group, one subject with dizziness in the placebo treatment group, and one subject with dysphoria in the 10 mg/kg treatment group. No subjects discontinued treatment due to AEs and there were no SAEs reported in this study.

TABLE 10

Subject Incidence of AEs by Descending Frequency
Summary of Adverse Events

| List of Adverse Events | Placebo N = 8 (%) | DMB N = 24 (%) |
|---|---|---|
| Headache | 25 | 29 |
| Vessel puncture site hematoma | 13 | 17 |
| Dizziness | 25 | 13 |
| Nausea | 13 | 8 |
| URI | 13 | 8 |
| Diarrhea | | 8 |
| Cough | 25 | 4 |
| Abdominal pain, upper | | 4 |
| Abdominal tenderness | | 4 |
| Dysguesia | | 4 |
| Dysphoria | | 4 |
| Ecchymosis | | 4 |
| Epistaxis | | 4 |
| Fatigue | | 4 |
| Insomnia | | 4 |
| Myalgia | | 4 |
| Odynophagia | | 4 |
| Palpitations | | 4 |
| Syncope vasovagal | | 4 |
| Anxiety | 13 | |
| Dysmenorrhea | 13 | |
| Injection | 13 | |
| Menorrhagia | 13 | |
| Pain in extremity | 13 | |
| Pharyngitis | 13 | |

TABLE 10-continued

Subject Incidence of AEs by Descending Frequency
Summary of Adverse Events

| List of Adverse Events | Placebo<br>N = 8<br>(%) | DMB<br>N = 24<br>(%) |
|---|---|---|
| Pharyngolaryngeal pain | | 13 |
| Sialoadenitis | | 13 |

N = number of subjects in each treatment group,
% = percentage of subjects who experienced an AE Coded using preferred terms from MeDRA v10.
Subjects with multiple events coding to one preferred term, were only counted once.

Pharmacokinetic Observations

Figure 7:
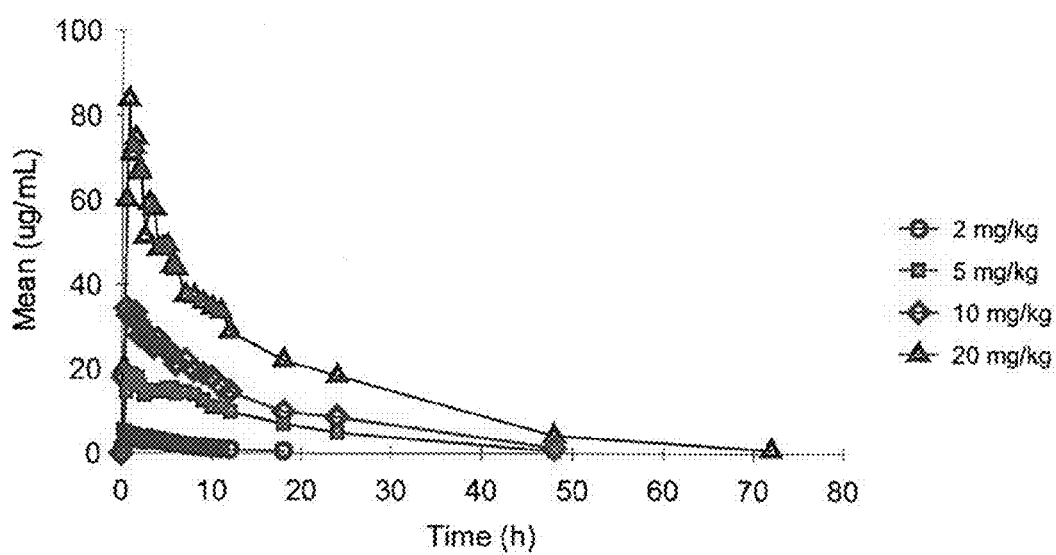
FIG. 7 is a graphic representation of plasma DMB concentration versus time in healthy human subjects treated with a single dose of DMB.
Figure 8:
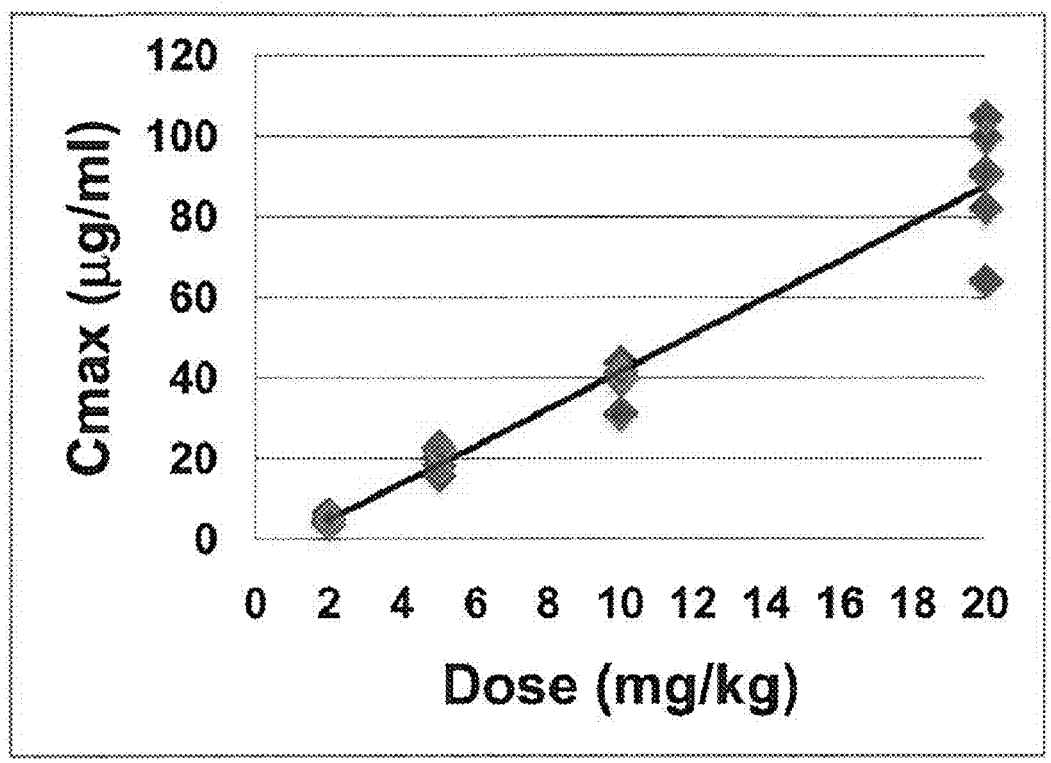
FIG. 8 is a graphic representation of the relationship of $C_{max}$ to DMB dose level in healthy human subjects treated with a single dose of DMB.
Figure 9:
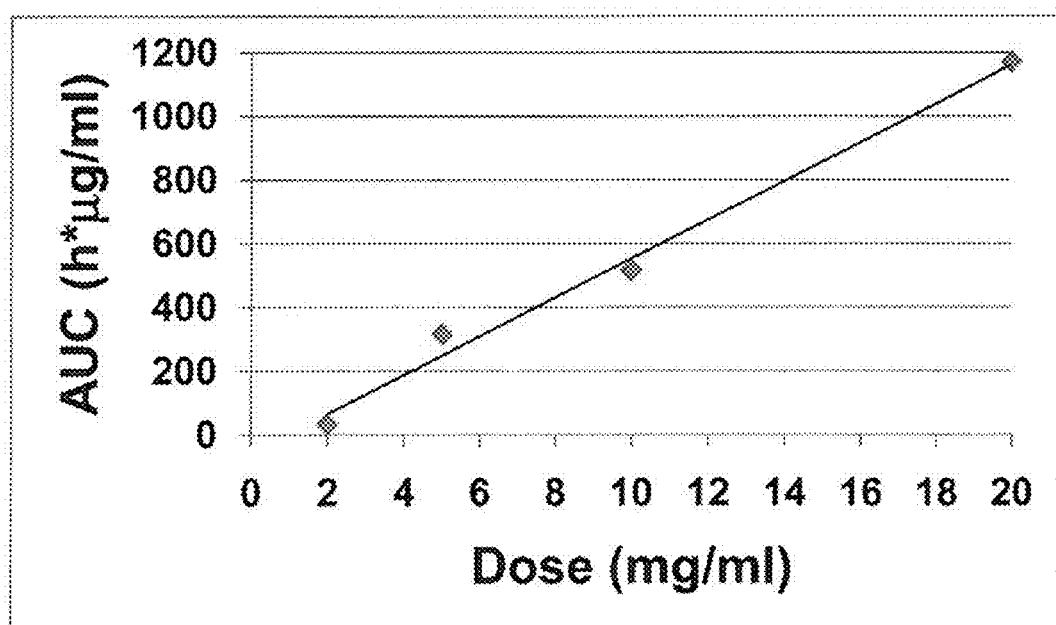
FIG. 9 is a graphic representation of the relationship of AUC to DMB dose level in healthy human subjects treated with a single dose of DMB.

DMB was rapidly absorbed after oral administration, with peak concentrations of DMB occurring at 0.5 to 3 hours after dosing, followed by a mono-exponential decay phase, consistent with linear pharmacokinetics (FIG. 7; FIG. 8). Inter-subject variability in the primary PK parameters appears to be low, especially at higher doses. Compared to fasting conditions, administration of DMB under fed conditions (tested at the 20 mg/kg dose level) resulted in a delay in the rate of drug absorption, but not the overall amount of absorption. The average half-life ranged from 5.5 to 11.6 hours and increased with increases in the administered dose. AUC values increased with the increase in dose administered, ranging from an average of 38.3 h·µg/mL at the 5 mg/kg dose to 1190 h·µg/mL at the 20 mg/kg dose (FIG. 9).

The relatively small volume of distribution 0.204 to 0.426 L/kg suggests that the distribution of DMB is less than total body water, and thus not widely distributed throughout the body. The CL/F values were low, ranging from 0.016 to 0.062 L/b/kg, and with the exception of the low dose, appeared to be independent of the dose administered, suggesting that DMB displays linear pharmacokinetics over the 10 to 20 mg/kg dose range.

Figure 10:
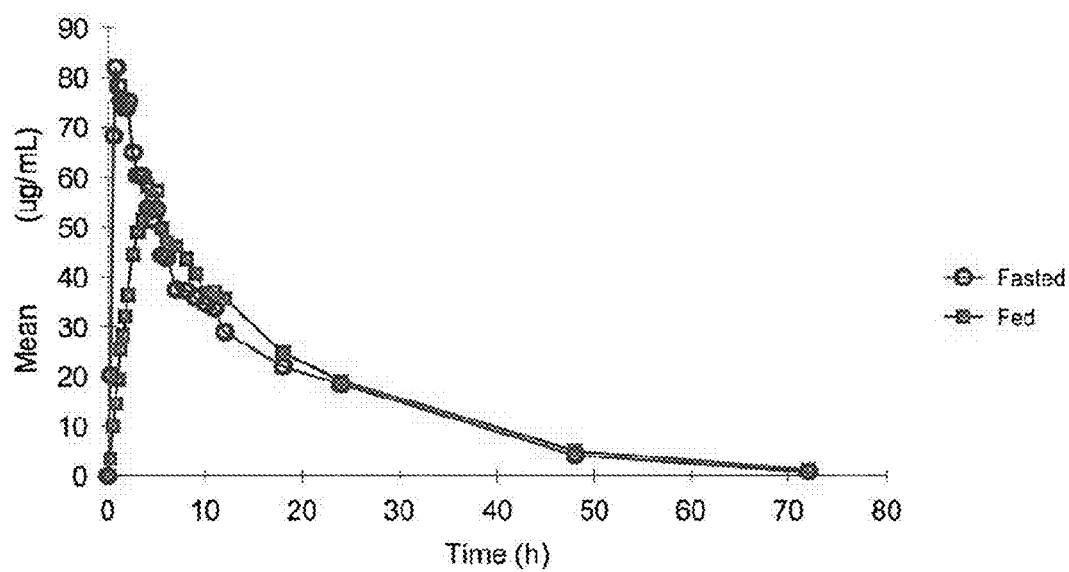
FIG. 10 is a graphic representation of the mean plasma DMB concentration versus time for fasted and fed treatments in healthy human subjects treated with a single dose of DMB.

Subjects treated in Cohort 4 received DMB under both fed and fasted conditions. The presence of food resulted in a delay in the $T_{max}$ and decrease in the mean $C_{max}$ from 89 to 60 µg/mL. However, no effects were observed on the AUCINF, indicating that administration of DMB with a meal may result in a delay or decrease in the rate of absorption, but not in the extent of absorption. This is illustrated in FIG. 10.

Example 11

Phase 1 Repeat-Dose Clinical Study

DMB was evaluated in a phase 1, placebo-controlled, randomized, repeat dose clinical study that evaluated tolerability, safety, and pharmacokinetics in healthy volunteers. A total of 41 subjects (31 receiving active drug and 10 receiving placebo) completed 14 consecutive days of study medication at daily dose levels of 5, 10 or 15 mg/kg (10 subjects received placebo). Given the importance of iron in red blood cell production, and the requirement for iron supplementation for induction of HbF with other erythropoietic agents, subjects at all 3 dose levels received oral ferrous gluconate on the study medication days. DMB was administered with food to all but one group (5 mg/kg, cohort 1). Subjects were admitted and observed for 24 hours following initial dosing. Thereafter, the study drug was taken once per day at home, except for the last study day. The subjects were monitored weekly for 6 weeks. Thirty-seven subjects completed the study and 4 subjects dropped out due to conflicts. Safety and PK data are available on these subjects.

The treatment groups included: Cohort 1: 5 mg/kg fasting, 6 active, 2 placebo; Cohort 2: 5 mg/kg with food, 7 active, 2 placebo (3 drop outs); Cohort 3: 5 mg/kg with food and iron supplements, 6 active, 2 placebo (1 drop out); Cohort 4: 10 mg/kg with food and iron supplements, 6 active, 2 placebo; and Cohort 5: 15 mg/kg with food and iron supplements, 6 active, 2 placebo. Subjects in Cohorts 3, 4, and 5 received a single daily dose of ferrous gluconate (325 mg). The iron supplement was administered to evaluate study medication tolerability when taken with iron. No subjects discontinued due to AEs or safety concerns. Fewer subjects reported an event in the highest dose cohort following eating a meal (20 mg/kg) than were reported in the lower dose cohorts (2, 5 and 10 mg/kg).

Safety Observations

The AEs observed in this study are described in Table 11. All events were assessed as mild by the Principal Investigator and resolved either on study or post study. No SAEs were reported. Two subjects had transient lymphadenopathy that were not considered related to study medication. No laboratory abnormalities of significance were noted except one patient developed a urinary tract infection. No clinically significant ECG abnormalities were noted.

TABLE 11

Subject Incidence of AEs by Descending Frequency

| List of Adverse Events | Placebo<br>N = 10<br>(n = %) | DMB<br>N = 31<br>(n = %) |
|---|---|---|
| Headache | 40 | 23 |
| Menstrual cramps | 10 | 6 |
| Diarrhea | | 6 |
| Flatulence | | 6 |
| Nausea | | 6 |
| Pharyngitis | | 6 |
| Fatigue | 10 | 3 |
| Lymphadenopathy, inguinal | 10 | 3 |
| Abdominal pain | | 3 |
| Contusion of elbow | | 3 |
| Gastritis | | 3 |
| Gastroenteritis | | 3 |
| Light-headedness | | 3 |
| Pharyngeal erythema | | 3 |
| Pregnancy | | 3 |
| Reflux esophagitis | | 3 |
| Spasm, esophageal | | 3 |
| Sunburn | | 3 |
| Upper respiratory infection | | 3 |
| Urinary tract infection | | 3 |
| Vaginal candidiasis | | 3 |
| Abdominal distention | 10 | |
| Contusion of hand (s) | 10 | |
| Dyspepsia | 10 | |
| Emesis | 10 | |
| Euphoria | 10 | |
| Foot pain | 10 | |
| Intra-ocular infection | 10 | |
| Lymphadenopathy, axillary | 10 | |

N = number of subjects in each treatment group,
% = percentage of subjects who experienced an AE Coded using preferred terms from MeDRA
Subjects with multiple events coding to one preferred term, were only counted once.

This study was completed with no SAEs, clinically significant AEs or AEs requiring study medication discontinuation. The most common AE was mild headache, which occurred at the same rate in placebo-treated and DMB treated subjects. No dose limiting toxicity was noted.

After the study was completed, elevated creatine phosphokinase (CPK) levels were reported from the site laboratory that had previously been represented as normal or not clinically significant. The Principal Investigator (PI) and the Director of the hospital both indicated that mild to moderate elevations in CPK may reflect prior exercise and are common in their healthy subject population. None of the subjects in this study HQP 2008-002 had associated myalgias, objective weakness, morning stiffness, rash, dark urine, muscle tenderness, atrophy or fasciculations suggestive of a clinical myopathic process.

It is unlikely that DMB therapy is causally associated with CPK elevations because elevations in CPK were observed in both Placebo and DMB subjects, elevations in CPK were observed at baseline in many subjects, there was no clear dose response relationship between DMB dosing and CPK elevations, there were no myopathic clinical findings in subjects with CPK elevations, the Principal Investigator and the Medical Monitor both reported that elevated CPKs are common incidental findings at Phase I clinical trial sites, probably attributable to preceding subject exercise, and none of the elevated CPK values were considered causally related to study drug exposure. However, a relationship between DMB and elevated CPK levels cannot be completely excluded.

Pharmacokinetic Data and Analyses

Pharmacokinetic (PK) analyses of individual subject plasma concentration-time data were conducted for Day 0 (first dose) and Day 13 (at steady-state) in the multi-dose study. In both the single dose (Day 0) and repeat-dose (Day 13) samples, DMB pharmacokinetic analyses have shown low inter-subject variability, a linear increase in $C_{max}$ and AUC, and a mean $T_{1/2}$ of 11 hours at doses of 10 and 15 mg/kg. Administration under fed conditions demonstrated similar AUC to fasting conditions, although $T_{max}$ was delayed to between 2.5 to 4.4 hours. Analysis of PK data has shown that plasma drug levels >20 ug/mL persist for greater than 10 hours at the 10 and 15 mg/kg dose levels.

Figure 11:
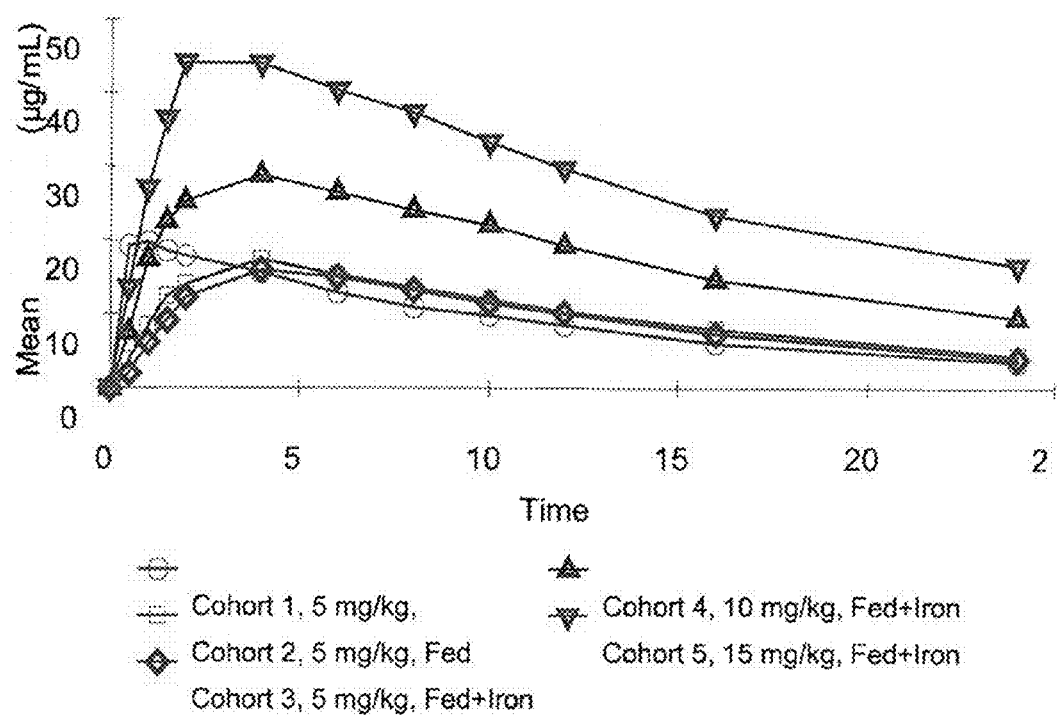
FIG. 11 is a graphic representation of the mean plasma DMB concentration versus time on day 0 of a repeat-dose study of DMB in healthy human subjects.
Figure 12:
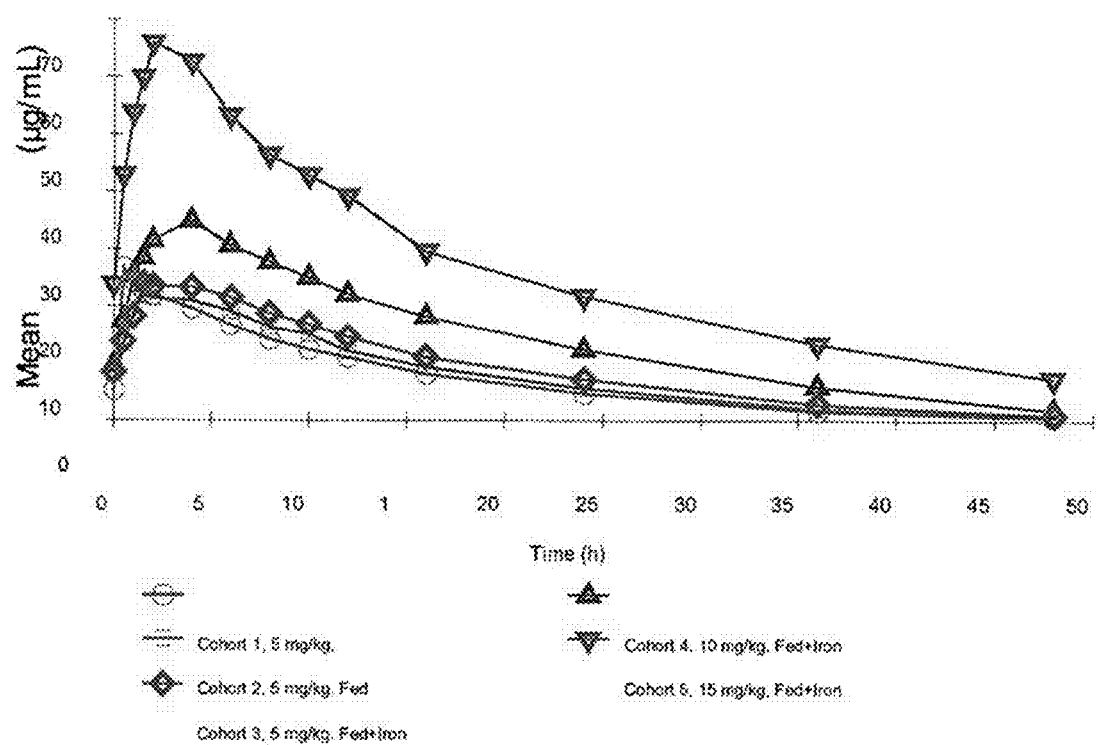
FIG. 12 is a graphic representation of the mean plasma DMB concentration versus time on day 13 of a repeat-dose study of DMB in healthy human subjects.

Mean plasma concentrations of DMB are shown by treatment group for Day 0 (FIG. 11) and Day 13 (FIG. 12) in the repeat-dose clinical study. Based upon non-compartmental analysis of individual subject concentration-time data, the estimated mean DMB plasma $C_{max}$ increased linearly with dose, averaging 16.3, 30.6, and 48.3 μg/mL at 5, 10 and 15 mg/kg, respectively, after the single dosing at Day 0 (fed subjects). Day 13 $C_{max}$ values of 24.8, 35.7, and 67.6 mg/mL at 5, 10 and 15 nig/kg, respectively, were slightly greater on Day 13 than on Day 0, and also increased linearly with dose. $T_{max}$ at all dose levels on both days averaged 2.5 to 4.4 hours after dosing with food.

AUC values displayed a similar pattern as $C_{max}$. $AUC_{0-24}$ increased linearly with dose averaging 226, 441, and 697 h*μg/mL at 5, 10 and 15 mg/kg, respectively, after single dosing at Day 0 (fed subjects). Day 13 AUCτ values of 360, 538, and 958 h*μg/mL were slightly greater at 5, 10 and 15 mg/kg, respectively, than on Day 0, and also increased linearly with dose.

Average $C_{max}$ values for the 5 mg/kg dose with and without iron were similar averaging 16.3 μg/mL and 17.7 μg/mL on Day 0, and 24.8 mg/mL and 22.4 μg/mL on Day 13. $AUC_{0-24}$ averaged 226 and 241 h*μg/mL on Day 0 and AUCT values averaged 360 and 312 h*μg/mL with and without iron, respectively, demonstrating that co-administration with iron does not affect the PK profile of DMB.

The presence of food delays the $T_{max}$ and slightly decreases the $C_{max}$, but has no effect on the AUC, either after a single dose or at steady state with multiple doses. Concomitant administration of iron with DMB in the fed state had no effects on the PK profile of the drug. DMB displayed linear pharmacokinetics over the 5 to 15 mg/kg dose range, following both single and multiple doses, when administered in the fed state with iron. Targeted plasma drug levels were maintained for more than 10 hours at dose levels of 10 and 15 mg/kg.

Pharmacodynamic Data and Analyses

Figure 13:
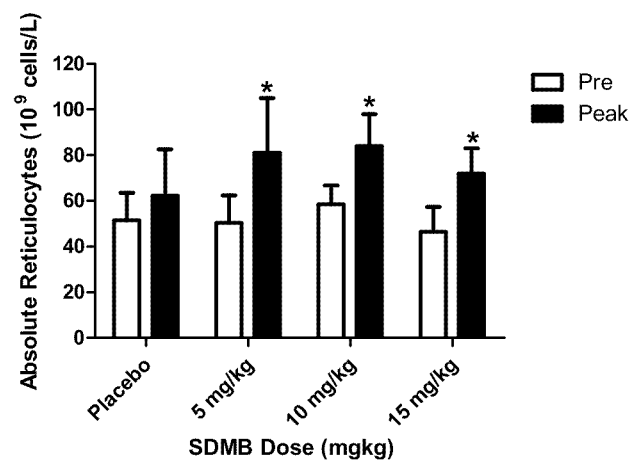
FIG. 13 is a graphic representation of changes in mean absolute reticulocytes assayed by Advia Coulter Counter from baseline (white bars) and peak on treatment (dark bars) are shown in placebo and active treatment groups; significant changes are noted with an asterisk above the bar.

This study was designed for evaluations of DMB safety and PK and did not provide dosing of sufficient duration to fully characterize DMB pharmacodynamics. Nonetheless, limited pharmacodynamics data collected in the repeat-dose study revealed changes in absolute reticulocytes between mean baseline and peak values, usually occurring 2 weeks following completion of study dosing (at Day 27), consistent with the timing required for maturation of red blood cell precursors, as shown in FIG. 13. Mean absolute reticulocytes ($10^9$ cells/L) in the placebo group at baseline and Day 27 were 51+/−12 and 62+/−20, respectively, which was not statistically significant (p=0.19). Mean absolute reticulocytes increased on average from 50% to 60% above the mean baseline values in the subjects who received study medication. For example, at baseline in Cohort 1 (5 mg/kg, fasted) mean absolute reticulocytes were 50+/−12 and mean peak reticulocytes were 81+/−24, (p=0.02); in Cohort 4 (10 mg/kg) mean baseline reticulocytes were 58+/−8 and mean peak reticulocytes were 84+/−14, (p=0.003), and in Cohort 5 (15 mg/kg; fed), the mean baseline was 46+/−11 and mean peak level was 72+/−11, a 50% increase (p=0.001). Increases in absolute reticulocytes, without hemolysis, suggested an erythropoietic effect at all dose levels in the 2-week dosing study, an early indication of erythropoietic effects.

Example 12

Phase 2 Clinical Trial in Thalassemia Intermedia Patients

A randomized, doubled blind, placebo-controlled, multiple ascending dose Phase I/II trial was conducted in 21 adult patients with beta thalassemia intermedia, including 14 patients with HbE/β⁰ thalassemia from Thailand and 7 patients with β⁺/β⁰ thalassemia (including 12 different beta globin gene mutations). Study medication was taken as a single daily dose of DMB for 8 weeks followed minimally by a 4 week break and follow-up period. Four ascending dose levels (10, 20, 30, and 40 mg/kg/day) were sequentially evaluated in 4 dose level cohorts after the preceding dose and schedule were determined safe by an independent and unblinded Safety Monitoring Committee.

All treatment groups had two placebo patients; placebo patients in the first dose group were randomized to treatment in the second dose group. Ten patients in Thailand (all HbE type) were treated with 10 mg/kg (8 active/2 placebo) followed by eight patients in Thailand who were treated followed by 30 mg/kg (6 active/2 placebo). Eleven patients (4 That, 7 Lebanese) were treated with 20 mg/kg followed by 40 mg/kg (9 active [6 Lebanese/3 That]/2 placebo). Patients ranged in age from 17 to 49 with a median age of 31 and were comprised for 16 females and 5 males.

TABLE 12

Characteristics of Patients Enrolled in Beta Thalassemia Clinical Trial

| | Placebo (n = 8) | 10 mg/kg (n = 8) | 20 mg/kg (n = 9) | 30 mg/kg (n = 6) | 40 mg/kg (n = 9) |
|---|---|---|---|---|---|
| Sex | | | | | |
| Male | 2 (25%) | 1 (13%) | 2 (22%) | 2 (33) | 2 (22) |
| Female | 6 (75%) | 7 (87%) | 7 (78%) | 4 (67) | 7 (78) |

TABLE 12-continued

Characteristics of Patients Enrolled in Beta Thalassemia Clinical Trial

|  | Placebo (n = 8) | 10 mg/kg (n = 8) | 20 mg/kg (n = 9) | 30 mg/kg (n = 6) | 40 mg/kg (n = 9) |
|---|---|---|---|---|---|
| Age | | | | | |
| Median | 31 | 34 | 24 | 30 | 32 |
| Range | 17-49 | 20-45 | 20-35 | 17-35 | 21-49 |
| Baseline HbF (%) | | | | | |
| Median | 29.7 | 31.5 | 32.1 | 38.9 | 25.9 |
| Range | 13.2-52.7 | 9.0-53.7 | 9.5-87.6 | 21.9-47.8 | 15.7-92.7 |
| Baseline Hb (g/dL) | | | | | |
| Median | 6.6 | 7.7 | 7.2 | 8.7 | 6.1 |
| Range | 5.5-9.6 | 6.0-9.6 | 5.6-9.2 | 5.8-9.9 | 5.3-9.2 |
| Region | | | | | |
| Thailand | 6 (75%) | 8 (100%) | 3 (33.3%) | 6 (100%) | 3 (33.3%) |
| Lebanon | 2 (25%) | 0 (0%) | 6 (66.7%) | 0 (0%) | 6 (66.7%) |

Patients were monitored every 2 weeks for laboratory studies, physical examinations, and adverse events. Further, patients were followed for hematologic parameters primarily focusing on hemoglobin and fetal hemoglobin (HbF). In addition, pharmacokinetic samples were obtained on Day 0 and 13, at pre-dose and 2, 4, 6, 8, 12, and 24 hours post-dosing. Hemoglobin was measured at each site using standard hematology equipment. HbF was measured using Varian HPLC. DMB was well tolerated. Adverse events in treated subjects included headache, upper respiratory infection, pyrexia, fatigue, nausea, and dizziness, but the rates of such events were not markedly different from those observed in the placebo-treated subjects. No dose response was observed for adverse events in this study.

TABLE 13

Summary of Adverse Events in Beta Thalassemia Clinical Trial (greater than 15% incidence in pooled DMB treated subjects)

| Event | Placebo n (%) | 10 mg/kg n (%) | 20 mg/kg n (%) | 30 mg/kg n (%) | 40 mg/kg n (%) |
|---|---|---|---|---|---|
| Headache | 2 (25) | 5 (63) | 3 (33) | 2 (33) | 1 (11) |
| Upper Respiratory Tract Infection | 3 (38) | 5 (63) | 2 (22) | 1 (17) | 1 (11) |
| Pyrexia | 2 (25) | 3 (38) | 0 | 2 (33) | 1 (11) |
| Fatigue | 1 (13) | 1 (13) | 0 | 0 | 4 (44) |
| Nausea | 0 | 0 | 2 (22) | 0 | 3 (33) |
| Dizziness | 0 | 2 (25) | 2 (22) | 0 | 1 (11) |

A total of 5 subjects experienced 5 serious adverse events (SAEs). All SAEs were considered unlikely or not related to study medication. Three subjects experienced an adverse event which led to study medication discontinuation. Two subjects who received 10 mg/kg DMB discontinued study medication due to anemia; both were considered not related to study medication.

TABLE 14

Summary of Serious Adverse Events

| Event | Placebo n (%) | HQK-1001 n (%) | Treatment Related? |
|---|---|---|---|
| Palpitations | 0 | 1 (13) 10 mg/kg | Not related to treatment |
| Suprapubic Pain | 0 | 1 (11) 20 mg/kg | Unlikely related to treatment |
| Gastritis | 0 | 1 (11) 40 mg/kg | Not related to treatment |
| Gastroenteritis | 1 (13) | 0 | Not related to treatment |
| Upper Respiratory Infection | 1 (13) | 0 | Not related to treatment |

Figure 14:
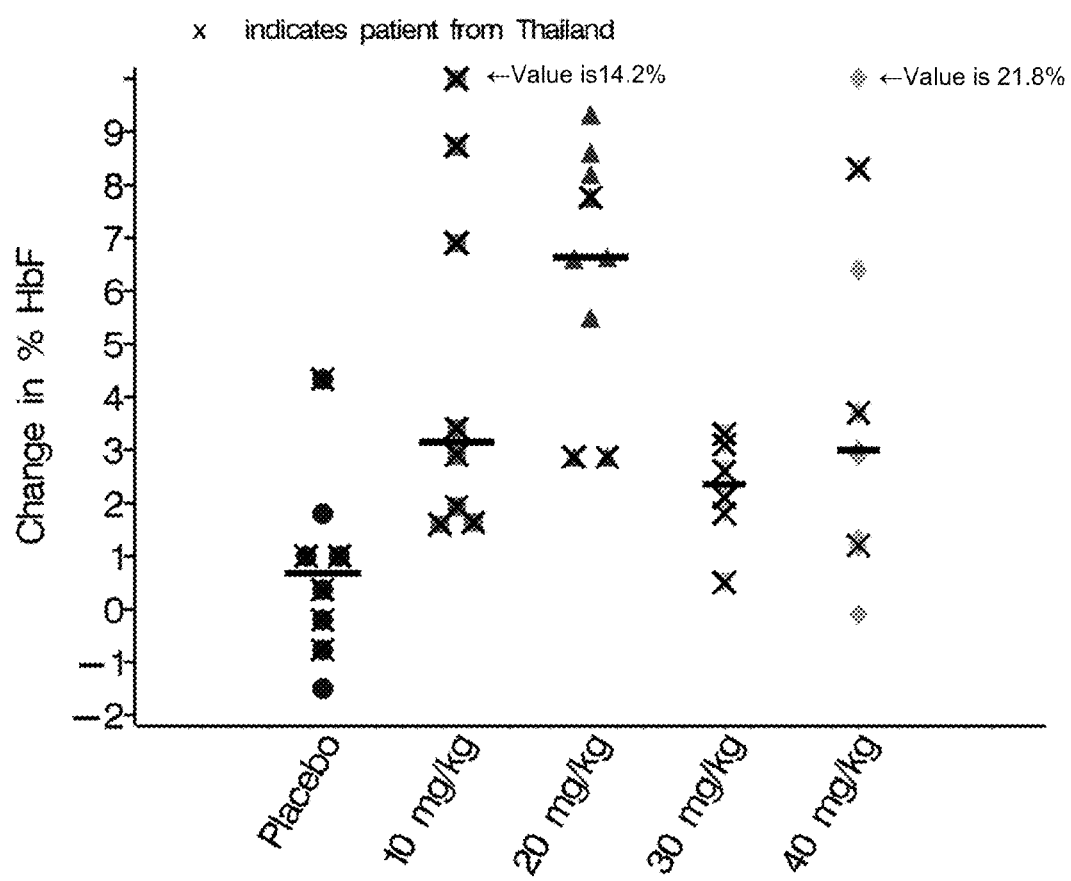
FIG. 14 is a graphic representation of the change of percentage of fetal hemoglobin (HbF) for several dose levels in a repeat-dose study of DMB in beta thalassemia patients from Thailand and Lebanon (x indicates patients from Thailand).
Figure 15:
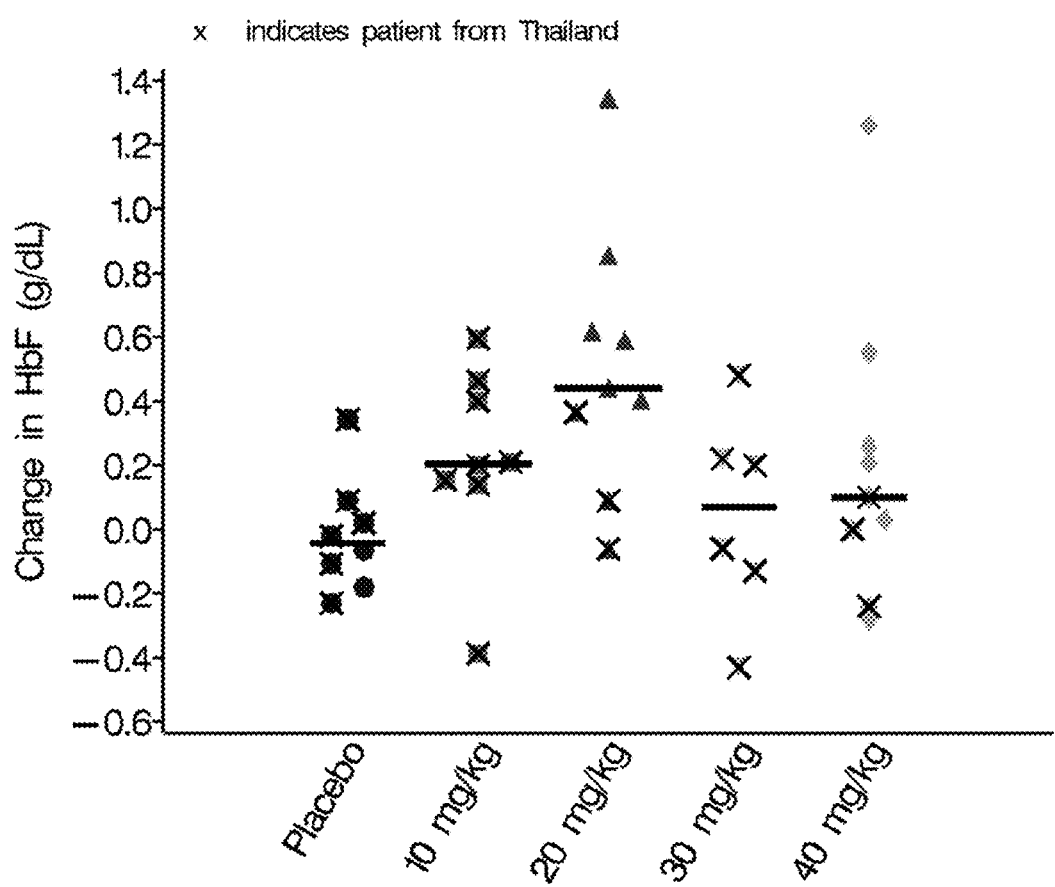
FIG. 15 is a graphic representation of the change of fetal hemoglobin (HbF) concentration for several dose levels in a repeat-dose study of DMB in beta thalassemia patients from Thailand and Lebanon (x indicates patients from Thailand).
Figure 16:
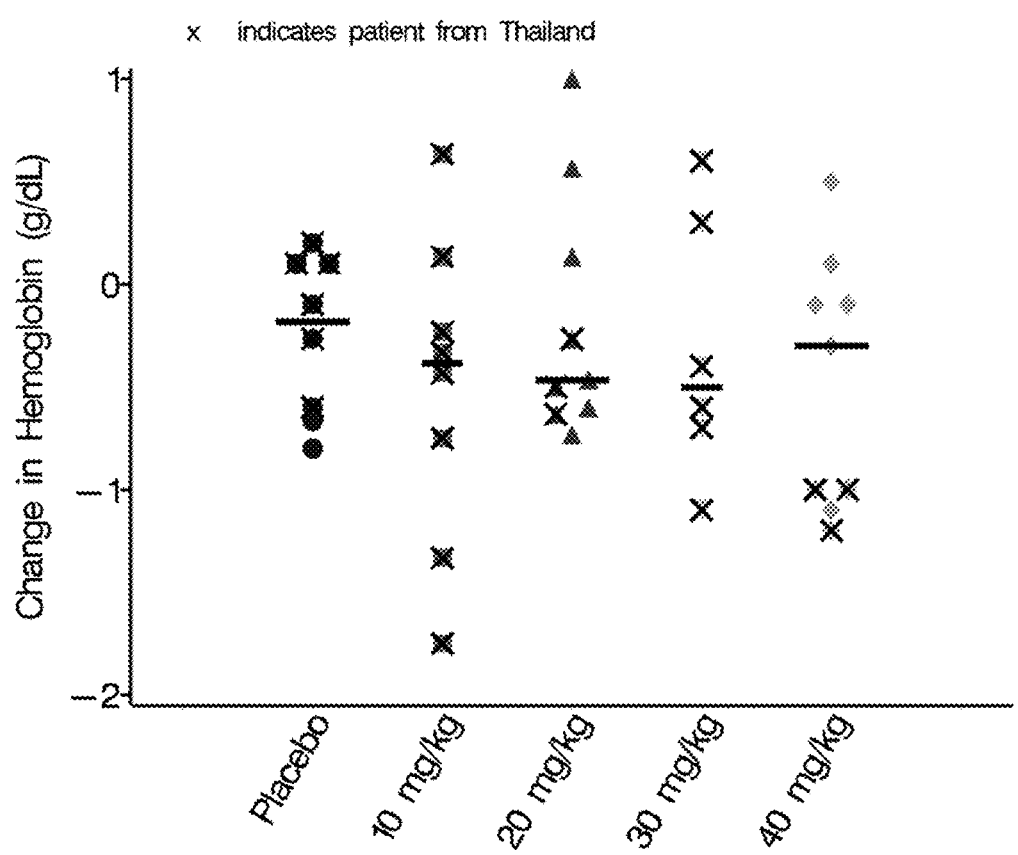
FIG. 16 is a graphic representation of the change of total hemoglobin (Hgb) for several dose levels in a repeat-dose study of DMB in beta thalassemia patients from Thailand and Lebanon (x indicates patients from Thailand).

At Day 55, median increases in HbF were observed in all 4 DMB dose groups compared to a minimal change seen in the placebo group. The dose level with the largest increase in HbF was the 20 mg/kg group (FIG. 14). A similar trend was observed for the change in absolute fetal hemoglobin (FIG. 15). Median change from baseline to Day 55 in total hemoglobin showed decreases in all groups including the placebo group, but total hemoglobin increased in some patients, e.g., 2 out of 9 patients in the 20 mg/kg group, including 2 of 6 Lebanese patients with beta thalassemia mutations without HbE (FIG. 16).

Figure 17:
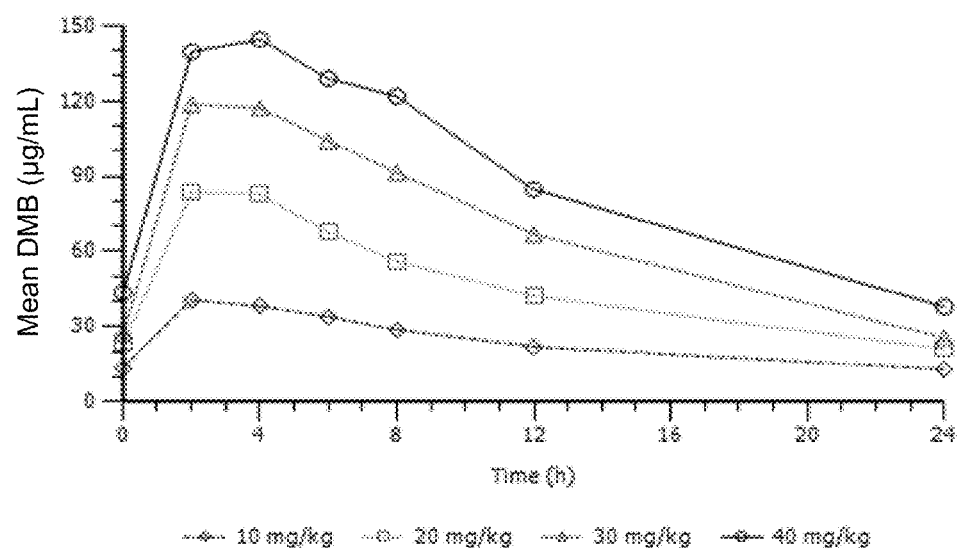
FIG. 17 is a graphic representation of the mean plasma DMB concentration versus time for various subjects at different dose levels in a beta thalassemia phase 2 clinical trial.

A noncompartmental PK analysis was conducted using steady state concentration-time data for Day 13. Dose proportional increases in overall exposure as measured by AUC ranged from 579 to 2110 h*μg/mL over the dose range studied. Maximum concentration ($C_{max}$) increased with increase in dose, with means ranging from 41.2 to 154 μg/mL over the 10 to 40 mg/kg dose range. The time to peak plasma concentration ($T_{max}$) ranged from 2.5 to 3.1 hours, while the terminal half-life ($T_{1/2}$) for sodium DMB decreased from 12.1 hours in the 10 mg/kg dose group to 10.3 hours in the 40 mg/kg dose group (FIG. 17).

In specific instances, DMB concentrations of 400 to 600 μM correspond to plasma concentrations of about 55-80 μg/mL, which are achieved at doses of about 20 mg/kg. Dosing of 30 mg/kg or 40 mg/kg achieves peak concentrations of about 120-140 μg/mL, which is equivalent to about 1000 μM.

The observations from this clinical trial indicate that DMB is well tolerated at doses associated with favorable initial pharmacodynamics effect on HbF. These doses are below the maximum tolerated dose.

Example 13

Phase 2 Clinical Trial in Sickle Cell Disease Patients

A randomized, blinded dose-ranging Phase 1/2 clinical trial was performed in 24 US and Jamaican adult patients with sickle cell disease (including HbSS or S/β thalassemia). DMB was administered once daily for six week cycles of daily therapy with a 2 week treatment break between two cycles, then followed by a final 4 weeks without treatment. Three dose levels (10, 20, 30 mg/kg/day) were studied sequentially. Four out of 24 subjects were treated with placebo and 21 subjects were evaluable. Seven Patients (5 active/2 placebo) at 10 mg/kg, 6 patients (5 active/1 placebo) at 20 mg/kg, and 9 patients (7 active/1 placebo) at 30 mg/kg were randomized in the study. Patients ranged in age from 14 to 56 with a median age of 31 and were comprised of 10 females and 15 males. Patients were followed for hematologic parameters focusing on fetal hemoglobin (HbF). HbF was measured by a Waters Empower 32 HPLC system with a Synchropak CM-300 column.

DMB was well tolerated with no significant drug-related adverse events. No dose response was observed for adverse events in this study.

Figure 18:
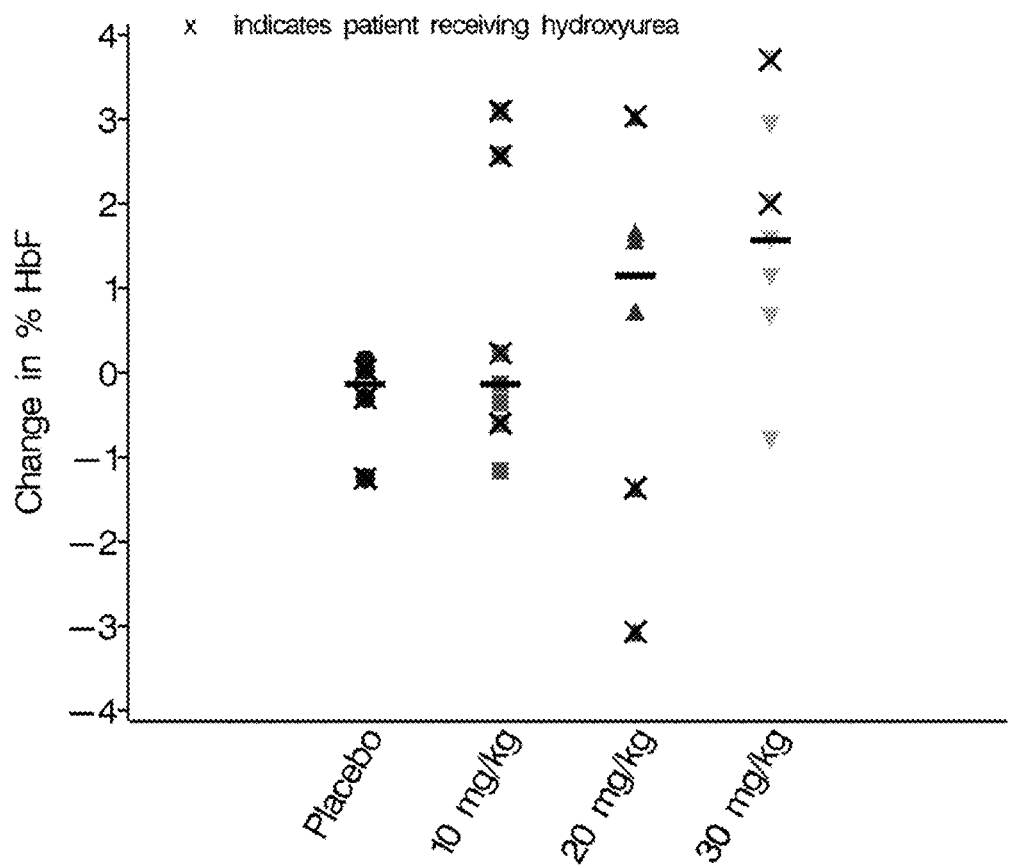
FIG. 18 is a graphic representation of the change of percentage of fetal hemoglobin (HbF) for several dose levels in a repeat-dose study of DMB in sickle cell disease patients (x indicates patients also receiving hydroxyurea).
Figure 19:
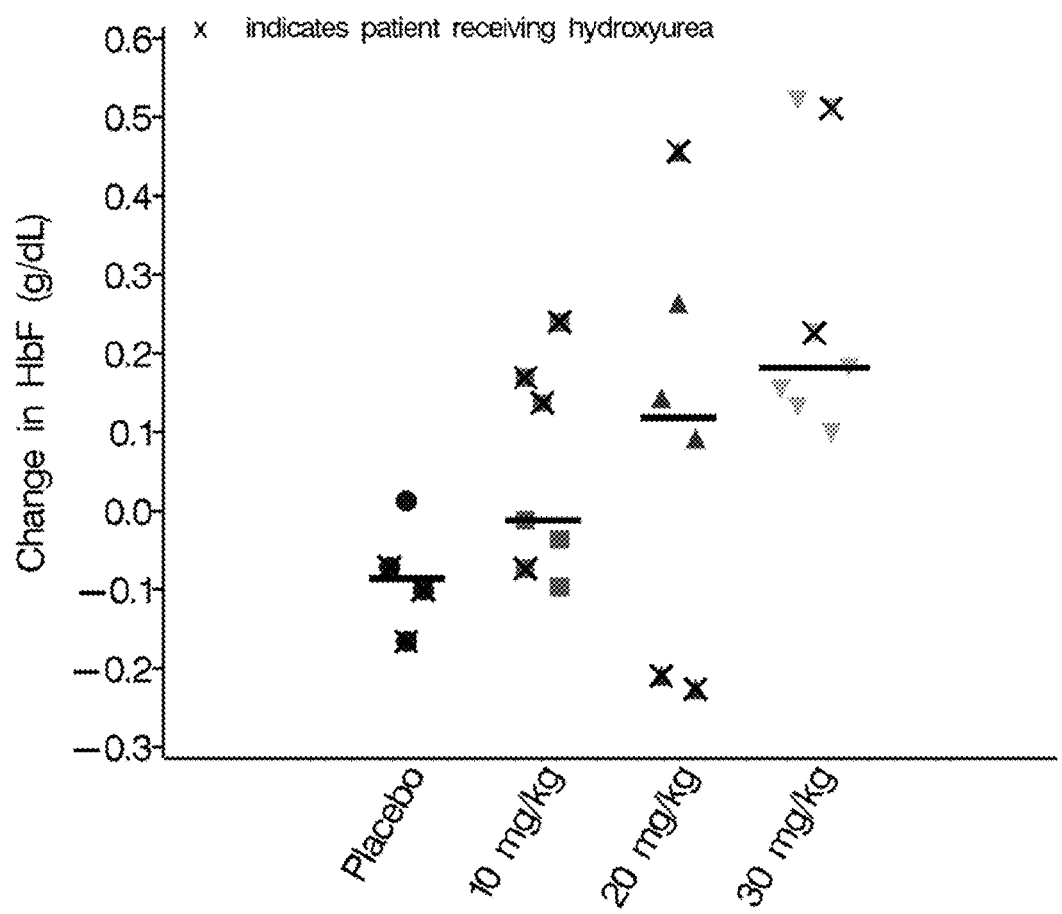
FIG. 19 is a graphic representation of the change of fetal hemoglobin (HbF) concentration from baseline to end of therapy for several dose levels in a repeat-dose study of DMB in sickle cell disease patients (x indicates patients also receiving hydroxyurea).
Figure 20:
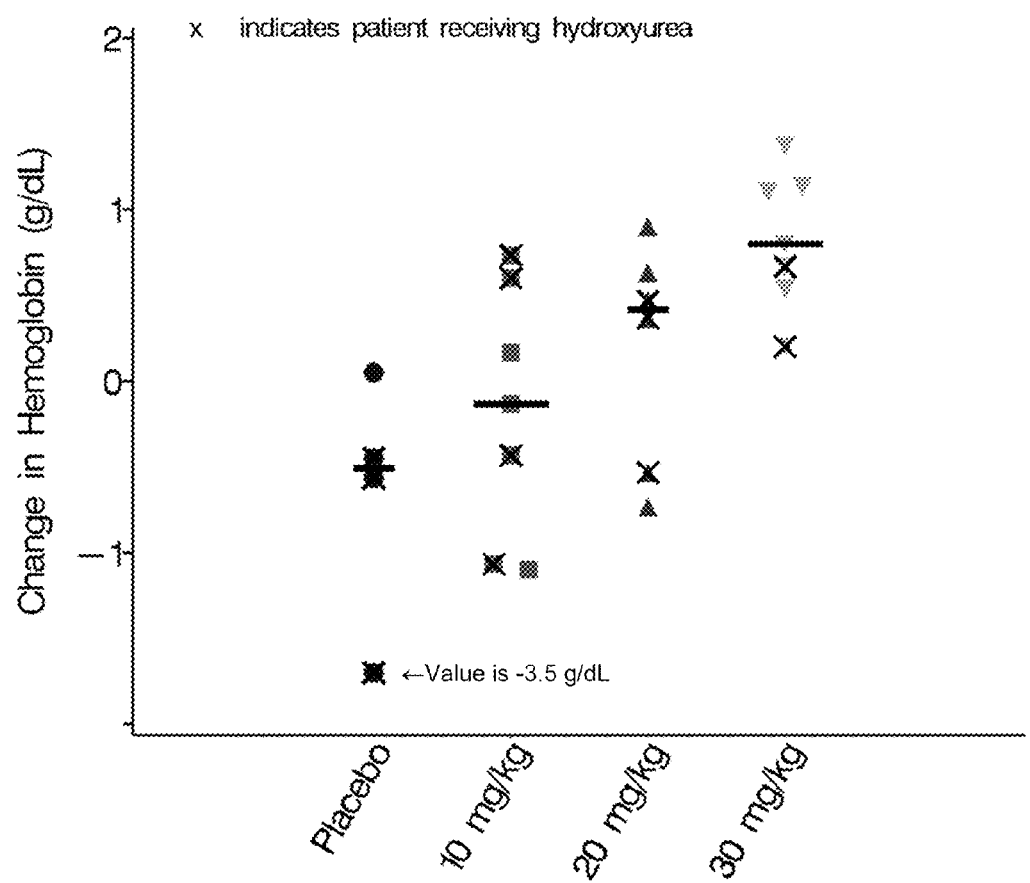
FIG. 20 is a graphic representation of the change of total hemoglobin (Hgb) concentration from baseline to end of therapy for several dose levels in a repeat-dose study of DMB in sickle cell disease patients (x indicates patients also receiving hydroxyurea).

At Day 97, median increases in percent HbF, as shown in FIG. 18, were observed in all 3 DMB dose groups compared to a decrease in the placebo group. The dose level with the largest increase in HbF was the 30 mg/kg group. Preliminary data suggests a trend of higher magnitude of effect as dose increased from 10 to 20 to 30 mg/kg. Median increases in absolute HbF, as shown in FIG. 19, were also observed at Day 97 in all three DMB dose groups compared to a lower increase in the placebo group. Furthermore, median increases in total Hgb, as shown in FIG. 20, were observed at Day 97 in all three DMB dose groups compared to a decrease in the placebo group. Similar to the effect seen in HbF, the dose level with the largest increase in total Hgb was the 30 mg/kg group. A similar trend for increase in Hgb to that observed for increase in HbF was observed with a higher magnitude of effect as dose increased from 10 to 20 to 30 mg/kg.

In certain instances, the increase in total hemoglobin is an indication for the stimulation of red blood cell production and/or the longer survival of sickled blood cells. Lactate dehydrogenase (LDH), a marker of tissue breakdown because LDH is abundant in red blood cells and can function as a marker for hemolysis, declined in 4 of 5 responding subjects receiving 30 mg/kg doses.

Figure 21:
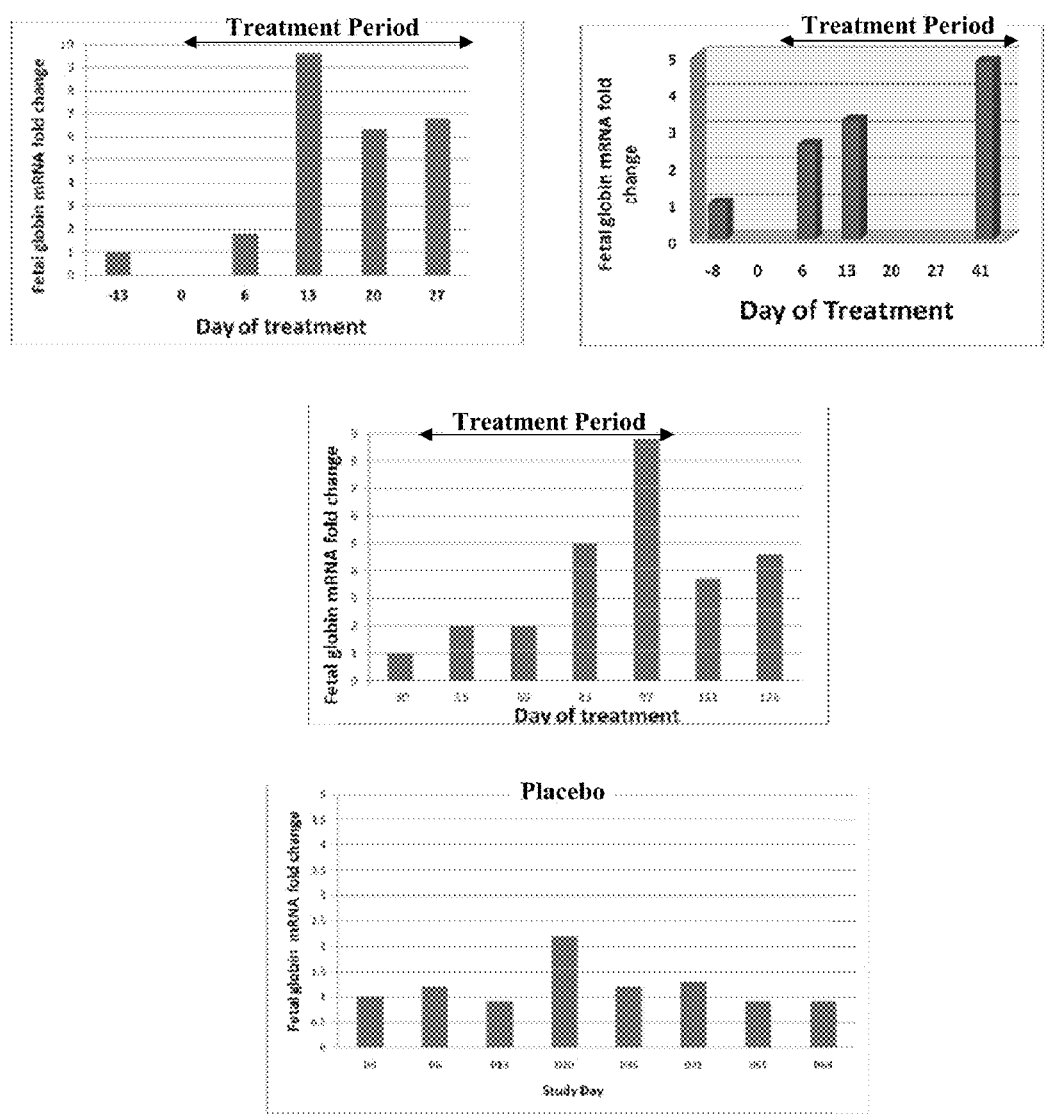
FIG. 21 is a graphic representation of the change in fetal globin mRNA in three sickle cell disease patients being treated with 10 mg/kg of DMB during the periods indicated in the first three graphs as compared to a placebo patient (bottom).

Fetal globin mRNA increased by 4- to 9-fold over the subjects' baseline throughout the study period in patients treated with 10 mg/kg doses, and it was still increasing at the end of the dosing period, implying that HbF expression had not yet peaked (FIG. 21). This large increase in fetal globin mRNA was not observed in placebo treated patients. Other fetal globin inducing agents such as hydroxyurea require 6-9 months of treatment, at a level close to the maximum tolerated dose, for optimal effects on HbF to be achieved.

Figure 22:
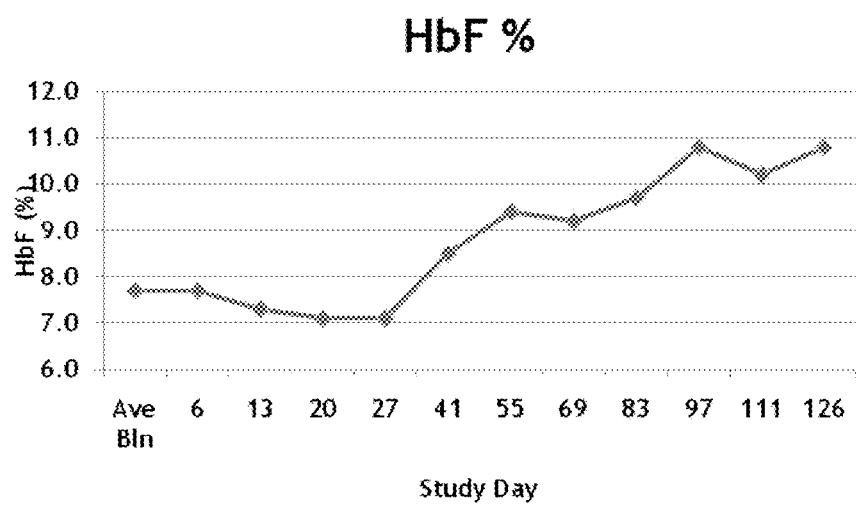
FIG. 22 is a graphic representation of the change in percentage fetal hemoglobin (HbF) and the percentage of F-cells in one sickle cell disease patient during treatment with 10 mg/kg of DMB up to Day 97 and during post-treatment follow-up.
Figure 22:
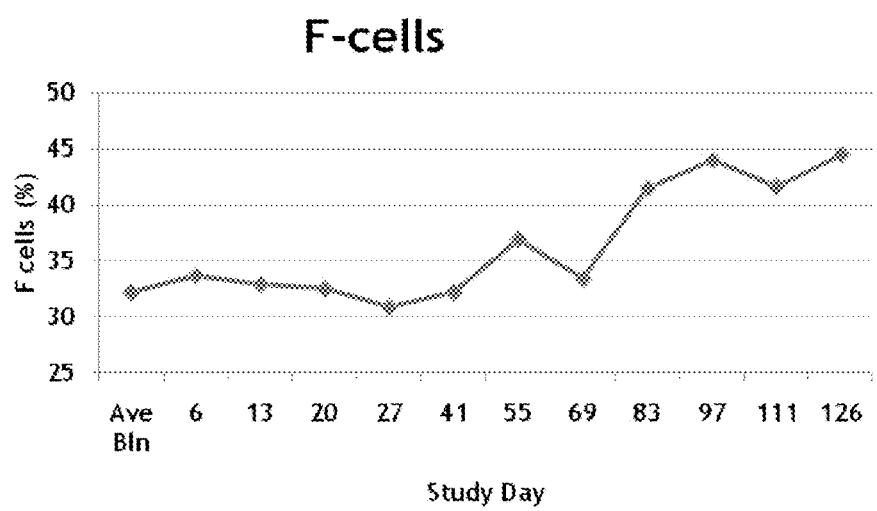

In some instances, the percentage of F-cells as well as the percentage of fetal hemoglobin increased throughout the treatment period. Furthermore, post-treatment (after Day 97) the percentage of F-cells and fetal hemoglobin continue to increase in some subjects (FIG. 22).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for increasing the percentage of fetal hemoglobin in the blood of a subject, comprising administering to said subject 2,2-dimethylbutyrate as the free acid, a pharmaceutically acceptable salt, or ester thereof;
   wherein a total daily dose of 2,2-dimethylbutyrate is more than 10 mg/kg and not more than 40 mg/kg; and wherein after the administration the percentage of fetal hemoglobin in the blood of the subject increases.

2. The method of claim 1, wherein the 2,2-dimethylbutyrate is administered as sodium 2,2-dimethylbutyrate.

3. The method of claim 1, wherein said administering is by oral administration.

4. The method of claim 1, wherein the subject has been diagnosed with a blood disorder or anemia.

5. The method of claim 4, wherein the blood disorder is a sickle cell disease.

6. The method of claim 4, wherein the blood disorder is a beta thalassemia.

7. The method of claim 1, wherein the total daily dose of 2,2-dimethylbutyrate is about 30 mg/kg.

8. The method of claim 1, wherein the plasma concentration of 2,2-dimethylbutyrate does not exceed a concentration of 170 µg/mL.

9. The method of claim 1, wherein the amount of fetal hemoglobin in the blood of the subject increases.

10. The method of claim 1, wherein the amount of total hemoglobin in the blood of the subject increases.

11. The method of claim 1, wherein said subject is a mammal.

12. The method of claim 11, wherein said mammal is a human.

13. The method of claim 12, wherein said human is a child.

14. A method for increasing the percentage of fetal hemoglobin in the blood of a subject comprising administering to said subject:
   a) 2,2-dimethylbutyrate as the free acid, a pharmaceutically acceptable salt, or ester thereof, wherein a total daily dose of 2,2-dimethylbutyrate is more than 10 mg/kg and not more than 40 mg/kg; and
   b) one or more agents selected from the group consisting of hydroxyurea, decitabine, and an HDAC inhibitor;
   wherein after the administration the percentage of fetal hemoglobin in the blood of the subject increases.

15. The method of claim 14, wherein the subject has been diagnosed with a beta thalassemia.

16. The method of claim 14, wherein the 2,2-dimethylbutyrate is administered as sodium 2,2-dimethylbutyrate.

17. The method of claim 14, wherein said administering is by oral administration.

18. The method of claim 14, wherein the plasma concentration of 2,2-dimethylbutyrate does not exceed a concentration of 170 µg/mL.

19. The method of claim 14, wherein the amount of fetal hemoglobin in the blood of the subject increases.

20. The method of claim 14, wherein the amount of total hemoglobin in the blood of the subject increases.

21. The method of claim 1, further comprising administering to said subject hydroxyurea, decitabine, an HDAC inhibitor, or a combination thereof.

22. The method of claim 14, wherein the subject has been diagnosed with a blood disorder or anemia.

23. The method of claim 22, wherein the blood disorder is a sickle cell disease.

24. The method of claim 23, wherein a total daily dose of 2,2-dimethylbutyrate is about 30 mg/kg day.

25. The method of claim 24, wherein 2,2-dimethylbutyrate is administered at a dose of about 15 mg/kg twice a day.

26. The method of claim 7, wherein 2,2-dimethylbutyrate is administered at a dose of about 15 mg/kg twice a day.

27. The method of claim 14, wherein said subject is a mammal.

28. The method of claim 27, wherein said mammal is a human.

29. The method of claim 28, wherein said human is a child.

* * * * *